US009193827B2

(12) United States Patent
Ma et al.

(10) Patent No.: US 9,193,827 B2
(45) Date of Patent: Nov. 24, 2015

(54) POLY(BETA-AMINO ALCOHOLS), THEIR PREPARATION, AND USES THEREOF

(75) Inventors: Minglin Ma, Cambridge, MA (US); Wendy F. Liu, Irvine, CA (US); Robert S. Langer, Newton, MA (US); Daniel Griffith Anderson, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 77 days.

(21) Appl. No.: 13/819,280

(22) PCT Filed: Aug. 26, 2011

(86) PCT No.: PCT/US2011/049360
§ 371 (c)(1),
(2), (4) Date: May 14, 2013

(87) PCT Pub. No.: WO2012/027675
PCT Pub. Date: Mar. 1, 2012

(65) Prior Publication Data
US 2013/0302401 A1  Nov. 14, 2013

Related U.S. Application Data

(60) Provisional application No. 61/377,348, filed on Aug. 26, 2010.

(51) Int. Cl.
| C08G 73/02 | (2006.01) |
| A61L 31/10 | (2006.01) |
| C09D 5/16 | (2006.01) |
| C08G 59/22 | (2006.01) |
| C08G 59/30 | (2006.01) |
| C08G 59/50 | (2006.01) |
| C09D 179/02 | (2006.01) |

(52) U.S. Cl.
CPC ............. *C08G 73/02* (2013.01); *A61L 31/10* (2013.01); *C08G 59/22* (2013.01); *C08G 59/306* (2013.01); *C08G 59/50* (2013.01); *C09D 5/1637* (2013.01); *C09D 179/02* (2013.01); *Y10T 428/31725* (2015.04)

(58) Field of Classification Search
None
See application file for complete search history.

(56) References Cited

U.S. PATENT DOCUMENTS

| 2,647,121 A | 7/1953 | Jacoby |
| 2,717,909 A | 9/1955 | Kosmin |
| 2,759,913 A | 8/1956 | Hulse |
| 2,819,718 A | 1/1958 | Goldman |
| 2,844,629 A | 7/1958 | William et al. |
| 3,096,560 A | 7/1963 | Liebig |
| 3,350,325 A * | 10/1967 | Ashby et al. ............... 528/408 |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,963,771 A | 6/1976 | Robson et al. |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,224,365 A | 9/1980 | Ali-Zaidi |
| 4,227,533 A | 10/1980 | Godfrey |
| 4,284,459 A | 8/1981 | Patel et al. |
| 4,308,085 A | 12/1981 | Horhold et al. |

(Continued)

FOREIGN PATENT DOCUMENTS

| CA | 2518132 A1 | 3/2006 |
| CN | 100 569 877 C | 12/2009 |

(Continued)

OTHER PUBLICATIONS

Gademann et al., Angew. Chem. Int. Ed., 2003, 42(13) pp. 1534-1537.*
Invitation to Pay Additional Fees for PCT/US2012/062222, mailed Dec. 14, 2012.
International Search Report and Written Opinion for PCT/US2012/062222, mailed Mar. 27, 2013.
Extended European Search Report for EP 06784878.8, mailed Jun. 29, 2009.

(Continued)

*Primary Examiner* — Brian Gulledge
(74) *Attorney, Agent, or Firm* — Wolf, Greenfield & Sacks, P.C.

(57) ABSTRACT

A new class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering.

25 Claims, 7 Drawing Sheets

(56) References Cited

U.S. PATENT DOCUMENTS

| | | |
|---|---|---|
| 4,323,525 A | 4/1982 | Bornat |
| 4,335,723 A | 6/1982 | Patel |
| 4,339,369 A | 7/1982 | Hicks et al. |
| 4,348,511 A | 9/1982 | Haug |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,180,424 A | 1/1993 | Hutter |
| 5,197,977 A | 3/1993 | Hoffman, Jr. et al. |
| 5,200,395 A | 4/1993 | Eto et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,364,634 A | 11/1994 | Lew |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,462,990 A | 10/1995 | Hubbell et al. |
| 5,464,924 A | 11/1995 | Silvis et al. |
| 5,503,852 A | 4/1996 | Steiner et al. |
| 5,525,357 A | 6/1996 | Keefer et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,736,573 A | 4/1998 | Galat |
| 5,770,637 A | 6/1998 | Vanderlaan et al. |
| 5,772,694 A | 6/1998 | Bokros et al. |
| 5,776,165 A | 7/1998 | Ripart |
| 5,776,747 A | 7/1998 | Schinstine et al. |
| 5,858,746 A | 1/1999 | Hubbell et al. |
| 5,874,105 A | 2/1999 | Watkins et al. |
| 5,885,613 A | 3/1999 | Holland et al. |
| 5,904,927 A | 5/1999 | Amiji |
| 5,910,168 A | 6/1999 | Myers et al. |
| 5,916,208 A | 6/1999 | Luther et al. |
| 5,962,520 A | 10/1999 | Smith et al. |
| 5,976,569 A | 11/1999 | Milstein |
| 6,055,454 A | 4/2000 | Heemels |
| 6,060,582 A | 5/2000 | Hubbell et al. |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,696,424 B1 | 2/2004 | Wheeler |
| 6,756,055 B2 | 6/2004 | McDonald et al. |
| 6,821,530 B2 | 11/2004 | Koob et al. |
| 6,887,665 B2 | 5/2005 | Trulson et al. |
| 6,984,404 B1 | 1/2006 | Talton et al. |
| 6,998,115 B2 | 2/2006 | Langer et al. |
| 7,022,214 B2 | 4/2006 | Olech |
| 7,084,303 B2 | 8/2006 | Watanabe et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,972,435 B2 | 7/2011 | Bury et al. |
| 7,977,452 B2 | 7/2011 | Tomalia et al. |
| 8,071,082 B2 | 12/2011 | Zugates et al. |
| RE43,612 E | 8/2012 | Anderson et al. |
| 8,287,849 B2 | 10/2012 | Langer et al. |
| 8,361,555 B2 | 1/2013 | Paquet, Jr. |
| 8,450,298 B2 | 5/2013 | Mahon et al. |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 | 3/2015 | Mahon et al. |
| 2002/0022721 A1 | 2/2002 | Trulson et al. |
| 2002/0094528 A1 | 7/2002 | Salafsky |
| 2002/0131951 A1 | 9/2002 | Langer et al. |
| 2002/0192721 A1 | 12/2002 | Rizzuto et al. |
| 2002/0193622 A1 | 12/2002 | Watanabe et al. |
| 2003/0215395 A1 | 11/2003 | Yu et al. |
| 2004/0028694 A1 | 2/2004 | Young et al. |
| 2004/0071654 A1 | 4/2004 | Anderson et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0122550 A1 | 6/2005 | Plewa et al. |
| 2005/0143332 A1 | 6/2005 | Monahan et al. |
| 2005/0148786 A1 | 7/2005 | Ikeda et al. |
| 2005/0238716 A1 | 10/2005 | Verrijk et al. |
| 2005/0244961 A1 | 11/2005 | Short et al. |
| 2005/0265961 A1 | 12/2005 | Langer et al. |
| 2006/0062821 A1 | 3/2006 | Simhambhatla et al. |
| 2006/0105975 A1 | 5/2006 | Pendergrast et al. |
| 2006/0223939 A1* | 10/2006 | Lange et al. .................. 524/588 |
| 2006/0228404 A1 | 10/2006 | Anderson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |
| 2010/0196492 A1 | 8/2010 | Green et al. |
| 2011/0009641 A1 | 1/2011 | Anderson et al. |
| 2011/0293703 A1 | 12/2011 | Mahon et al. |
| 2012/0009222 A1 | 1/2012 | Nguyen et al. |

(56) References Cited

U.S. PATENT DOCUMENTS

| | | | |
|---|---|---|---|
| 2012/0065358 A1 | 3/2012 | Langer et al. | |
| 2012/0128760 A1 | 5/2012 | Manoharan et al. | |
| 2012/0149630 A1 | 6/2012 | Zugates et al. | |
| 2012/0196923 A1* | 8/2012 | Rege et al. | 514/44 R |
| 2012/0251560 A1 | 10/2012 | Dahlman et al. | |
| 2013/0158021 A1 | 6/2013 | Dong et al. | |
| 2014/0094399 A1 | 4/2014 | Langer et al. | |
| 2014/0161830 A1 | 6/2014 | Anderson et al. | |
| 2014/0329884 A1 | 11/2014 | Dong et al. | |

FOREIGN PATENT DOCUMENTS

| | | |
|---|---|---|
| CN | 101 863 544 B | 9/2011 |
| DE | 19626567 A1 | 1/1998 |
| EP | 0 673 637 A1 | 9/1995 |
| EP | 0 959 092 A1 | 11/1999 |
| EP | 2 045 251 A1 | 4/2009 |
| EP | 2 532 649 | 12/2012 |
| FR | 1 378 382 | 11/1964 |
| GB | 1072118 A | 6/1967 |
| GB | 1 602 085 A | 11/1981 |
| JP | 51-125144 | 11/1976 |
| JP | 52-045327 A | 4/1977 |
| JP | 63-154788 A | 6/1988 |
| JP | 4-108173 A | 4/1992 |
| JP | 08-092369 A | 4/1996 |
| JP | H09-505593 A | 6/1997 |
| JP | 11-005786 A | 1/1999 |
| JP | H07-053535 | 2/1999 |
| JP | 11-080142 A | 3/1999 |
| JP | 2001-523215 A | 11/2001 |
| JP | 2002-167368 A | 6/2002 |
| JP | 2003-519199 A | 6/2003 |
| JP | 2004-506000 T | 2/2004 |
| JP | 2008-247749 A | 10/2008 |
| WO | WO-93/18229 A1 | 9/1993 |
| WO | WO 93/18754 A1 | 9/1993 |
| WO | WO 95/11004 A1 | 4/1995 |
| WO | WO 95/14651 A1 | 6/1995 |
| WO | WO 96/26179 A1 | 8/1996 |
| WO | WO 96/36314 A2 | 11/1996 |
| WO | WO 97/23457 A1 | 7/1997 |
| WO | WO 98/16202 A2 | 4/1998 |
| WO | WO 00/03044 A1 | 1/2000 |
| WO | WO 01/15726 A2 | 3/2001 |
| WO | WO 02/13767 A2 | 2/2002 |
| WO | WO 02/22709 A1 | 3/2002 |
| WO | WO 02/31025 A2 | 4/2002 |
| WO | WO 02/097068 A2 | 12/2002 |
| WO | WO 03/040288 A2 | 5/2003 |
| WO | WO 03/070735 A2 | 8/2003 |
| WO | WO 2004/043588 A2 | 5/2004 |
| WO | WO 2004/048345 A2 | 6/2004 |
| WO | WO 2004/106411 A2 | 12/2004 |
| WO | WO 2005/028619 A2 | 3/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/143659 | 12/2007 |
| WO | WO 2008/011561 | 1/2008 |
| WO | WO-2008/113364 A2 | 9/2008 |
| WO | WO 2009/046220 A2 | 4/2009 |
| WO | WO 2010/042877 A1 | 4/2010 |
| WO | WO 2010/045512 A2 | 4/2010 |
| WO | WO 2010/053572 A2 | 5/2010 |
| WO | WO 2010/099387 A1 | 9/2010 |
| WO | WO 2010/114789 A1 | 10/2010 |
| WO | WO 2010/129709 A1 | 11/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO 2014/028487 A1 | 2/2014 |
| WO | WO 2014/179562 A1 | 11/2014 |

OTHER PUBLICATIONS

Extended European Search Report for EP 11186795.8, mailed Jun. 19, 2012.
International Search Report and Written Opinion for PCT/US2006/023171, mailed May 29, 2008.
International Preliminary Report on Patentability for PCT/US2006/023171, mailed Jul. 3, 2008.
Extended European Search Report, mailed Jan. 28, 2008, for EP 07013193.3.
International Search Report and Written Opinion for PCT/US2004/016521 mailed Dec. 8, 2004.
International Preliminary Report on Patentability for PCT/US2004/016521 mailed Dec. 15, 2005.
International Search Report and Written Opinion for PCT/US2008/056168 mailed Nov. 6, 2008.
International Preliminary Report on Patentability for PCT/US2008/056168 mailed Sep. 17, 2009.
International Search Report for PCT/US2001/031270 mailed May 22, 2002.
Written Opinion for PCT/US2001/031270 mailed Jan. 2, 2003.
International Preliminary Examination Report for PCT/US2001/031270 mailed Aug. 19, 2003.
Extended European Search Report for EP 07813156.2 mailed Oct. 5, 2009.
International Search Report and Written Opinion for PCT/US2007/073976 mailed Sep. 29, 2008.
International Preliminary Report on Patentability for PCT/US2007/073976 mailed Feb. 5, 2009.
Extended European Search Report for EP 07798132.2 mailed Jul. 18, 2011.
International Search Report and Written Opinion for PCT/US2007/070430 mailed Dec. 13, 2007.
International Preliminary Report on Patentability for PCT/US2007/070430 mailed Dec. 24, 2008.
Extended European Search Report for European Application No. 09825132.5, dated Jul. 16, 2013.
International Search Report and Written Opinion for PCT/US2009/006018, mailed May 25, 2010.
International Preliminary Report on Patentability for PCT/US2009/006018, mailed May 19, 2011.
International Search Report and Written Opinion for PCT/US2009/005810, mailed Jun. 16, 2010.
International Preliminary Report on Patentability for PCT/US2009/005810, mailed May 12, 2011.
International Search Report and Written Opinion for PCT/US2011/049360, mailed Mar. 20, 2012.
International Preliminary Report on Patentability for PCT/US2011/049360, mailed Mar. 7, 2013.
Invitation to Pay Additional Fees for PCT/US2012/030349, mailed on Jul. 24, 2012.
International Search Report and Written Opinion for PCT/US2012/030349, mailed on Oct. 5, 2012.
Office Action, mailed Mar. 25, 2011, for U.S. Appl. No. 11/453,222.
Office Action, mailed Oct. 18, 2011, for U.S. Appl. No. 11/453,222.
Office Action, mailed Apr. 11, 2013, for U.S. Appl. No. 11/453,222.
Office Action, mailed Oct. 3, 2013, for U.S. Appl. No. 11/453,222.
Office Communication mailed Jan. 26, 2007 for U.S. Appl. No. 10/446,444.
Office Communication mailed Oct. 3, 2007 for U.S. Appl. No. 10/446,444.
Notice of Allowance mailed May 21, 2008 for U.S. Appl. No. 10/446,444.
Office Communication mailed Apr. 6, 2010 for U.S. Appl. No. 12/568,481.
Office Communication, mailed Jun. 1, 2011, for U.S. Appl. No. 12/568,481.

(56) References Cited

OTHER PUBLICATIONS

Office Communication, mailed Oct. 7, 2011, for U.S. Appl. No. 12/568,481.
Notice of Allowance, mailed Mar. 26, 2012, for U.S. Appl. No. 12/568,481.
Office Communication, mailed Feb. 24, 2011, for U.S. Appl. No. 12/833,749.
Office Communication, mailed Sep. 14, 2011, for U.S. Appl. No. 12/833,749.
Advisory Action, mailed Jan. 6, 2012, for U.S. Appl. No. 12/833,749.
Office Communication, mailed Aug. 16, 2012, for U.S. Appl. No. 12/530,330.
Office Communication mailed May 20, 2003 for U.S. Appl. No. 09/969,431.
Office Communication mailed Oct. 2, 2003 for U.S. Appl. No. 09/969,431.
Office Communication mailed May 13, 2004 for U.S. Appl. No. 09/969,431.
Notice of Allowance mailed Nov. 18, 2004 for U.S. Appl. No. 09/969,431.
Office Communication, mailed Jul. 9, 2009 for U.S. Appl. No. 11/099,886.
Office Action, mailed Jan. 22, 2010, for U.S. Appl. No. 11/099,886.
Office Communication, mailed Feb. 23, 2011, for U.S. Appl. No. 11/099,886.
Office Communication, mailed Aug. 1, 2011, for U.S. Appl. No. 11/099,886.
Notice of Allowance, mailed Jun. 7, 2013, for U.S. Appl. No. 11/099,886.
Office Communication, mailed Oct. 13, 2011, for U.S. Appl. No. 12/507,999.
Office Communication, mailed Feb. 24, 2012, for U.S. Appl. No. 12/507,999.
Notice of Allowance, mailed May 30, 2012, for U.S. Appl. No. 12/507,999.
Office Communication, mailed May 9, 2012, for U.S. Appl. No. 13/301,315.
Office Communication, mailed Sep. 19, 2012, for U.S. Appl. No. 13/301,315.
Office Communication, mailed Jan. 10, 2011, for U.S. Appl. No. 11/780,754.
Office Communication, mailed Jul. 7, 2011, for U.S. Appl. No. 11/780,754.
Notice of Allowance, mailed Aug. 1, 2011, for U.S. Appl. No. 11/780,754.
Office Communication, mailed Nov. 6, 2012, for U.S. Appl. No. 13/312,224.
Office Communication, mailed Mar. 1, 2013, for U.S. Appl. No. 13/312,224.
Notice of Allowance, mailed Jun. 11, 2013, for U.S. Appl. No. 13/312,224.
Notice of Allowance, mailed Jun. 13, 2013, for U.S. Appl. No. 13/312,224.
Office Communication mailed Dec. 4, 2009 for U.S. Appl. No. 11/758,078.
Office Action, mailed Jun. 24, 2010, for U.S. Appl. No. 11/758,078.
Office Action, mailed Jun. 13, 2011, for U.S. Appl. No. 12/716,732.
Office Action, mailed Dec. 16, 2011, for U.S. Appl. No. 12/716,732.
Office Action, mailed Apr. 4, 2012, for U.S. Appl. No. 12/716,732.
Office Action, mailed Sep. 28, 2012, for U.S. Appl. No. 12/716,732.
Notice of Allowance, mailed Feb. 1, 2013, for U.S. Appl. No. 12/716,732.
Office Action, mailed Sep. 6, 2013, for U.S. Appl. No. 13/128,020.
Adami et al., An amino acid-based amphoteric liposomal delivery system for systemic administration of siRNA. Mol Ther. Jun. 2011;19(6):1141-51.
Akinc et al., A combinatorial library of lipid-like materials for delivery of RNAi therapeutics. Nat Biotech. 2008;26(5):561-69.
Akinc et al., Exploring polyethylenimine-mediated DNA transfection and the proton sponge hypothesis. J Gene Med. May 2005;7(5):657-63.
Akinc et al., Measuring the pH environment of DNA delivered using nonviral vectors: implications for lysosomal trafficking. Biotechnol Bioeng. Jun. 5, 2002;78(5):503-8.
Akinc et al., Parallel synthesis and biophysical characterization of a degradable polymer library for gene delivery. J Am Chem Soc. May 7, 2003;125(18):5316-23.
Akira et al., Functions of toll-like receptors: lessons from KO mice. C R Biol. Jun. 2004;327(6):581-9.
Ali et al., Derivation of type II alveolar epithelial cells from murine embryonic stem cells. Tissue Eng. Aug. 2002;8(4):541-50.
Allison, The mode of action of immunological adjuvants. Dev Biol Stand. 1998;92:3-11.
Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.
Anderson et al., A polymer library approach to suicide gene therapy for cancer. Proc Natl Acad Sci USA. Nov. 9, 2004;101(45):16028-33. Epub Nov. 1, 2004.
Anderson et al., Biodegradation and biocompatibility of PLA and PLGA microspheres. Adv Drug Deliv Rev. Oct. 13, 1997;28(1):5-24.
Anderson et al., Nanoliter-scale synthesis of arrayed biomaterials and application to human embryonic stem cells. Nat Biotechnol. Jul. 2004;22(7):863-6. Epub Jun. 13, 2004.
Anderson et al., Semi-automated synthesis and screening of a large library of degradable cationic polymers for gene delivery. Angew Chem Int Ed Engl. Jul. 14, 2003;42(27):3153-8.
Anderson et al., Structure/property studies of polymeric gene delivery using a library of poly(beta-amino esters). Mol Ther. Mar. 2005;11(3):426-34.
Anderson, Biological Responses to Materials. Annu Rev Mater Res. 2001;31:81-110.
Anderson, Chapter 4. Mechanisms of Inflammation and Infection With Implanted Devices. Cardiovasc Pathol. 1993;2:33S-41S.
Anderson, Human gene therapy. Nature. Apr. 30, 1998;392(6679 Suppl):25-30. Review.
Ando et al., PLGA microspheres containing plasmid DNA: preservation of supercoiled DNA via cryopreparation and carbohydrate stabilization. J Pharm Sci. Jan. 1999;88(1):126-30.
Angeloni et al., Liquid crystalline poly (β-aminoester)s containing different mesogenic groups. Makromlekulare Chemie. 1985;186:977-97.
Anseth et al., In situ forming degradable networks and their application in tissue engineering and drug delivery. J Control Release. Jan. 17, 2002;78(1-3):199-209.
Anseth et al., New Directions in Photopolymerizable Biomaterials. Mrs Bull. 2002;27:130-136.
Anseth et al., Photopolymerizable degradable polyanhydrides with osteocompatibility. Nat Biotechnol. Feb. 1999;17(2):156-9.
Anseth et al., Polymeric Dental Composites: Properties and Reaction Behavior of Multimethacrylate Dental Restorations. Advances in Polymer Science. 1995;122:177-217.
Astle et al., A VEGFR2 Antagonist and Other Peptoids Evade Immune Recognition. Int J Pept Res Ther. 2008;14(3):223-227.
Bajaj et al., Synthesis and gene transfection efficacies of PEI-cholesterol-based lipopolymers. Bioconjug Chem. Aug. 2008;19(8):1640-51. Epub Jul. 11, 2008.
Ballermann et al., Shear stress and the endothelium. Kidney Int Suppl. Sep. 1998;67:S100-8.
Barbucci et al. Macroinorganics. 7. Property-Structure Relationships for Polymeric Bases Whose Monomeric Units Behave Independently towards Protonation. Macromolecules 1981;14:1203-09.
Barbucci et al., Protonation studies of multifunctional polymers with a poly(amido-amine) structure. Polymer. 1978;19:1329-34.
Barbucci et al., Thermodynamic ad 13C n.m.r data on the protonation of polymeric bases whose repeating units behave independently towards protonation. Polymer. 1980;21:81-85.
Barrera et al., Synthesis and RGD Peptide Modification of a New Biodegradable Copolymer: Poly(lactic acid-co-lysine). J Am Chem Soc. 1993;115:11010-11.

(56) References Cited

OTHER PUBLICATIONS

Bartel, MicroRNAs: Genomics, Biogenesis, Mechanism, and Function. Cell. 2004;116:281-97.
Beebe et al., Microfluidic tectonics: a comprehensive construction platform for microfluidic systems. Proc Natl Acad Sci U S A. Dec. 5, 2000;97(25):13488-93.
Behr, Synthetic gene-transfer vectors. Acc Chem Res. 1993;26:274-278.
Behr, The Proton Sponge: a Trick to Enter Cells the Viruses Did Not Exploit. Chimia. 1997;51:34-36.
Benns et al., pH-sensitive cationic polymer gene delivery vehicle: N-Ac-poly(L-histidine)-graft-poly(L-lysine) comb shaped polymer. Bioconjug Chem. Sep.-Oct. 2000;11(5):637-45.
Berge et al., Pharmaceutical salts. J Pharm Sci. Jan. 1977;66(1):1-19.
Bossle et al., Synthesis and biological activity of new 2-substituted analogs of fluphenazine. J Med Chem. Mar. 1, 1976;19(3):370-3.
Boudou et al., Multiple functionalities of polyelectrolyte multilayer films: new biomedical applications. Adv Mater. Jan. 26, 2010;22(4):441-67.
Boussif et al., A versatile vector for gene and oligonucleotide transfer into cells in culture and in vivo: polyethylenimine. Proc Natl Acad Sci U S A. Aug. 1, 1995;92(16):7297-301.
Bratlie et al., Rapid biocompatibility analysis of materials via in vivo fluorescence imaging of mouse models. PLoS One. Apr. 6, 2010;5(4):e10032.
Braun et al., Structure/function relationships of polyamidoamine/DNA dendrimers as gene delivery vehicles. J Pharm Sci. Feb. 2005;94(2):423-36.
Brazeau et al., In vitro myotoxicity of selected cationic macromolecules used in non-viral gene delivery. Pharm Res. May 1998;15(5):680-4.
Breunig et al., Breaking up the correlation between efficacy and toxicity for nonviral gene delivery. Proc Natl Acad Sci U S A. Sep. 4, 2007;104(36):14454-9. Epub Aug. 28, 2007.
Breunig et al., Mechanistic investigation of poly(ethylene imine)-based siRNA delivery: disulfide bonds boost intracellular release of the cargo. J Control Release. Aug. 25, 2008;130(1):57-63. Epub May 24, 2008.
Brocchini et al., A Combinatorial Approach for Polymer Designs. J Am Chem Soc. 1997;119:4553-54.
Brocchini, Combinatorial chemistry and biomedical polymer development. Adv Drug Deliv Rev. Dec. 3, 2001;53(1):123-30.
Brodbeck et al., Biomaterial surface chemistry dictates adherent monocyte/macrophage cytokine expression in vitro. Cytokine. Jun. 21, 2002;18(6):311-9.
Bryant et al., Cytocompatibility of UV and visible light photoinitiating systems on cultured NIH/3T3 fibroblasts in vitro. J Biomater Sci Polym Ed. 2000;11(5):439-57.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9. Epub Aug. 22, 2005.
Byk et al., Synthesis, activity, and structure—activity relationship studies of novel cationic lipids for DNA transfer. J Med Chem. 1998;41(2):224-235.
Byloos et al., Phase Transitions of Alkanethiol Self-Assembled Monolayers at an Electrified Gold Surface. J Phys Chem B. 2001;105:5900-05.
Caminschi et al., Molecular cloning of F4/80-like-receptor, a seven-span membrane protein expressed differentially by dendritic cell and monocyte-macrophage subpopulations. J Immunol. Oct. 1, 2001;167(7):3570-6.
Campbell et al., Application of cytokeratin 7 and 20 immunohistochemistry to diagnostic pathology. Current Diagnostic Pathology. 2001;7:113-22.
Capan et al., Preparation and characterization of poly (D,L-lactide-co-glycolide) microspheres for controlled release of poly(L-lysine) complexed plasmid DNA. Pharm Res. Apr. 1999;16(4):509-13.

Carter et al., Mechanobiology of skeletal regeneration. Clin Orthop Relat Res. Oct. 1998;(355 Suppl):S41-55.
Casimiro et al., Vaccine-induced immunity in baboons by using DNA and replication-incompetent adenovirus type 5 vectors expressing a human immunodeficiency virus type 1 gag gene. J Virol. Jul. 2003;77(13):7663-8.
Chakraborty, Potentiality of Small Interfering RNAs (siRNA) as Recent Therapeutic Targets for Gene-Silencing. Curr Drug Targets. 2007;8:469-82.
Chan et al., Triplex DNA: fundamentals, advances, and potential applications for gene therapy. J Mol Med. Apr. 1997;75(4):267-82. Review.
Chang, Therapeutic applications of polymeric artificial cells. Nat Rev Drug Discov. Mar. 2005;4(3):221-35.
Chen et al., Polymeric growth factor delivery strategies for tissue engineering. Pharm Res. Aug. 2003;20(8):1103-12.
Cho et al., A proposed mechanism for the induction of cytotoxic T lymphocyte production by heat shock fusion proteins. Immunity. Mar. 2000;12(3):263-72.
Cho et al., Homeostasis-stimulated proliferation drives cotton T cells to differentiate directly into memory T cells. J Exp Med. Aug. 21, 2000;192(4):549-56.
Choksakulnimitr et al., In vitro cytotoxicity of macromolecules in different cell culture systems. J Control Rel. 1995;34:233-41.
Chu et al., Cytokeratin 7 and cytokeratin 20 expression in epithelial neoplasms: a survey of 435 cases. Mod Pathol. Sep. 2000;13(9):962-72.
Conley et al., Derivation, propagation and differentiation of human embryonic stem cells. Int J Biochem Cell Biol. Apr. 2004;36(4):555-67.
Cotten et al., Receptor-mediated transport of DNA into eukaryotic cells. Methods Enzymol. 1993;217:618-44.
Creusat et al., Proton sponge trick for pH-sensitive disassembly of polyethylenimine-based siRNA delivery systems. Bioconjug Chem. May 19, 2010;21(5):994-1002.
Cristofaro et al., Role of Toll-like receptors in infection and immunity: clinical implications. Drugs. 2006;66(1):15-29.
Crooke, Evaluating the mechanism of action of antiproliferative antisense drugs. Antisense Nucleic Acid Drug Dev. Apr. 2000;10(2):123-6.
Crooke, Molecular mechanisms of action of antisense drugs. Biochim Biophys Acta. Dec. 10, 1999;1489(1):31-44. Review.
Crystal, Transfer of genes to humans: early lessons and obstacles to success. Science. Oct. 20, 1995;270(5235):404-10. Review.
Danusso et al., Nuovi alti polimeri da poliaddizione di piperazina o 2-metilpiperazina a diesteri acrilici o divinilsolfone. Chim Ind (Milan). 1967;49:826-30. Italian.
Danusso et al., Synthesis of tertiary amine polymers. Polymer. 1970;11:88-113.
Davis et al., Evidence of RNAi in humans from systemically administered siRNA via targeted nanoparticles. Nature. Apr. 15, 2010;464(7291):1067-70. Epub Mar. 21, 2010.
De Smedt et al., Cationic polymer based gene delivery systems. Pharm Res. Feb. 2000;17(2):113-26.
Decher, Fuzzy Nanoassemblies: Toward Layered Polymeric Multicomposites. Science. 1997;277;1232-37.
Demeneix et al., Chapter 14. The Proton Sponge: A Trick the Viruses Did Not Exploit. Artificial Self Assembly Systems for Gene Delivery (Felgner et al Eds). 1996:146-51.
Dern et al., Toxicity studies of pyrimethamine (daraprim). Am J Trop Med Hyg. Mar. 1955;4(2):217-20.
Deshmukh et al., Liposome and polylysine mediated gene therapy. New J Chem. 1997;21:113-124.
Diebold et al., Innate antiviral responses by means of TLR7-mediated recognition of single-stranded RNA. Science. Mar. 5, 2004;303(5663):1529-31. Epub Feb. 19, 2004.
Discher et al., Polymer vesicles. Science. Aug. 9, 2002;297(5583):967-73. Review.
Discher et al., Polymersomes: tough vesicles made from diblock copolymers. Science. May 14, 1999;284(5417):1143-6.
Dushnik-Levinson et al., Embryogenesis in vitro: study of differentiation of embryonic stem cells. Biol Neonate. 1995;67(2):77-83.

(56) References Cited

OTHER PUBLICATIONS

Eddington et al., Flow control with hydrogels. Adv Drug Deliv Rev. Feb. 10, 2004;56(2):199-210.
Elbashir et al., RNA interference is mediated by 21- and 22-nucleotide RNAs. Genes Dev. 2001;15:188-200.
Elisseeff et al., Transdermal photopolymerization for minimally invasive implantation. Proc Natl Acad Sci U S A. Mar. 16, 1999;96(6):3104-7.
Ewert et al., Cationic lipid-DNA complexes for gene therapy: understanding the relationship between complex structure and gene delivery pathways at the molecular level. Curr Med Chem. Jan. 2004;11(2):133-49.
Ferruti et al., A novel modification of poly(l-lysine) leading to a soluble cationic polymer with reduced toxicity and with potential as a transfection agent. Macromol Chem Phys 1998;199:256-575.
Ferruti et al., Linear Amino Polymers: Synthesis, Protonation and Complex Formation. Advances in Polymer Sci. 1984;58:55-92.
Ferruti et al., Recent results on functional polymers and macromonomers of interest as biomaterials or for biomaterial modification. Biomaterials. Dec. 1994;15(15):1235-41.
Ferruti et al., Synthesis, characterisation and antitumour activity of platinum (II) complexes of novel functionalised poly(amido amine)s. Macromol Chem Phys. 1999;200:1644-54.
Ferruti et al., Synthesis, physico-chemical properties and biomedical applications of poly(amido-amine)s. Polymyer. 1985;26:1336-48.
Field et al., A simple predictive model for spherical indentation. J Mater Res. 1993;8(2):297-306.
Fire et al., Potent and specific genetic interference by double-stranded RNA in Caenorhabditis elegans. Nature. Feb. 19, 1998;391(6669):806-11.
Fisher et al., Photoinitiated Polymerization of Biomaterials. Annu Rev Mater Res. 2001;31:171-81.
Fisher et al., Synthesis and properties of photocross-linked poly(propylene fumarate) scaffolds. J Biomater Sci Polym Ed. 2001;12(6):673-87.
Flory et al., Principles of Polymer Chemistry. Cornell University Press. Ithaca, New York. 1953:40-46, 318-23.
Fominaya et al., Target cell-specific DNA transfer mediated by a chimeric multidomain protein. Novel non-viral gene delivery system. J Biol Chem. May 3, 1996;271(18):10560-8.
Forsbach et al., Identification of RNA sequence motifs stimulating sequence-specific TLR8-dependent immune responses. J Immunol. Mar. 15, 2008;180(6):3729-38.
Friedmann, Human gene therapy—an immature genie, but certainly out of the bottle. Nat Med. Feb. 1996;2(2):144-7.
Fritz et al., Gene transfer into mammalian cells using histone-condensed plasmid DNA. Hum Gene Ther. Aug 1, 1996;7(12):1395-404.
Fu et al., Visual Evidence of Acidic Environment Within Degrading Poly(lactic-co-glycolic acid) (PLGA) Microspheres. Pharma Res. 2000;17(1):100-06.
Furgeson et al., Modified linear polyethylenimine-cholesterol conjugates for DNA complexation. Bioconjug Chem. Jul.-Aug. 2003;14(4):840-7.
Furgeson et al., Novel water insoluble lipoparticulates for gene delivery. Pharm Res. Apr. 2002;19(4):382-90.
Gardner, Stem cells and regenerative medicine: principles, prospects and problems. C R Biol. Jun.-Jul. 2007;330(6-7):465-73. Epub Feb. 15, 2007.
Garg et al., Genetic tagging shows increased frequency and longevity of antigen-presenting, skin-derived dendritic cells in vivo. Nat Immunol. Sep. 2003;4(9):907-12. Epub Aug. 10, 2003. Corrigendum Nat Immunol Oct. 2003:4(10):1037.
Gebhart et al., Evaluation of polyplexes as gene transfer agents. J Control Release. Jun. 15, 2001;73(2-3):401-16.
Gerasimov et al., Cytosolic drug delivery using pH- and light-sensitive liposomes. Adv Drug Deliv Rev. Aug. 20, 1999;38(3):317-338.
Ghosh et al., Toll-like receptor (TLR) 2-9 agonists-induced cytokines and chemokines: I. Comparison with T cell receptor-induced responses. Cell Immunol. Sep. 2006;243(1):48-57. Epub Jan. 23, 2007.

Godbey et al., Size matters: molecular weight affects the efficiency of poly(ethylenimine) as a gene delivery vehicle. J Biomed Mater Res. Jun. 5, 1999;45(3):268-75.
Gonzalez et al., New class of polymers for the delivery of macromolecular therapeutics. Bioconjug Chem. Nov.-Dec. 1999;10(6):1068-74.
Grayson et al., Biophysical and structural characterization of polyethylenimine-mediated siRNA delivery in vitro. Pharm Res. Aug. 2006;23(8):1868-76.
Green et al., Biodegradable polymeric vectors for gene delivery to human endothelial cells. Bioconjug Chem. Sep.-Oct. 2006;17(5):1162-9.
Gross et al., Bioluminescence imaging of myeloperoxidase activity in vivo. Nat Med. Apr. 2009;15(4):455-61. Epub Mar. 22, 2009.
Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517-23.
Grzelinski et al., RNA interference-mediated gene silencing of pleiotrophin through polyethylenimine-complexed small interfering RNAs in vivo exerts antitumoral effects in glioblastoma xenografts. Hum Gene Ther. Jul. 2006;17(7):751-66.
Guan et al., Embryonic stem cell-derived neurogenesis. Retinoic acid induction and lineage selection of neuronal cells. Cell Tissue Res. Aug. 2001;305(2):171-6.
Guan et al., Surface photo-grafting of polyurethane with 2-hydroxyethyl acrylate for promotion of human endothelial cell adhesion and growth. J Biomater Sci Polym Ed. 2000;11(5):523-36.
Haensler et al., Polyamidoamine cascade polymers mediate efficient transfection of cells in culture. Bioconjug Chem. Sep.-Oct. 1993;4(5):372-9.
Hammond et al., An RNA-directed nuclease mediates post-transcriptional gene silencing in Drosophila cells. Nature. 2000;404:293-96.
Hanes et al., New advances in microsphere-based single-dose vaccines. Adv Drug Deliv Rev. Oct. 13, 1997;28(1):97-119.
Hansen et al., Re-examination and further development of a precise and rapid dye method for measuring cell growth/cell kill. J Immunol Methods. May 12, 1989;119(2):203-10.
Harder et al., Molecular Conformation in Oligo(ethylene glycol)—Terminated Self-Assembled Monolayers on Gold and Silver Surfaces Determines Their Ability to Resist Protein Adsorpotion. J Phys Chem B. 1998;102:426-36.
Hasan et al., Identification of cytokeratin 1 as a binding protein and presentation receptor for kininogens on endothelial cells. Proc Natl Acad Sci U S A. Mar. 31, 1998;95(7):3615-20.
Haugland, Handbook of Fluorescent Probes and Research Chemicals. 6th ed. Molecular Probes, Inc. 1996:29.
He et al., Experimental Investigation into One-Step and Two-Steps Polymerization Via Michael Addition from Primary Amine. Polymer Preprints. 2001;42(2):335-36.
Hedley et al., Microspheres containing plasmid-encoded antigens elicit cytotoxic T-cell responses. Nat Med. Mar. 1998;4(3):365-8.
Heil et al., Species-specific recognition of single-stranded RNA via toll-like receptor 7 and 8. Science. Mar. 5, 2004;303(5663):1526-9. Epub Feb. 19, 2004.
Hemmi et al., Small anti-viral compounds activate immune cells via the TLR7 MyD88-dependent signaling pathway. Nat Immunol. Feb. 2002;3(2):196-200. Epub Jan. 22, 2002.
Hill et al., Enantioselective Epoxidation of Allylic Alcohols: (2S,3S)-3-Propyloxiranemethanol Org Syn. 1990;7:461.
Hill et al., In vitro cytotoxicity of poly(amidoamine)s: relevance to DNA delivery. Biochim Biophys Acta. Apr. 19, 1999;1427(2):161-74.
Hoekenga, The treatment of malaria with hydroxychloroquine. Am J Trop Med Hyg. Mar. 1955;4(2): 221-3.
Hofland et al., Formation of stable cationic lipid/DNA complexes for gene transfer. Proc Natl Acad Sci USA. Jul. 9, 1996;93(14):7305-9.
Holmlin et al., Zwitterionic SAMs that Resist Nonspecific Adsorption of Protein from Aqueous Buffer. Langmuir. 2001;17:2841-50.
Hope et al., Cationic Lipids, Phosphatidylethanolamine and the Intracellular Delivery of Polymeric, Nucleic Acid-Based Drugs. Molecular Membrane Technology. 1998;15:1-14.

(56) References Cited

OTHER PUBLICATIONS

Hornung et al., Quantitative expression of toll-like receptor 1-10 mRNA in cellular subsets of human peripheral blood mononuclear cells and sensitivity to CpG oligodeoxynucleotides. J Immunol. May 1, 2002;168(9):4531-7.

Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.

Howard, Delivery of RNA interference therapeutics using polycation-based nanoparticles. Adv Drug Deliv Rev. Jul. 25, 2009;61(9):710-20. Epub Apr. 5, 2009.

Huang et al., Long-term in vivo gene expression via delivery of PEI-DNA condensates from porous polymer scaffolds. Hum Gene Ther. May 2005;16(5):609-17.

Hunt et al., Effect of biomaterial surface charge on the inflammatory response: evaluation of cellular infiltration and TNF alpha production. J Biomed Mater Res. May 1996;31(1):139-44.

Hutchison et al., Robust polymer microfluidic device fabrication via contact liquid photolithographic polymerization (CLiPP). Lab Chip. 2004;4:658-662.

Hwang et al., Effects of structure of beta-cyclodextrin-containing polymers on gene delivery. Bioconjug Chem. Mar.-Apr. 2001;12(2):280-90.

Ichimaru et al., Synthesis and characterization of new piperazine-type inhibitors for mitochondrial NADH-ubiquinone oxidoreductase (complex I). Biochemistry. Oct. 7, 2008;47(40):10816-26. Epub Sep. 10, 2008.

Incani et al., Lipid and hydrophobic modification of cationic carriers on route to superior gene vectors. Soft Matter. 2010;6:2124-38.

Ingber et al., Mechanochemical switching between growth and differentiation during fibroblast growth factor-stimulated angiogenesis in vitro: role of extracellular matrix. J Cell Biol. Jul. 1989;109(1):317-30.

Irwin et al., Modulus-dependent macrophage adhesion and behavior. J Biomater Sci Polym Ed. 2008;19(10):1363-82.

Ito, Surface micropatterning to regulate cell functions. Biomaterials. Dec. 1999;20(23-24):2333-42.

Itskovitz-Eldor et al., Differentiation of human embryonic stem cells into embryoid bodies compromising the three embryonic germ layers. Mol Med. Feb. 2000;6(2):88-95.

Iwasaki et al., Toll-like receptor control of the adaptive immune responses. Nat Immunol. Oct. 2004;5(10):987-95.

Jarrossay et al., Specialization and complementarity in microbial molecule recognition by human myeloid and plasmacytoid dendritic cells. Eur J Immunol. Nov. 2001;31(11):3388-93.

Jia et al., Demonstration of two novel methods for predicting functional siRNA efficiency. BMC Bioinformatics. 2006;7:271.

Jiang et al., Electrochemically controlled release of lipid/DNA complexes: a new tool for synthetic gene delivery system. Electrochem Commun. 2004;6:576-82.

Jiang et al., Hyaluronic acid-polyethyleneimine conjugate for target specific intracellular delivery of siRNA. Biopolymers. Jul. 2008;89(7):635-42.

Jiang et al., Ultralow-fouling, functionalizable, and hydrolyzable zwitterionic materials and their derivatives for biological applications. Adv Mater. Mar. 5, 2010;22(9):920-32.

Johansson et al., Evidence for involvement of activin A and bone morphogenetic protein 4 in mammalian mesoderm and hematopoietic development. Mol Cell Biol. Jan. 1995;15(1):141-51.

Jolck et al., Solid-phase synthesis of PEGylated lipopeptides using click chemistry. Bioconjug Chem. May 19, 2010;21(5):807-10.

Jon et al., Degradable poly(amino alcohol esters) as potential DNA vectors with low cytotoxicity. Biomacromolecules. Nov.-Dec. 2003;4(6):1759-62.

Judge et al., Design of noninflammatory synthetic siRNA mediating potent gene silencing in vivo. Mol Ther. Mar. 2006;13(3):494-505. Epub Dec. 15, 2005.

Kabanov et al., DNA complexes with polycations for the delivery of genetic material into cells. Bioconjug Chem. Jan.-Feb. 1995 Jan-Feb;6(1):7-20.

Kabanov, Taking polycation gene delivery systems from in vitro to in vivo. Pharm Sci Technolo Today. Sep. 1999;2(9):365-372.

Kamath et al., Surface chemistry influences implant-mediated host tissue responses. J Biomed Mater Res A. Sep. 2008;86(3):617-26.

Kargina et al., Self-Splitted Water-Soluble Ionogenic Polymers. Vysokomol Soedin Seriya. 1986;28:1139-44. Russian.

Katsuki et al., Chapter 1. Asymmetric Epoxidation of Allylic Alcohols: The Katsuki-Sharpless Epoxidation Reaction. Org React 1996;48:1-299.

Katsuki et al., The First Practical Method for Asymmetric Epoxidation. J Am Chem Soc. 1980:102;5974-76.

Kaufman et al., Hematopoietic colony-forming cells derived from human embryonic stem cells. Proc Natl Acad Sci U S A. Sep. 11, 2001;98(19):10716-21. Epub Sep. 4, 2001.

Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.

Kawata et al., Finer features for functional microdevices. Nature. Aug. 16, 2001;412(6848):697-8.

Kay et al., Viral vectors for gene therapy: the art of turning infectious agents into vehicles of therapeutics. Nat Med. Jan. 2001;7(1):33-40.

Khademhosseini et al., Molded polyethylene glycol microstructures for capturing cells within microfluidic channels. Lab Chip. Oct. 2004;4(5):425-30. Epub Jul. 26, 2004.

Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.

Kim et al., Efficient siRNA delivery using water soluble lipopolymer for anti-angiogenic gene therapy. J Control Release. Apr. 23, 2007;118(3):357-63. Epub Jan. 9, 2007.

Kim et al., Local and systemic delivery of VEGF siRNA using polyelectrolyte complex micelles for effective treatment of cancer. J Control Release. Jul. 14, 2008;129(2):107-16. Epub Mar. 14, 2008.

Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.

Kleinman et al., Sequence- and target-independent angiogenesis suppression by siRNA via TLR3. Nature. Apr. 3, 2008;452(7187):591-7. Epub Mar. 26, 2008.

Korshak et al., Water-soluble anion exchange resins based on methacrylic beta-aminoesters. Vysokomolekulyarnye Soedineniya, Seriya B: Kratkie Soobscheniya. 1975;17(5):401-04.

Krieg et al., CpG motifs in bacterial DNA trigger direct B-cell activation. Nature. Apr. 6, 1995;374(6522):546-9.

Krieg et al., Toll-like receptors 7, 8, and 9: linking innate immunity to autoimmunity. Immunol Rev. Dec. 2007;220:251-69.

Kukowska-Latallo et al., Efficient transfer of genetic material into mammalian cells using Starburst polyamidoamine dendrimers. Proc Natl Acad Sci USA. May 14, 1996;93(10):4897-902.

Kunath et al., Integrin targeting using RGD-PEI conjugates for in vitro gene transfer. J Gene Med. Jul. 2003;5(7):588-99.

Kursa et al., Novel shielded transferrin-polyethylene glycol-polyethylenimine/DNA complexes for systemic tumor-targeted gene transfer. Bioconjug Chem. Jan.-Feb. 2003;14(1):222-31.

Kwon et al., Application of an HIV gp41-derived peptide for enhanced intracellular trafficking of synthetic gene and siRNA delivery vehicles. Bioconjug Chem. Apr. 2008;19(4):920-7. Epub Apr. 1, 2008.

Kwon et al., Pseudopoly(amino acids): A Study of the Synthesis and Characterization of Poly(trans-4-hydroxy-N-acyl-1-proline esters). Macromolecules. 1989;22:3250-55.

Lan et al., Stabilized immune modulatory RNA compounds as agonists of Toll-like receptors 7 and 8. Proc Natl Acad Sci U S A. Aug. 21, 2007;104(34):13750-5. Epub Aug. 14, 2007.

Langer, Perspectives and challenges in tissue engineering and regenerative medicine. Adv Mater. Sep. 4, 2009;21(32-33):3235-6.

Leach et al., Bone engineering by controlled delivery of osteoinductive molecules and cells. Expert Opin Biol Ther. Jul. 2004;4(7):1015-27.

(56) References Cited

OTHER PUBLICATIONS

Leach et al., Photocrosslinked hyaluronic acid hydrogels: natural, biodegradable tissue engineering scaffolds. Biotechnology and Bioengineering. 2003;82:578-589.
Ledley, Nonviral gene therapy: the promise of genes as pharmaceutical products. Hum Gene Ther. Sep. 1995;6(9):1129-44.
Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.
Levenberg et al., Differentiation of human embryonic stem cells on three-dimensional polymer scaffolds. Proc Natl Acad Sci U S A. Oct. 28, 2003;100(22):12741-6. Epub Oct. 15, 2003.
Li et al., Defining the optimal parameters for hairpin-based knockdown constructs. RNA. 2007;13:1765-74.
Li et al., Plasticity of the urothelial phenotype: effects of gastrointestinal mesenchyme/stroma and implications for urinary tract reconstruction. Differentiation. Oct. 2000;66(2-3):126-35.
Li et al., Reverse Atom Transfer Radical Polymerization in Miniemulsion. Macromolecules. 2003;36(16):6028-6035.
Lim et al., Biodegradable, endosome disruptive, and cationic network-type polymer as a highly efficient and nontoxic gene delivery carrier. Bioconjug Chem. Sep.-Oct. 2002;13(5):952-7.
Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.
Lim et al., Development of a Safe Gene Delivery System Using Biodegradable Polymer, Poly[$\alpha$-(4-aminobutyl)-l-glycolic acid].J Am Chem Soc. 2000;122:6524-25.
Lim et al., Self-assembled ternary complex of cationic dendrimer, cucurbituril, and DNA: noncovalent strategy in developing a gene delivery carrier. Bioconjug Chem. Nov.-Dec. 2002;13(6):1181-5.
Lim, et al., A self-destroying polycationic polymer: biodegradable poly(4-hydroxy-l-proline ester. J. Am. Chem. Soc. 1999;121:5633-5639.
Linhardt et al., Free-Radical Synthesis of Poly(2-ethylacrylic acid) Fractions of Low Polydispersity: Effects of Molecular Weight and Polydispersity on the pH-Dependent Conformational Transition in Aqueous Solutions. Macromolecules. 1999;32:4457-59.
Linhardt et al., pH-Induced Fusion and Lysis of Phosphatidylcholine Vesicles by the Hydrophobic Polyelectrolyte Poly(2-ethylacrylic Acid). Langmuir. 2000;16:122-27.
Liu et al., Three-dimensional photopatterning of hydrogels containing living cells. Biomedical Microdevices. 2002;4:257-266.
Loan et al., Oligoamidoamines and oligoesteramines based on antibiotics containing $\beta$-lactam ring. Euro Poly J. 1996;32:957-62.
Loan et al., Poly(amdio amine)s and poly(ester amine)s based on aromatic amines containg carboxyl groups. Macromolecular Chem and Phys. 1995;11:3525-33.
Love et al., Lipid-like materials for low-dose, in vivo gene silencing. Proc Natl Acad Sci U S A. Feb. 2, 2010;107(5):1864-9. Epub Jan. 11, 2010.
Lukyanov et al., Micelles from lipid derivatives of water-soluble polymers as delivery systems for poorly soluble drugs. Adv Drug Deliv Rev. May 7, 2004;56(9):1273-89.
Luman et al., The convergent synthesis of poly(glycerol-succinic acid) dendritic macromolecules. Chemistry. Nov. 21, 2003;9(22):5618-26.
Luo et al., Synthetic DNA delivery systems. Nat Biotechnol. Jan. 2000;18(1):33-7. Review.
Lyle et al., Cytokeratin 15 (K15) as an Epithelial Stem Cell Marker: Implications for Aging and Carcinogenesis. J Invest Derma. 1999;112(4):623. Abstract #606.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable poly ($\beta$-amino eaters): synthesis, characterization, and self-assembly with plasmid DNA. J Am Chem Soc. 2000;122:10761-68.
Lynn et al., pH-Responsive Polymer Microspheres: Rapid Release of Encapsulated Material within the Range of Intracellular pH. Angew Chem Int Ed Engl. May 4, 2001;40(9):1707-1710.
Ma et al., Development of Cationic Polymer Coatings to Regulate Foreign Body Responses. Adv Mater. 2011;23:H189-94.
MacBeath et al., Printing proteins as microarrays for high-throughput function determination. Science. Sep. 8, 2000;289(5485):1760-3.
MacBeath et al., Printing Small Molecules as Microarrays and Detecting Protein-Ligand Interactions en Masse. J Am Chem Soc. 1999;121:7967-68.
Mann et al., Smooth muscle cell growth in photopolymerized hydrogels with cell adhesive and proteolytically degradable domains: synthetic ECM analogs for tissue engineering. Biomaterials. Nov. 2001;22(22):3045-51.
Marques et al., Activation of the mammalian immune system by siRNAs. Nat Biotechnol. Nov. 2005;23(11):1399-405.
Marshak-Rothstein, Toll-like receptors in systemic autoimmune disease. Nat Rev Immunol. Nov. 2006;6(11):823-35.
Martell et al., The Preparation and the Properties of Some N,N'-Disubstituted-ethylenediaminedipropionic Acids. J Am Chem Soc. 1950;72:5357-61.
Maruo et al., Three-dimensional microfabrication with two-photon-absorbed photopolymerization. Opt Lett. Jan. 15, 1997;22(2):132-4.
Mathiowitz et al., Novel microcapsules for delivery systems. Reactive Polymers. 1987;6:275-283.
Mathiowitz et al., Polyanhydride microspheres as drug carriers I. Hot-melt microencapsulation. J Control Release. 1987;5:13-22.
Mathiowitz et al., Polyanhydride Microspheres as Drug Carriers. II. Microencapsulation by Solvent Removal. J Appl Polymer Sci. 1988;35:755-774.
Mattey et al., Demonstration of cytokeratin in endothelial cells of the synovial microvasculature in situ and in vitro. Br J Rheumatol. Aug. 1993;32(8):676-82.
Mendelsohn et al., Rational design of cytophilic and cytophobic polyelectrolyte multilayer thin films. Biomacromolecules. Jan.-Feb. 2003;4(1):96-106.
Merdan et al., Prospects for cationic polymers in gene and oligonucleotide therapy against cancer. Adv Drug Deliv Rev. Sep. 13, 2002;54(5):715-58.
Midoux et al., Efficient gene transfer by histidylated polylysine/pDNA complexes. Bioconjug Chem. May-Jun. 1999;10(3):406-11.
Miller, Cationic Liposomes for Gene Therapy. Angew. Chem. Int. Ed. 1998;37:1769-1785.
Mintzer et al., Nonviral vectors for gene delivery. Chem Rev. Feb. 2009;109(2):259-302.
Moll et al., The human keratins: biology and pathology. Histochem Cell Biol. Jun. 2008;129(6):705-33. Epub May 7, 2008.
Moll, [Cytokeratins as markers of differentiation. Expression profiles in epithelia and epithelial tumors] Veroff Pathol. 1993;142:1-197. German.
Morris et al., Lentiviral-mediated delivery of siRNAs for antiviral therapy. Gene Ther. 2006;13:553-58.
Morrissey et al., Potent and persistent in vivo anti-HBV activity of chemically modified siRNAs. Nat Biotechnol. Aug. 2005;23(8):1002-7. Epub Jul. 24, 2005.
Mulligan, The basic science of gene therapy. Science. May 14, 1993;260(5110):926-32. Review.
Murphy et al., A combinatorial approach to the discovery of efficient cationic peptoid reagents for gene delivery. Proc Natl Acad Sci U S A. Feb. 17, 1998;95(4):1517-22.
Nahrendorf et al., Dual channel optical tomographic imaging of leukocyte recruitment and protease activity in the healing myocardial infarct. Circ Res. Apr. 27, 2007;100(8):1218-25. Epub Mar. 22, 2007.
Naito et al., siVirus: web-based antiviral siRNA design software for highly divergent viral sequences. Nucleic Acids Res. 2006;34:W448-450.
Narang et al., Cationic lipids with increased DNA binding affinity for nonviral gene transfer in dividing and nondividing cells. Bioconjug Chem. Jan.-Feb. 2005;16(1):156-68.
Navarro et al., Phospholipid—polyethylenimine conjugate-based micelle-like nanoparticles for siRNA delivery. Drug Deliv and Trans Res. 2011; 25-33.

(56) References Cited

OTHER PUBLICATIONS

Neamnark et al., Aliphatic lipid substitution on 2 kDa polyethylenimine improves plasmid delivery and transgene expression. Mol Pharm. Nov.-Dec. 2009;6(6):1798-815.

Nguyen et al., A novel high-throughput cell-based method for integrated quantification of type I interferons and in vitro screening of immunostimulatory RNA drug delivery. Biotechnol Bioeng. Jul. 1, 2009;103(4):664-75.

Nguyen et al., Drug delivery-mediated control of RNA immunostimulation. Mol Ther. Sep. 2009;17(9):1555-62. Epub Jul. 7, 2009.

Nguyen et al., Photopolymerizable hydrogels for tissue engineering applications. Biomaterials. Nov. 2002;23(22):4307-14.

Novak et al., Biomimetic strategies based on viruses and bacteria for the development of immune evasive biomaterials. Biomaterials. Apr. 2009;30(11):1989-2005. Epub Jan. 29, 2009.

Novina et al., The RNAi revolution. Nature. 2004;430:161-64.

O'Donnell et al., Preparation of microspheres by the solvent evaporation technique. Adv Drug Delivery Rev. 1997;28:25-42.

O'Hagan et al., Induction of potent immune responses by cationic microparticles with adsorbed human immunodeficiency virus DNA vaccines. J Virol. Oct. 2001;75(19):9037-43.

Odian et al., Step Polymerization. In: Principles of Polymerization. John Wiley & Sons, Inc. New York. 1991:73-89.

Odorico et al., Multilineage differentiation from human embryonic stem cell lines. Stem Cells. 2001;19(3):193-204.

Ogris et al., Tumor-targeted gene therapy: strategies for the preparation of ligand-polyethylene glycol-polyethylenimine/DNA complexes. J Control Release. Aug. 28, 2003;91(1-2):173-81.

Okada, One- and three-month release injectable microspheres of the LH-RH superagonist leuprorelin acetate. Adv Drug Deliv Rev. Oct. 13, 1997;28(1):43-70.

Onuki et al., A review of the biocompatibility of implantable devices: current challenges to overcome foreign body response. J Diabetes Sci Technol. Nov. 2008;2(6):1003-15.

Orive et al., Cell encapsulation: promise and progress. Nat Med. Jan. 2003;9(1):104-7.

Ostuni et al., A Survey of Structure-Property Relationships of Surfaces that Resist the Adsorption of Protein. Langmuir. 2001;17:5605-20.

Pack et al., Design and development of polymers for gene delivery. Nat Rev Drug Discov. Jul. 2005;4(7):581-93.

Pack et al., Design of imidazole-containing endosomolytic biopolymers for gene delivery. Biotechnol Bioeng. Jan. 20, 2000;67(2):217-23.

Parrish et al., Five- and six-membered ring opening of pyroglutamic diketopiperazine. J Org Chem. Mar. 22, 2002;67(6):1820-6.

Pashine et al., Targeting the innate immune response with improved vaccine adjuvants. Nat Med. Apr. 2005;11(4 Suppl):S63-8.

Paul et al., Topographical control of human macrophages by a regularly microstructured polyvinylidene fluoride surface. Biomaterials. Oct. 2008;29(30):4056-64. Epub Jul. 29, 2008.

Peer et al., Nanocarriers as an emerging platform for cancer therapy. Nat Nanotechnol. Dec. 2007;2(12):751-60.

Peppas et al., Hydrogels in Biology and Medicine: From Molecular Principles to Bionanotechnology. Mater. 2006;18:1345-60.

Pera et al., Human embryonic stem cells. J Cell Sci. Jan. 2000;113 (Pt 1):5-10.

Philipp et al., Hydrophobically modified oligoethylenimines as highly efficient transfection agents for siRNA delivery. Bioconjug Chem. Nov. 2009;20(11):2055-61.

Phillips et al., Enhanced antibody response to liposome-associated protein antigens: preferential stimulation of IgG2a/b production. Vaccine. 1992;10(3):151-8.

Prabha et al., Size-dependency of nanoparticle-mediated gene transfection: studies with fractionated nanoparticles. Int J Pharm. Sep. 5, 2002;244(1-2):105-15.

Prata et al., Lipophilic peptides for gene delivery. Bioconjug Chem. Feb. 2008;19(2):418-20.

Putnam et al., Poly(4-hydroxy-l-proline ester): Low-Temperature Polycondensation and Plasmid DNA Complexation. Macromolecules 1999;32:3658-62.

Putnam et al., Polymer-based gene delivery with low cytotoxicity by a unique balance of side-chain termini. Proc Natl Acad Sci U S A. Jan. 30, 2001;98(3):1200-5. Epub Jan. 23, 2001.

Putnam, Polymers for gene delivery across length scales. Nat Mater. Jun. 2006;5(6):439-51.

Rao et al., Poly(butanediol Spermate): A Hydrolytically Labile Polyester-Based Nitric Oxide Carrier. J Bioactive Compatible Polymers. 1999;14:54-63.

Ratner et al., Biomaterials: where we have been and where we are going. Annu Rev Biomed Eng. 2004;6:41-75.

Refai et al., Effect of titanium surface topography on macrophage activation and secretion of proinflammatory cytokines and chemokines. J Biomed Mater Res A. Aug. 1, 2004;70(2):194-205.

Remy et al., Gene transfer with lipospermines and polyethylenimines. Adv Drug Deliv Rev. Mar. 2, 1998;30(1-3):85-95.

Reynolds et al., Rational siRNA design for RNA interference. Nat Biotechnol. 2004;22(3):326-30.

Robbins et al., siRNA and innate immunity. Oligonucleotides. Jun. 2009;19(2):89-101.

Roberts et al., Preliminary biological evaluation of polyamidoamine (PAMAM) Starburst dendrimers. J Biomed Mater Res. Jan. 1996;30(1):53-65.

Ruoslahti, The RGD story: a personal account. Matrix Biol. Nov. 2003;22(6):459-65.

Ryng et al., Synthesis and Structure Elucidation of 5-Aminomethinimino-3-methyl-4-isoxazolecarboxylic Acid Phenylamides and Their Immunological Activity. Archiv der Pharmazie. Jan. 1, 1997;330(11):319-26.

Sahay et al., Endocytosis of nanomedicines. J Control Release. Aug. 3, 2010;145(3):182-95. Epub Mar. 10, 2010.

Sahoo et al., Residual polyvinyl alcohol associated with poly (D,L-lactide-co-glycolide) nanoparticles affects their physical properties and cellular uptake. J Control Release. Jul. 18, 2002;82(1):105-14.

Sakiyama-Elbert et al., Functional Biomaterials: Design of Novel Biomaterials. Ann Rev Mater Res. 2001;31:183-201.

Saltzman, Chapter 19. Cell Interactions with Polymers. In: Principles of Tissue Engineering, 2d ed., 2000:221-35.

Sanford, The biolistic process. Trends Biotechnol. 1988;6:299-302.

Sawaf et al., [Cytokeratins, markers of epithelial cell differentiation: expression in normal epithelia.] Pathol Biol (Paris). 1992;40:655-65. French.

Schaffer et al., Vector unpacking as a potential barrier for receptor-mediated polyplex gene delivery. Biotechnol Bioeng. Mar. 5, 2000;67(5):598-606.

Schaus et al., Highly Selective Hydrolytic Kinetic Resolution of Terminal Epoxides Catalyzed by Chiral (salen)CoIII Complexes. Practical Synthesis of Enantioenriched Terminal Epoxides and 1,2-Biols. J Am Chem Soc. 2002;124(7):1307-15.

Scheel et al., Therapeutic anti-tumor immunity triggered by injections of immunostimulating single-stranded RNA. Eur J Immunol. Oct. 2006;36(10):2807-16.

Schena et al., Quantitative monitoring of gene expression patterns with a complementary DNA microarray. Science. Oct. 20, 1995;270(5235):467-70.

Schön et al.. TLR7 and TLR8 as targets in cancer therapy. Oncogene. Jan. 7, 2008;27(2):190-9.

Schuldiner et al., Effects of eight growth factors on the differentiation of cells derived from human embryonic stem cells. Proc Natl Acad Sci U S A. Oct. 10, 2000;97(21):11307-12.

Schutte et al., Cytokine profiling using monocytes/macrophages cultured on common biomaterials with a range of surface chemistries. J Biomed Mater Res A. Jan. 2009;88(1):128-39.

Schwartz et al., Peptide-mediated cellular delivery. Curr Opin Mol Ther. Apr. 2000;2(2):162-7.

Schweikl et al., Triethylene glycol dimethacrylate induces large deletions in the hprt gene of V79 cells. Mutat Res. Jan. 2, 1999;438(1):71-8.

Schweizer et al., Synthetic Studies towards the Total Synthesis of Providencin. Synthesis. 2007;24:3807-14.

(56) References Cited

OTHER PUBLICATIONS

Shchori, Poly(secondary Amine)s from Diacrylates and Diamines. J Polym Sci Polymer. 1983;21:413-15.
Singh et al., Cationic microparticles: A potent delivery system for DNA vaccines. Proc Natl Acad Sci U S A. Jan. 18, 2000;97(2):811-6.
Sioud, Induction of inflammatory cytokines and interferon responses by double-stranded and single-stranded siRNAs is sequence-dependent and requires endosomal localization. J Mol Biol. May 20, 2005;348(5):1079-90. Epub Mar. 22, 2005.
Sioud, Single-stranded small interfering RNA are more immunostimulatory than their double-stranded counterparts: a central role for 2'-hydroxyl uridines in immune responses. Eur J Immunol. May 2006;36(5):1222-30.
Smeds et al., Photocrosslinkable polysaccharides for in situ hydrogel formation. J Biomed Mater Res. Jan. 2001;54(1):115-21.
Somia et al., Gene therapy: trials and tribulations. Nat Rev Genet. Nov. 2000;1(2):91-9.
Spradling et al., Stem cells find their niche. Nature. Nov. 1, 2001;414(6859):98-104.
Steinman et al., Taking dendritic cells into medicine. Nature. Sep. 27, 2007;449(7161):419-26.
Stocum, Stem cells in regenerative biology and medicine. Wound Repair Regen. Nov.-Dec. 2001;9(6):429-42.
Streuli, Extracellular matrix remodeling and cellular differentiation. Curr Opin Cell Biol. 1999;11:634-40.
Strong et al., A General Synthetic Route to Defined, Biologically Active Multivalent Arrays. J Am Chem Soc. 1999;121:6193-96.
Suh et al., An angiogenic, endothelial-cell-targeted polymeric gene carrier. Mol Ther. Nov. 2002;6(5):664-72.
Suh et al., Ionization of Poly(ethylenimine) and Poly(allylamine) at Various PHS. Bioorg Chem. 1994;22:318-27.
Sullivan et al., Development of a novel gene delivery scaffold utilizing colloidal gold-polyethylenimine conjugates for DNA condensation. Gene Therapy. 2003;10:1882-90.
Swali et al., Solid-Phase Dendrimer Synthesis and the Generation of Super-High-Loading Resin Beads for Combinatorial Chemistry. J Org Chem Am Chem Soc. 1997;62:4902-03.
Szoka et al., Comparative properties and methods of preparation of lipid vesicles (liposomes). Annu Rev Biophys Bioeng. 1980;9:467-508.
Tabara et al., The rde-1 Gene, RNA Interference, and Transposon Silencing in C. elegans. Cell. 1999;99:123-32.
Tang et al., In vitro gene delivery by degraded polyamidoamine dendrimers. Bioconjug Chem. Nov.-Dec. 1996;7(6):703-14.
Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.
Thomas et al., Non-viral gene therapy: polycation-mediated DNA delivery. Appl Microbiol Biotechnol. Jul. 2003;62(1):27-34. Epub Apr. 29, 2003.
Thompson et al., Antiamebic action of 5-chloro-7-diethylaminomethyl-8-quinolinol and of other substituted 8-quinolinols in vitro and in experimental animals. Am J Trop Med Hyg. Mar. 1955;4(2):224-48.
Thomson et al., Embryonic stem cell lines derived from human blastocysts. Science. Nov. 6, 1998;282(5391):1145-7.
Tosatti et al., RGD-containing peptide GCRGYGRGDSPG reduces enhancement of osteoblast differentiation by poly(L-lysine)-graft-poly(ethylene glycol)-coated titanium surfaces. J Biomed Mater Res A. Mar. 1, 2004;68(3):458-72.
Tranchant et al., Physicochemical optimisation of plasmid delivery by cationic lipids. J Gene Med. Feb. 2004;6 Suppl 1:S24-35.
Trubetskoy et al., Recharging cationic DNA complexes with highly charged polyanions for in vitro and in vivo gene delivery. Gene Ther. Feb. 2003;10(3):261-71.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002;28(6):470-86.
Tweedie et al., Combinatorial material mechanics: high-throughput polymer synthesis and nanomechanical screening. Adv Mater. 2005;17:2599-2604.
Uhrich, Hyperbranched Polymers for Drug Discovery. Trends Polymer Sci. 1997;5:388-93.
Unal et al., Influence of filler addition on the mechanical properties of nylon-6 polymer. Journal of Reinforced Plastics and Composites. 2004;23(5):461-469.
Unkeless et al., Structure and function of human and murine receptors for IgG. Annu Rev Immunol. 1988;6:251-81.
Urban-Klein et al., RNAi-mediated gene-targeting through systemic application of polyethylenimine (PEI)-complexed siRNA in vivo. Gene Ther. Mar. 2005;12(5):461-6.
Van Balen et al., Liposome/water lipophilicity: methods, information content, and pharmaceutical applications. Med Res Rev. May 2004;24(3):299-324.
Van De Wetering et al., Structure-activity relationships of water-soluble cationic methacrylate/methacrylamide polymers for nonviral gene delivery. Bioconjug Chem. Jul.-Aug. 1999;10(4):589-97.
Vandenbroucke et al., Prolonged gene silencing in hepatoma cells and primary hepatocytes after small interfering RNA delivery with biodegradable poly(beta-amino esters). J Gene Med. Jul. 2008;10(7):783-94.
Vázquez et al., Construction of hydrolytically-degradable thin films via layer-by-layer deposition of degradable polyelectrolytes. J Am Chem Soc. Nov. 27, 2002;124(47):13992-3.
Von Harpe et al., Characterization of commercially available and synthesized polyethylenimines for gene delivery. J Control Release. Nov. 3, 2000;69(2):309-22.
Wagner et al., Influenza virus hemagglutinin HA-2 N-terminal fusogenic peptides augment gene transfer by transferrin-polylysine-DNA complexes: toward a synthetic virus-like gene-transfer vehicle. Proc Natl Acad Sci U S A. Sep. 1, 1992;89(17):7934-8.
Walde et al., Preparation of Vesicles (Liposomes). In: Encyclopedia of Nanoscience and Nanotechnology. Nalwa, ed. American Scientific Publishers: Los Angeles. 2004;9:43-79.
Walter et al., Microencapsulation of DNA using poly(DL-lactide-co-glycolide): stability issues and release characteristics. J Control Release. Sep. 20, 1999;61(3):361-74.
Wang et al, The functions of microRNAs in plants. Front Biosci. 2007;12:3975-82.
Wang et al., Mechanical and rheological properties of HDPE/graphite composite with enhanced thermal conductivity. Polymer Composites. 2001;22(1):97-103.
Ward, A Review of the Foreing-body Response to Subcutaneously-implanted Devices: The Role of Macrophages and Cytokines in Biofouling and Fibrosis. J Diabetes Sci Technol. 2008;2:768-77.
Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.
West et al., Photopolymerized hydrogel materials for drug delivery applications. Reactive Polymers. 1995; 25:139-147.
White et al., Poly(hydroxyaminoethers): A New Family of Epoxy-Based Thermoplastics. Adv Mater. 2000;12:1791-1800.
White et al., Step-growth polymerization of 10,11-epoxyundecanoic acid. Synthesis and properties of a new hydroxy-functionalized thermopastic polyester. Adv Mater. 2007;48:3990-98.
Whitehead et al., Knocking down barriers: advances in siRNA delivery. Nat Rev Drug Discov. Feb. 2009;8(2):129-38.
Wiethoff et al., Barriers to nonviral gene delivery. J Pharm Sci. Feb. 2003;92(2):203-17.
Wilen et al., Strategies in Optical Resolutions. Tetrahedron. 1977;33:2725-36.
Williams, On the mechanisms of biocompatibility. Biomaterials. Jul. 2008;29(20):2941-53. Epub Apr. 28, 2008.
Wintermantel et al., Blocked polyurethane prepolymers as component A in reactive adhesives. STN International HCAPLUS Database. 2006. Accession number: 2006:215601.
Wobus, Potential of embryonic stem cells. Mol Aspects Med. Jun. 2001;22(3):149-64.

(56) References Cited

OTHER PUBLICATIONS

Wu et al., Cationic lipid polymerization as a novel approach for constructing new DNA delivery agents. Bioconjug Chem. Mar.-Apr. 2001;12(2):251-7.
Yaffee et al., Serial passaging and differentiation of myogenic cells isolated from dystrophic mouse muscle. Nature. 1977;270:725-27.
Yang et al., A new approach to identifying genotoxic carcinogens: p53 induction as an indicator of genotoxic damage. Carcinogenesis. Jun. 1998;19(6):1117-25.
Yiu et al., Filtering of Ineffective siRNAs and Improved siRNA Design Tool. Bioinformatics. 2005;21(2):144-51.
Yoshioka et al., Epoxy-based Electroactive Polymer Gels. Experimental Mechanics. 2002;42:404-08.
Zamore et al., RNAi: Double-Stranded RNA Directs the ATP-Dependent Cleavage of mRNA at 21 to 23 Nucleotide Intervals. Cell. 2000;101:25-33.
Zaugg et al., 3-Carboxy-2,5-piperazinedione and Derivatives. J Amer Chem Soc. Jun. 5, 1956;78(11):2626-2631.
Zauner et al., Polylysine-based transfection systems utilizing receptor-mediated delivery. Adv Drug Deliv Rev. Mar. 2, 1998;30(1-3):97-113.
Zhang et al., Human Toll-like receptor-dependent induction of interferons in protective immunity to viruses. Immunol Rev. Dec. 2007;220:225-36.
Zhang et al., Structure/property relationships in erodible multilayered films: influence of polycation structure on erosion profiles and the release of anionic polyelectrolytes. Langmuir. Jan. 3, 2006;22(1):239-45.
Zhao et al., A developmental view of microRNA function. Trends Biochem. 2007;32(4):189-97.
Zhou et al., Preparation of Poly(l-serine ester): A Structural Analogue of Conventional Poly(l-serine). Macromolecules. 1990;23:3399-406.
Zintchenko et al., Simple modifications of branched PEI lead to highly efficient siRNA carriers with low toxicity. Bioconjug Chem. Jul. 2008;19(7):1448-55. Epub Jun. 14, 2008.
Zuber et al., Towards synthetic viruses. Adv Drug Deliv Rev. Nov. 19, 2001;52(3):245-53.
International Preliminary Report on Patentability for PCT/US2012/030349, mailed on Oct. 10, 2013.
Asokan et al., Cytosolic delivery of macromolecules. 3. Synthesis and characterization of acid-sensitive bis-detergents. Bioconjug Chem. Nov.-Dec. 2004;15(6):1166-73.
Conte et al., Regioselective ring opening of [(perfluoroalkyl)methyl] oxiranes with N-nucleophiles. J Fluorine Chem. 2005;126(9-10):1274-80.
Pollard et al., Ether amino alcohols. II. J Org Chem. 1952;17:1-3.
Partial Supplementary European Search Report for European Application No. 11820727.3, dated Nov. 26, 2014.
Invitation to Pay Additional Fees for PCT/US2004/016521, mailed Sep. 29, 2004.
International Search Report and Written Opinion for PCT/US2014/036355, mailed Aug. 5, 2014.
International Search Report and Written Opinion for PCT/US2014/044408, mailed Oct. 24, 2014.

Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Behr et al., Efficient gene transfer into mammalian primary endocrine cells with lipopolyamine-coated DNA. Proc Natl Acad Sci U S A. Sep. 1989;86(18):6982-6.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Chen et al., Tumor-targeted delivery of siRNA by non-viral vector: safe and effective cancer therapy. Expert Opin Drug Deliv. Dec. 2008;5(12):1301-11. doi: 10.1517/17425240802568505.
Felgner et al., Lipofection: a highly efficient, lipid-mediated DNA-transfection procedure. Proc Natl Acad Sci U S A. Nov. 1987;84(21):7413-7.
Fenske et al., Liposomal nanomedicines. Expert Opin Drug Deliv. Jan. 2008;5(1):25-44.
Geng et al., Hydrolytic degradation of poly(ethylene oxide)-block-polycaprolactone worm micelles. J Am Chem Soc. Sep. 21, 2005;127(37):12780-1.
Gunatillake et al., Recent developments in biodegradable synthetic polymers. Biotechnol Annu Rev. 2006;12:301-47.
Gupta et al., A review of in vitro-in vivo investigations on dendrimers: the novel nanoscopic drug carriers. Nanomedicine. Jun. 2006;2(2):66-73.
Heyes et al., Cationic lipid saturation influences intracellular delivery of encapsulated nucleic acids. J Control Release. Oct. 3, 2005;107(2):276-87.
Klibanov et al., Amphipathic polyethyleneglycols effectively prolong the circulation time of liposomes. FEBS Lett. Jul. 30, 1990;268(1):235-7.
Semple et al., Rational design of cationic lipids for siRNA delivery. Nat Biotechnol. Feb. 2010;28(2):172-6. doi:10.1038/nbt.1602. Epub Jan. 17, 2010.
Staubli et al., Hydrolytically degradable amino acid containing polymers. J Am Chem Soc. 1990;45:4419-24.
Tan et al., Engineering Nanocarriers for siRNA Delivery. Small. Apr. 4, 2011;7(7):841-56. doi: 10.1002/sml1.201001389. Epub Feb. 25, 2011.
Van Dijkhuizen-Radersma et al., Biocompatibility and degradation of poly(ether-ester) microspheres: in vitro and in vivo evaluation. Biomaterials. Dec. 2002;23(24):4719-29.
Whitehead et al., In vitro-in vivo translation of lipid nanoparticles for hepatocellular siRNA delivery. ACS Nano. Aug. 28, 2012;6(8):6922-9. doi: 10.1021/nn301922x. Epub Jul. 6, 2012.
Zhang et al., Ionization behavior of amino lipids for siRNA delivery: determination of ionization constants, SAR, and the impact of lipid pKa on cationic lipid-biomembrane interactions. Langmuir. Mar. 1, 2011;27(5):1907-14. doi: 10.1021/la104590k. Epub Jan. 20, 2011.

\* cited by examiner

POLY(BETA-AMINO ALCOHOLS), THEIR PREPARATION, AND USES THEREOF

RELATED APPLICATIONS

The present application is a national stage filing under 35 U.S.C. §371 of international PCT application, PCT/US2011/049360, filed Aug. 26, 2011, which claims priority under 35 U.S.C. §119(e) to U.S. provisional application, U.S. Ser. No. 61/377,348, filed Aug. 26, 2010, each of which is incorporated herein by reference.

BACKGROUND OF THE INVENTION

In many biomedical applications such as cell encapsulation and implantations (R. Langer, *Adv. Mater.* 2009, 21, 3235,) the biological response of the body to the implanted medical device and biomaterial play a critical role in determining the long term success of the implant (J. M. Anderson, *Annu. Rev. Mater. Res.* 2001, 31, 81; M. T. Novak, J. D. Bryers, W. M. Reichert, *Biomaterials* 2009, 30, 1989; D. F. Williams, *Biomaterials* 2008, 29, 2941.) Often, the acute and chronic inflammatory response caused by foreign material and the formation of fibrotic tissue around the device lead to compromised function, device failure, or medical complications. The so-called foreign body response consists of a series of complex reactions involving various types of cells, chemokines, and cytokines. In the simplest view, the recruitment of inflammatory cells such as neutrophils and macrophages to the implantation site is characteristic of the early response, i.e., acute inflammation, while fibrosis is typically considered the end result of chronic inflammation. Both the physical and chemical properties of the biomaterial influence the intensity and/or duration of the foreign body response. Significant research efforts have thus been devoted to controlling the foreign body response by tuning material properties and surface chemistries (B. D. Ratner, S. J. Bryant, *Annu. Rev. Biomed. Eng.* 2004, 6, 41; W. K. Ward, *J. Diabetes Sci. Technol.* 2008, 2, 768; Y. Onuki, U. Bhardwaj, F. Papadimitrakopoulos, D. J. Burgess, *J. Diabetes Sci. Technol.* 2008, 2, 1003.)

Cationic polymers are an important class of polymers that have been used extensively in biomedical applications. For example, in cell encapsulation applications, a polycation is often used as a component to form a semi-permeable polyelectrolyte complex capsule, which protects the encapsulated cells from the attack of host immune systems but allows the facile diffusion of nutrients (T. M. S. Chang, *Nature Reviews Drug Discovery* 2005, 4, 221.) Poly(L-lysine) (PLL) was the first polycation used in alginate-based islet encapsulation system. It has since been widely used, but recently it was shown to have biocompatibility issues (G. Orive et al., *Nature Medicine* 2003, 9, 104.) Discovery of alternative, more biocompatible polycations therefore represents a critical step towards the final clinical success for cell encapsulation. Another example where polycations are used is in layer-by-layer (LBL) coatings, which has become one of the most versatile and robust surface modification approaches for various biomedical applications (T. Boudou, T. Crouzier, K. Ren, G. Blin, C. Picart, *Adv. Mater.* 2010, 22, 441.) The LBL coating involves alternating adsorption of complementary materials from solution, for example, positively and negatively charged species or polymers with hydrogen bond donor and acceptor groups (G. Decher, *Science* 1997, 277, 1232.) The diversity of cationic polymers used in LBL coatings have been relatively limited, with poly(allylamine hydrochloride) (PAH) being commonly used. Thus, development of new polycations, in particular, those with improved immuno-compatibility, will have a tremendous impact in biomedical applications.

SUMMARY OF THE INVENTION

The present invention originates from the discovery that poly(beta-amino alcohols) (PBAAs) for biomedical applications may be prepared by reacting an amine with a diepoxide as shown in the schemes below.

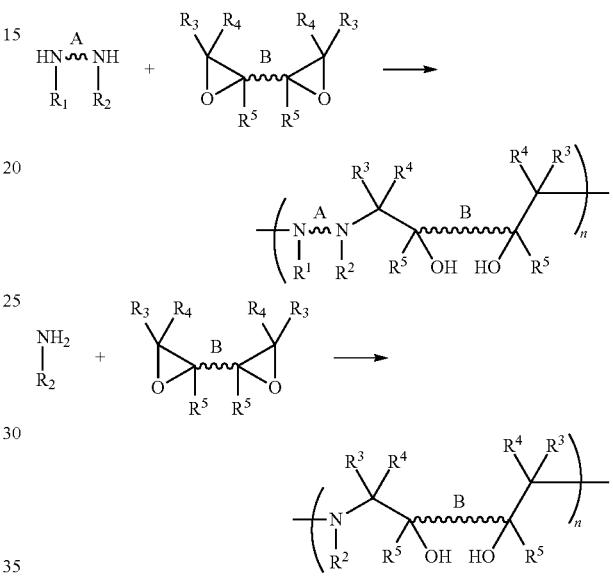

The present invention provides such novel poly(beta-amino alcohols). The inventive poly(beta-amino alcohols) may be used in biotechnology and biomedical applications as coatings (such as coatings of films or multilayer films for medical devices or implants), additives, materials, excipients, non-biofouling agents, micropatterning agents, and cellular encapsulation agents. The inventive polymers may be used for other purposes as well such as, for example, the administration and/or delivery of therapeutic agents (e.g., polynucleotide, small molecule, antigen, drug, protein, peptide, etc.) to a subject, patient, tissue, organ, or cell. Poly(beta-amino alcohols) of the present invention are amenable to combinatorial synthesis to generate libraries of polymers and high-throughput screening to identify polymers with a desired property.

In one aspect, the present invention provides novel poly (beta-amino alcohols) of the formula:

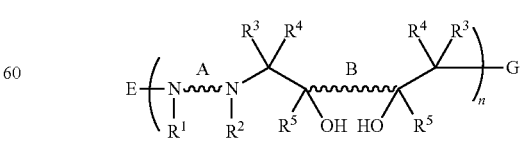

wherein $R^1$, $R^2$, $R^3$, $R^4$, $R^5$, A, B, n, E, and G are as defined herein. In another aspect, the present invention provides novel poly(beta-amino alcohols) of the formula:

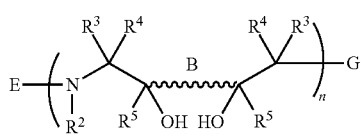

wherein $R^1$, $R^2$, $R^3$, $R^4$, $R^5$, A, B, n, E, and G are as defined herein. These poly(beta-amino alcohols) may be prepared by reacting an amine with a diepoxide. In certain embodiments, the diepoxide is stereochemically pure (e.g., enantiomerically pure). In certain embodiments, the amine is stereochemically pure (e.g., enantiomerically pure).

In another aspect, the present invention provides pharmaceutical compositions comprising a poly(beta-amino alcohol) of the invention; a pharmaceutical agent; and optionally, a pharmaceutically acceptable excipient. The pharmaceutical agent of the composition may be, for example, a polynucleotide, protein, peptide, or small molecule.

The invention also provides methods of preparing the inventive poly(beta-amino alcohols). One or more equivalents of an amine are allowed to react with one or more equivalents of a diepoxide under suitable conditions to form a poly(beta-amino alcohol). Typically, the amines chosen contain between two and five amine moieties and the diepoxides may include one or more tails of varying chain lengths and optionally feature various functional groups and varying degrees of saturation. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the poly(beta-amino alcohol). These primary or secondary amines are left as is or may be reacted with another electrophile. As will be appreciated by one skilled in the art, reacting an amine with less than an excess of epoxide-terminated compound will result in a plurality of different poly(beta-amino alcohols). In certain embodiments, all the amino groups are not fully functionalized. In certain embodiments, a single amine and/or a single diepoxide are used. In other embodiments, two or more different amines and/or two or more different diepoxides are used. The synthesis of the poly(beta-amino alcohol) is performed with or without solvent, and the synthesis may be performed at higher temperatures ranging from 30° C.-100° C., preferably at approximately 50° C.-90° C. The prepared poly(beta-amino alcohols) may be optionally purified. For example, the mixture of poly(beta-amino alcohols) may be purified to yield a particular stereo- or regioisomer. The poly(beta-amino alcohols) may also be alkylated using an alkyl halide (e.g., methyl iodide) or other alkylating agent, and/or they may be acylated, or reacted with other electrophiles.

Poly(beta-amino alcohols) are also amenable to combinatorial synthesis to generate libraries of polymers.

In certain embodiments, the present invention provides methods of preparing a poly(beta-amino alcohol) of the invention comprising the step of reacting an amine of the formula:

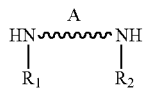

with a diepoxide of the formula:

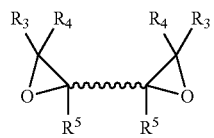

to form a polymer of the formula:

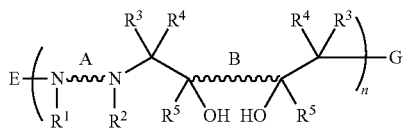

wherein $R^1$, $R^2$, $R^3$, $R^4$, $R^5$, A, B, n, E, and G are as defined herein.

In another embodiment, the present invention provides methods of preparing a poly(beta-amino alcohol) of the invention comprising the step of reacting an amine of the formula:

with a diepoxide of the formula:

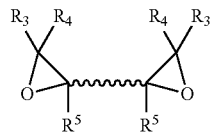

to form a polymer of formula:

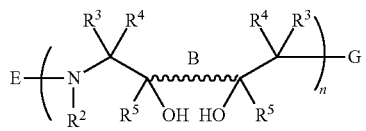

wherein $R^2$, $R^3$, $R^4$, $R^5$, B, n, E, and G are as defined herein.

The inventive poly(beta-amino alcohols) have many different and varied applications. They may be used in biotechnology and biomedical applications as coatings (such as coatings of films or multilayer films for medical devices or implants), additives, materials, excipients, non-biofouling agents, micropatterning agents, and cellular encapsulation agents. The inventive polymers may be used for other purposes as well such as, for example, the administration and/or delivery of therapeutic agents (e.g., polynucleotide, small molecule, antigen, drug, protein, peptide, etc.) to a subject, patient, tissue, organ, or cell. The inventive poly(beta-amino alcohols) are particularly useful in delivering negatively charged agents (e.g., polynucleotides) given the tertiary amines available for protonation thus forming a cationic moiety. For example, the poly(beta-amino alcohol) may be used to delivery DNA, RNA, or other polynucleotides to a subject or to a cell.

In another respect, the invention also provides libraries of poly(beta-amino alcohols) prepared by the inventive methods. These poly(beta-amino alcohols) may be prepared and/or screened using high-throughput techniques involving liquid handlers, robots, microtiter plates, computers, etc. In certain embodiments, the poly(beta-amino alcohols) are screened for their ability to transfect polynucleotides or other agents (e.g., proteins, peptides, small molecules) into a cell. In certain embodiments, the poly(beta-amino alcohols) are screened for their biocompatibility.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" of a substance is a measure of how pure a desired enantiomer is relative to the undesired enantiomer. Enantiomeric excess is defined as the absolute difference between the mole fraction of each enantiomer which is most often expressed as a percent enantiomeric excess. For mixtures of diastereomers, there are analogous definitions and uses for "diastereomeric excess" and percent diastereomeric excess. For example, a sample with 70% of R isomer and 30% of S will have an enantiomeric excess of 40%. This can also be thought of as a mixture of 40% pure R with 60% of a racemic mixture (which contributes 30% R and 30% S to the overall composition).

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methane sulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of diseases or disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" as used herein refers to saturated, straight- or branched-chain hydrocarbon radicals derived from a hydrocarbon moiety containing between one and twenty carbon atoms by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkenyl" denotes a monovalent group derived from a hydrocarbon moiety having at least one carbon-carbon double bond by the removal of a single hydrogen atom. Alkenyl groups include, for example, ethenyl, propenyl, butenyl, 1-methyl-2-buten-1-yl, and the like.

The term "alkynyl" as used herein refers to a monovalent group derived form a hydrocarbon having at least one carbon-carbon triple bond by the removal of a single hydrogen atom. Representative alkynyl groups include ethynyl, 2-propynyl (propargyl), 1-propynyl, and the like.

The term "alkoxy" or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 aliphatic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "carboxylic acid" as used herein refers to a group of formula —$CO_2H$.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl," as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl," as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2 R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle," as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The term "carbocycle," as used herein, refers to an aromatic or non-aromatic ring in which each atom of the ring is a carbon atom.

The term "independently selected" is used herein to indicate that the R groups can be identical or different.

As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

The terms "halo" and "halogen" as used herein refer to an atom selected from fluorine, chlorine, bromine, and iodine.

The term "heterocyclic," as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term "heteroaryl," as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "substituted," whether preceded by the term "optionally" or not, and "substituent," as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The following are more general terms used throughout the present application:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc. In certain embodiments, an poly(beta-amino alcohols) is associated with a polynucleotide through electrostatic interactions.

"Biocompatible": The term "biocompatible," as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain embodiments, the chemical reactions relied upon to break down the biodegradable compounds are uncatalyzed.

"Effective amount": In general, the "effective amount" of an active agent or composition refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

"Medical device" and "implant": As used herein, the terms "medical device" and "implant" refer to any object that is designed to be placed partially or wholly within a patient's body for one or more therapeutic or prophylactic purposes such as for restoring physiological function, alleviating symptoms associated with a disease, delivering therapeutic agents, and/or repairing, replacing, or augmenting damaged or diseased organs and tissues. While normally composed of biologically compatible synthetic materials (e.g., medical-grade stainless steel, titanium, and other metals; polymers such as polyurethane, silicon, PLA, PLGA, and other materials) that are exogenous, some medical devices and implants include materials derived from animals (e.g., "xenografts" such as whole animal organs; animal tissues such as heart valves; naturally occurring or chemically-modified molecules such as collagen; hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices of particular utility in the present invention include, but are not restricted to, vascular stents, gastrointestinal stents, tracheal/bronchial stents, genital-urinary stents, ENT stents, intraocular lenses, implants for hypertrophic scars and keloids, vascular grafts, anastomotic connector devices, surgical adhesion barriers, glaucoma drainage devices, film or mesh, prosthetic heart valves, tympanostomy tubes, penile implants, endotracheal and tracheostomy tubes, peritoneal dialysis catheters, intracranial pressure monitors, vena cava filters, CVCs, ventricular assist device (e.g., LVAD), spinal prostheses, and gastrointestinal drainage tubes.

A wide variety of implants and devices can be coated with or otherwise constructed to contain and/or release the poly (beta-amino alcohols) provided herein. Representative examples include cardiovascular devices (e.g., implantable venous catheters, venous ports, tunneled venous catheters, chronic infusion lines or ports, including hepatic artery infusion catheters, pacemakers and pacemaker leads (see, e.g., U.S. Pat. Nos. 4,662,382, 4,782,836, 4,856,521, 4,860,751, 5,101,824, 5,261,419, 5,284,491, 6,055,454, 6,370,434, and 6,370,434, the entire contents of which are hereby incorporated by reference), implantable defibrillators (see, e.g., U.S. Pat. Nos. 3,614,954, 3,614,955, 4,375,817, 5,314,430, 5,405,363, 5,607,385, 5,697,953, 5,776,165, 6,067,471, 6,169,923, and 6,152,955, the entire contents of which are hereby incorporated by reference)); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, and suspensions or solid implants to prevent surgical adhesions); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy, central venous catheters (see, e.g., U.S. Pat. Nos. 3,995,623, 4,072,146 4,096,860, 4,099,528, 4,134,402, 4,180,068, 4,385,631, 4,406,656, 4,568,329, 4,960,409, 5,176,661, 5,916,208, the entire contents of which are hereby incorporated by reference), urinary catheters (see, e.g. U.S. Pat. Nos. 2,819,718, 4,227,533, 4,284,459, 4,335,723, 4,701,162, 4,571,241, 4,710,169, and 5,300,022, the entire contents of which are hereby incorporated by reference.)); prosthetic heart valves (see, e.g., U.S. Pat. Nos. 3,656,185, 4,106,129, 4,892,540, 5,528,023, 5,772,694, 6,096,075, 6,176,877, 6,358,278, and 6,371,983, the entire contents of which are hereby incorporated by reference), vascular grafts (see, e.g., U.S. Pat. Nos. 3,096,560, 3,805,301, 3,945,052, 4,140,126, 4,323,525, 4,355,426, 4,475,972, 4,530,113, 4,550,447, 4,562,596, 4,601,718, 4,647,416, 4,878,908, 5,024,671, 5,104,399, 5,116,360, 5,151,105, 5,197,977, 5,282,824, 5,405,379, 5,609,624, 5,693,088, and 5,910,168, the entire contents of which are hereby incorporated by reference), ophthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., breast implants or chin implants), catheter cuffs and orthopedic implants (e.g., cemented orthopedic prostheses).

Further examples of such implants or devices which can be coated with or otherwise constructed to contain and/or release the inventive poly(beta-amino alcohols) include vascular stents, gastrointestinal stents, tracheal/bronchial stents, genital-urinary stents, ENT stents, intraocular lenses, implants for hypertrophic scars and keloids, vascular grafts, anastomotic connector devices, surgical adhesion barriers, glaucoma drainage devices, prosthetic heart valves, tympanostomy tubes, penile implants, CVCs, ventricular assist devices (e.g., LVAD's), spinal prostheses, endotracheal and tracheostomy tubes, peritoneal dialysis catheters, intracranial pressure monitors, vena cava filters, and gastrointestinal drainage tubes.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. In certain embodiments, the small molecule is uncharged. In certain embodiments, the small molecule is negatively charged. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

"Step-growth polymerization": As used herein, the term "step-growth polymerization" refers to a type of polymerization mechanism in which bi-functional or multifunctional monomers react to form first dimers, then trimers, longer oligomers and eventually long chain polymers. Many naturally occurring and some synthetic polymers are produced by step-growth polymerization (e.g. polyesters, polyamides, polyurethanes, etc.) Due to the nature of the polymerization mechanism, a high extent of reaction is required to achieve high molecular weight. The easiest way to visualize the mechanism of a step-growth polymerization is a group of people reaching out to hold their hands to form a human chain—each person has two hands (i.e., reactive sites). There also is the possibility of having more than two reactive sites on a monomer. In such a case branched polymers are produced.

DETAILED DESCRIPTION OF CERTAIN EMBODIMENTS OF THE INVENTION

Figure 1A:
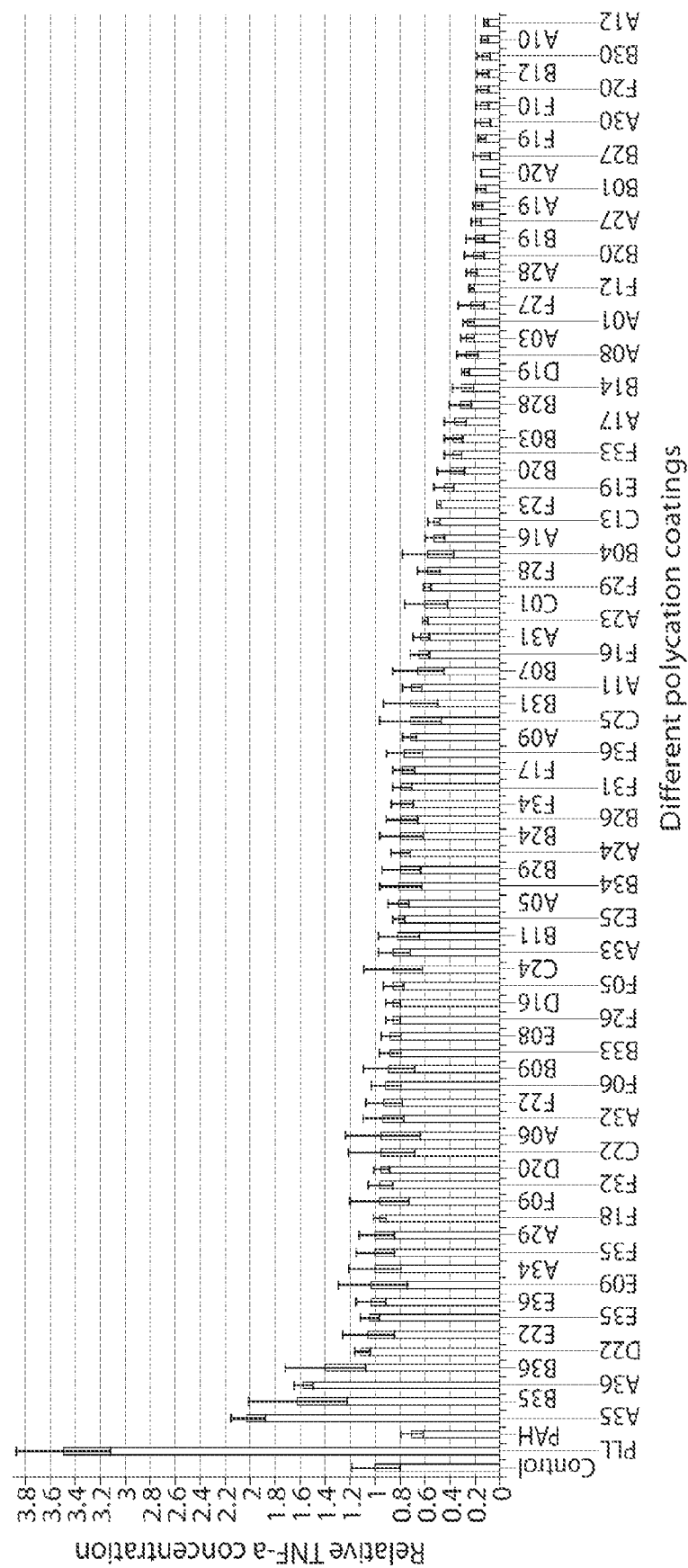
FIG. 1 depicts the in vitro screening of PBAAs for biocompatible coatings using monocyte/macrophage cells. (a) The dependence of TNF-α concentration on surface chemistry. The control is the uncoated glass surface. SEM images show the morphological differences of the cells between uncoated surface (b) and B20-coated surface (c). Insets show the morphologies of single cells.
Figure 1B:
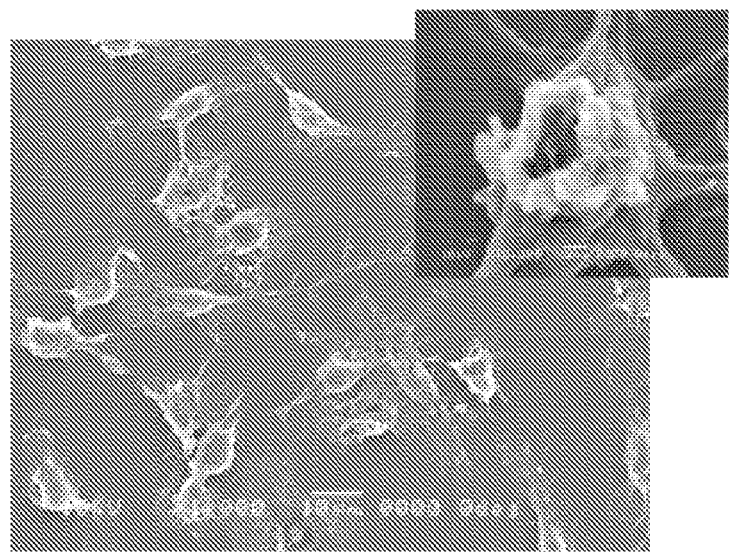
Figure 1C:
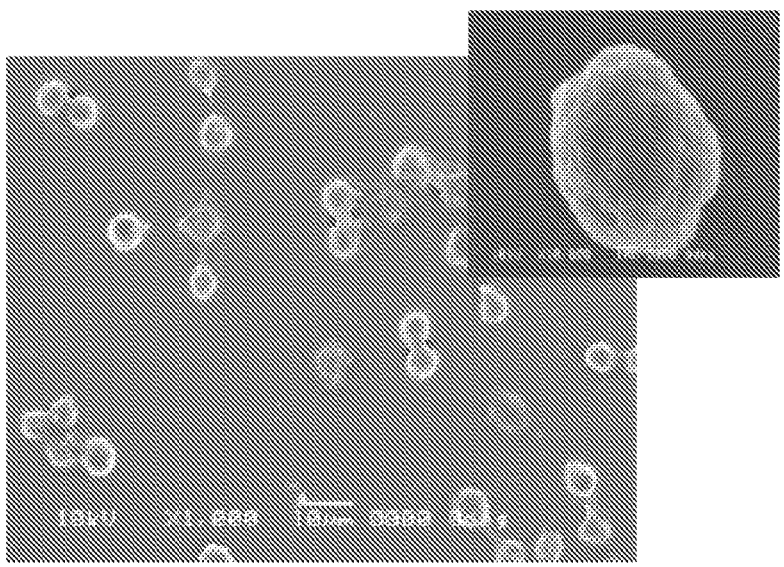
Figure 2A:
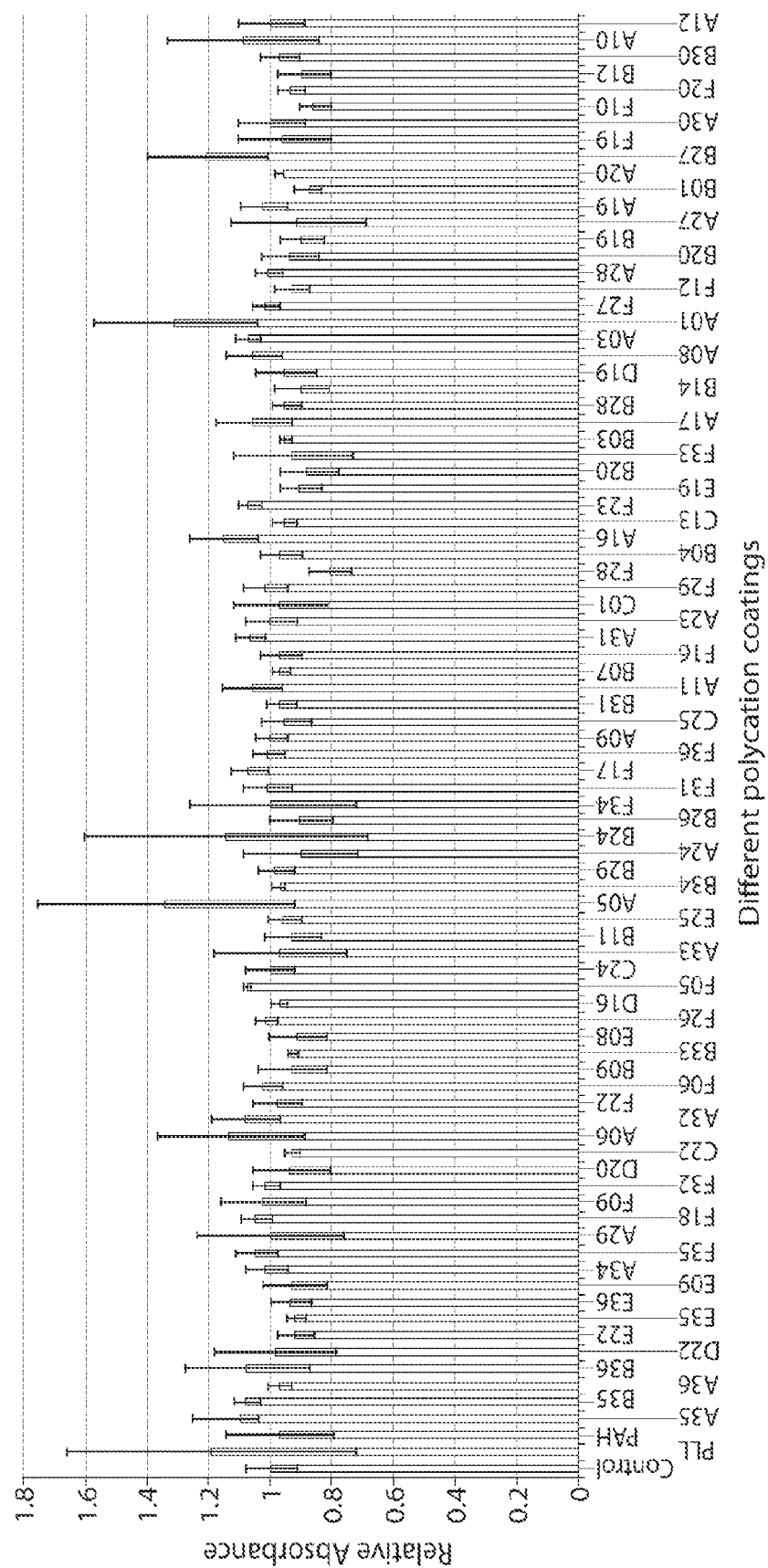
FIG. 2 depicts the cell viability and characterization of the PBAA coatings. (a) The dependence of relative absorbance on different PBAA coatings. Optical images show live staining of the cells on uncoated (b) and B20-coated surfaces (c). (d) The concentrations of TNF-α secreted by cells on normal coatings, presoaked surfaces and uncoated surfaces with preconditioned media. (e) XPS of uncoated surface (bottom), B20 coated surface (top) and B20 coated surface soaked in PBS for 24 hours (middle).
Figure 2B:
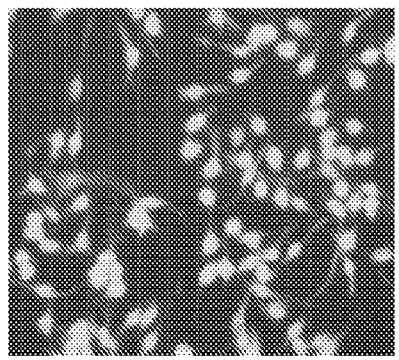
Figure 2C:
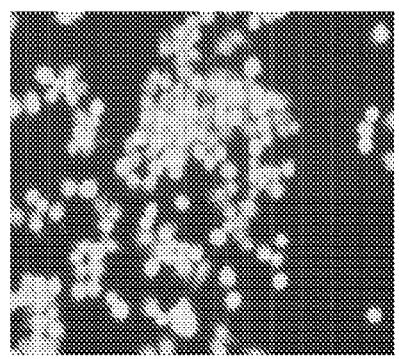
Figure 2D:
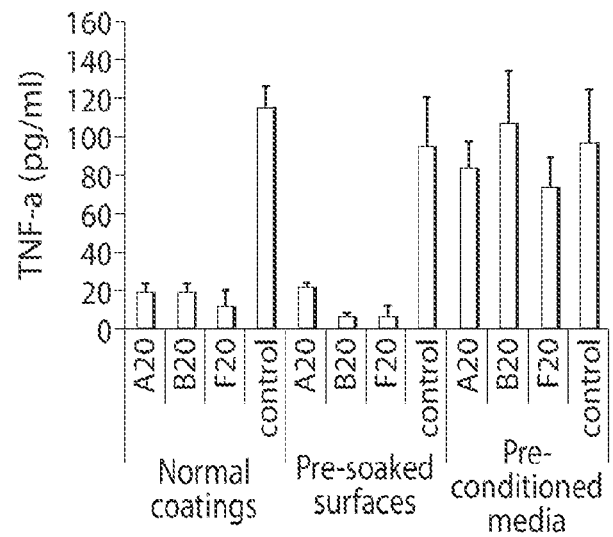
Figure 2E:
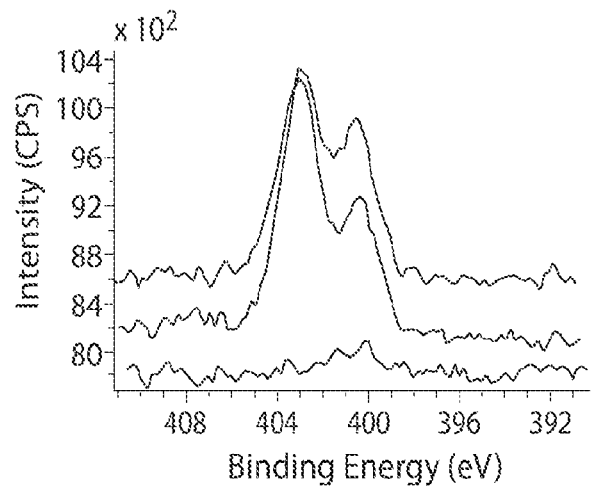
Figure 3A:
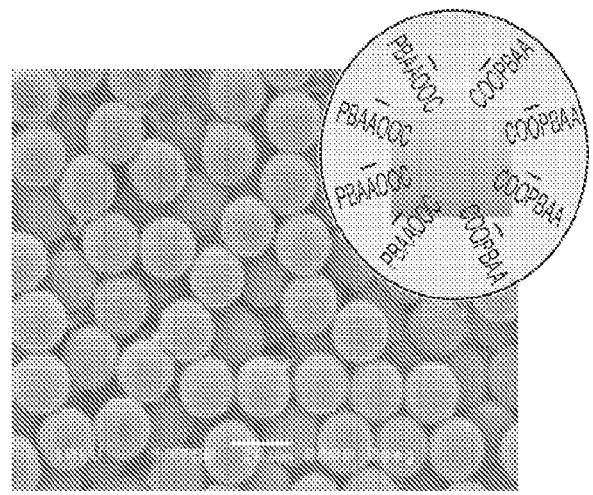
FIG. 3 depicts the imaging of live animals with subcutaneously-injected PBAA-coated microparticles. (a) SEM image of carboxylated polystyrene beads used as the substrate for PBAA coatings. The inset is the schematic of the PBAA coating on the particles (not to scale). (b) Chemical structures of A12 and B35, which promote or inhibit the activation of monocyte/macrophage cells in vitro, respectively. (c) The configuration of six injections on the back of a mouse. (d) Fluorescent images of mice (five replicates) 24 hours after injections using Prosense 750 as the probe and quantitative results from the image analysis. (e) Luminescent image of the same five mice using Luminol as the probe and quantitative results.
Figure 3B:
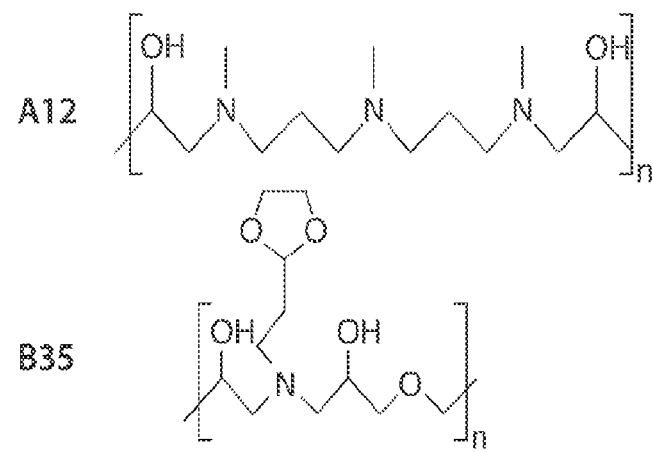
Figure 3C:
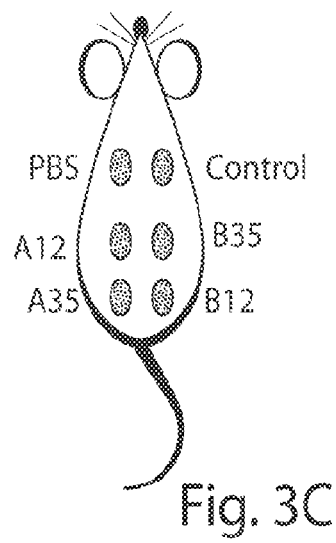
Figure 3D:
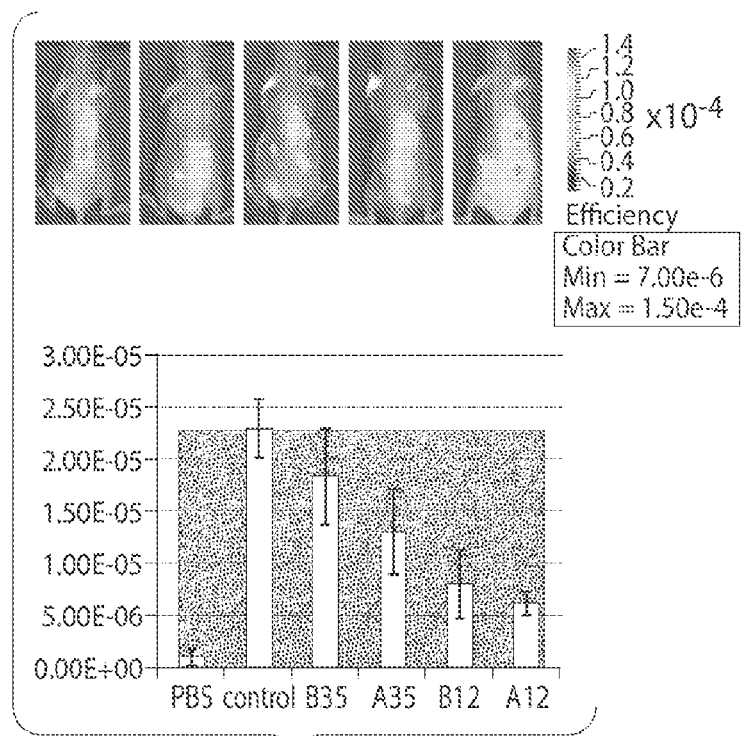
Figure 3E:
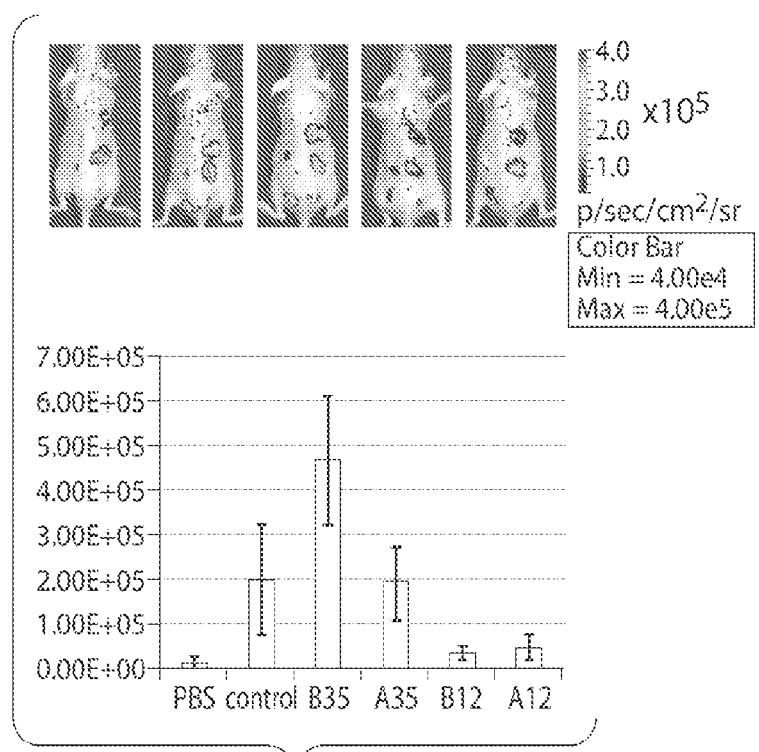

Combinatorial polymerization was used to synthesize a new class of novel cationic polymers, poly(beta-amino alcohols) (PBAAs). The synthesized polymers covered a wide range of chemical functionality and can be easily applied as a coating for the study of surface chemistry effects on the foreign body response. An initial in vitro screening was used to identify the polymer coatings that promoted or inhibited the activation of mouse monocyte/macrophage cells by measuring the secretion of a pro-inflammatory cytokine, tumor necrosis factor-α (TNF-α). The polymer coatings that induced the highest and lowest levels of TNF-α secretion were used to coat carboxylated polystyrene microparticles which were subsequently injected into mice subcutaneously. Twenty-four hours after the injections significantly different levels of inflammatory cell recruitment into the implantation sites were observed using live animal imaging. Histological analysis of the fibrosis around the particles 30 days after injections showed correlation with both the in vitro and live imaging results.

Poly(Beta-amino Alcohols) (PBAA)

The poly(beta-amino alcohols) of the present invention are poly(beta-amino alcohols) containing primary, secondary, tertiary, and/or quaternary amines, and salts thereof. In certain embodiments, the inventive poly(beta-amino alcohols) are relatively non-cytotoxic. In another embodiment, the inventive poly(beta-amino alcohols) are biocompatible and biodegradable. In certain embodiments, the poly(beta-amino alcohols) of the present invention have $pK_a$s in the range of approximately 5.5 to approximately 7.5, more preferably between approximately 6.0 and approximately 7.0. In another embodiment, the poly(beta-amino alcohols) may be designed to have a desired $pK_a$ between approximately 3.0 and approximately 9.0, or between approximately 5.0 and approximately 8.0.

The inventive poly(beta-amino alcohols) may be used in biotechnology and biomedical applications as coatings (such as coatings of films or multilayer films for medical devices or implants), additives, materials, excipients, non-biofouling agents, micropatterning agents, and cellular encapsulation agents. The inventive polymers may be used for other purposes as well such as, for example, the administration and/or delivery of therapeutic agents (e.g., polynucleotide, small molecule, antigen, drug, protein, peptide, etc.) to a subject, patient, tissue, organ, or cell, etc. The inventive poly(beta-amino alcohols) are particularly attractive for drug delivery for several reasons: 1) they contain amino groups for interacting with DNA, RNA, other polynucleotides, and other negatively charged agents, for buffering the pH, for causing endosomolysis, for protecting the agent to be delivered, etc.; 2) they can be synthesized from commercially available starting materials; and/or 3) they are pH responsive and can be engineered with a desired $pK_a$.

In certain embodiments, the poly(beta-amino alcohols) are prepared by reacting an amine with a diepoxide according to the following schemes:

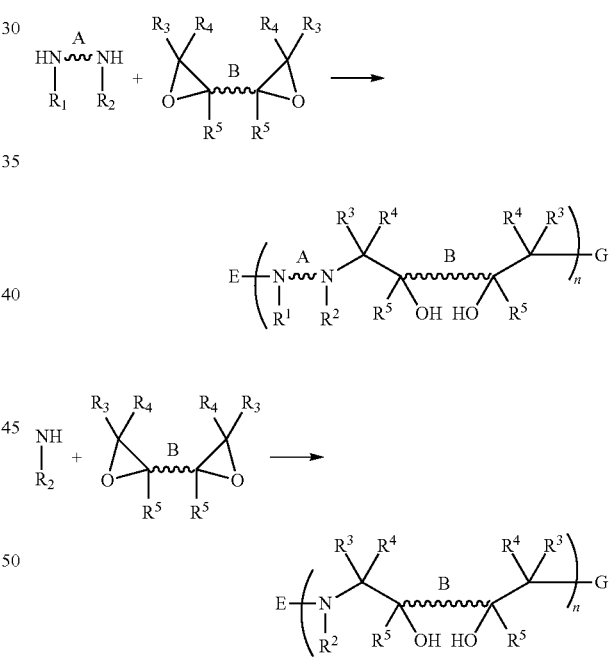

wherein $R^1$, $R^2$, $R^3$, $R^4$, $R^5$, A, B, n, E, and G are as defined herein.

In certain embodiments, the diepoxide is stereochemically pure (e.g., enantiomerically pure). In certain embodiments, the amine is stereochemically pure (e.g., enantiomerically pure). As will be appreciated by one of skill in the art, the amine may be reacted with an excess of diepoxide to form a fully functionalized poly(beta-amino alcohols). Or, the poly(beta-amino alcohols) may be prepared from an excess of amino functional groups relative to epoxide functional groups.

The poly(beta-amino alcohols) of the present invention is of the formula:

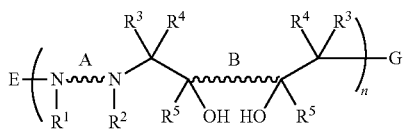

wherein:

each A and B is, independently, a bond; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; substituted or unsubstituted aryl; or a substituted or unsubstituted heteroaryl;

each $R^1$ and $R^2$ is, independently, hydrogen; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; substituted or unsubstituted aryl; or a substituted or unsubstituted heteroaryl;

each

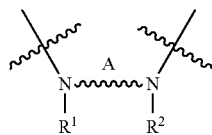

may optionally form a cyclic structure by the joining of $R^1$ and $R^2$;

each $R^3$, $R^4$, and $R^5$ is hydrogen; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; a substituted or unsubstituted aryl; or a substituted or unsubstituted heteroaryl;

each

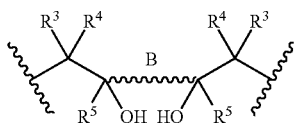

may optionally form a cyclic structure;

each E and G is, independently, hydrogen; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; substituted or unsubstituted aryl; a substituted or unsubstituted heteroaryl;

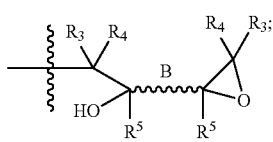

-continued

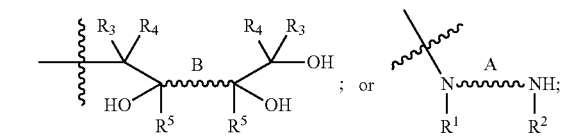

n is an integer from 2 to 10,000, inclusive; or a salt thereof.

In certain embodiments, A is substituted or unsubstituted, branched or unbranched, cyclic or acyclic $C_{1-20}$ aliphatic. In certain embodiments, A is substituted or unsubstituted, branched or unbranched, cyclic or acyclic $C_{1-20}$ heteroaliphatic. In certain embodiments, A is a substituted or unsubstituted aryl. In certain embodiments, A is a substituted or unsubstituted heteroaryl. In certain embodiments, A is substituted or unsubstituted, branched or unbranched, cyclic or acyclic $C_{1-20}$ alkylene. In certain embodiments, A is selected from the group consisting of:

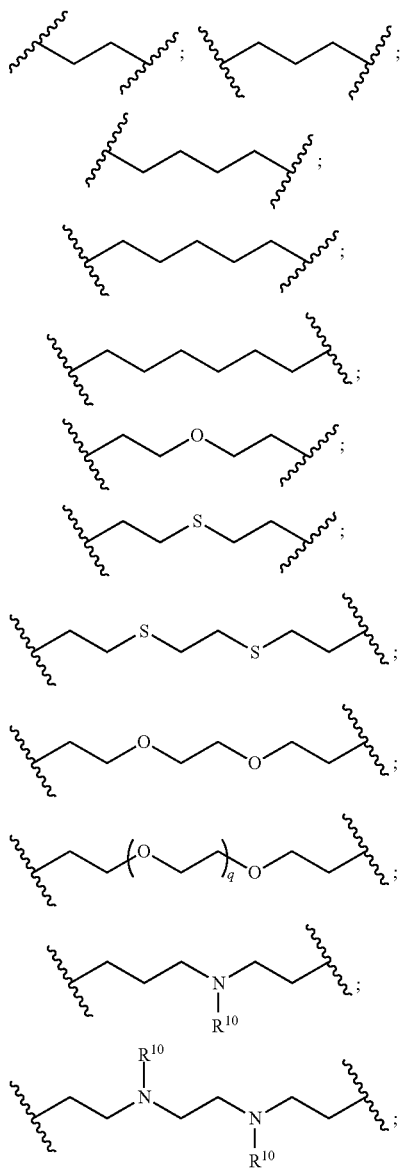

-continued

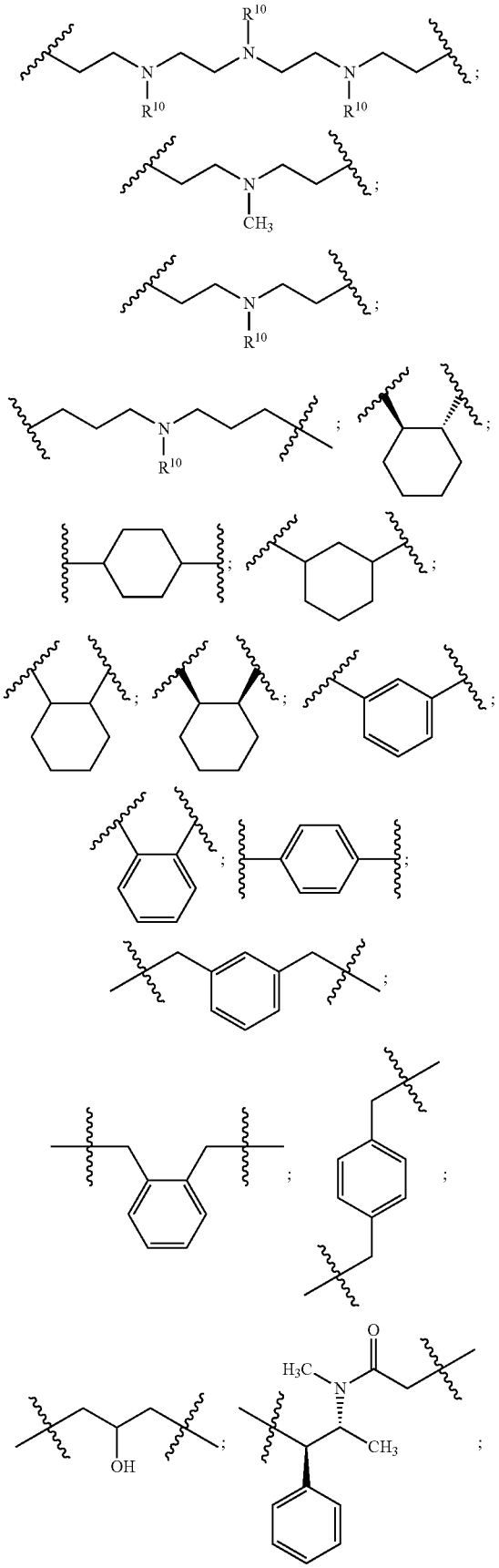

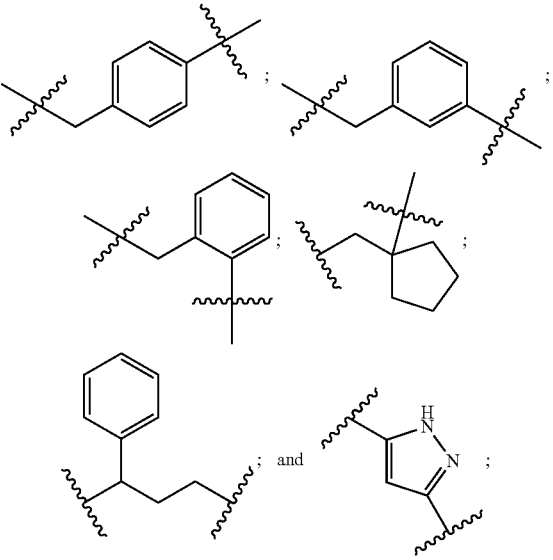

wherein
each $R^{10}$ is, independently, hydrogen; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; substituted or unsubstituted aryl; a substituted or unsubstituted heteroaryl; or an N-protecting group; and
each q is, independently, an integer between 0 and 10, inclusive.

In certain embodiments,

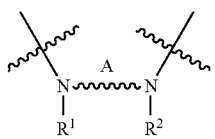

is selected from the group consisting of:

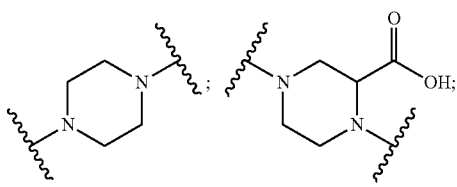

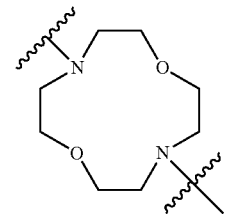

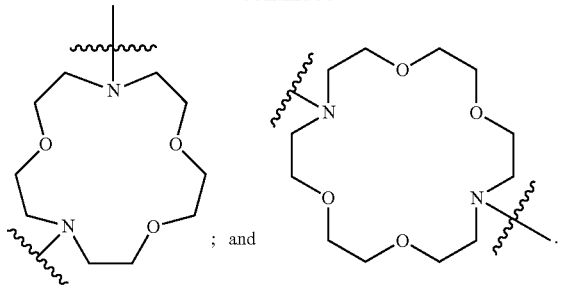

In certain embodiments, B is substituted or unsubstituted, branched or unbranched, cyclic or acyclic $C_{1-20}$ aliphatic. In certain embodiments, B is substituted or unsubstituted, branched or unbranched, cyclic or acyclic $C_{1-20}$ heteroaliphatic. In certain embodiments, B is a substituted or unsubstituted aryl. In certain embodiments, B is a substituted or unsubstituted heteroaryl. In certain embodiments, B is substituted or unsubstituted, branched or unbranched, cyclic or acyclic $C_{1-20}$ alkylene. In certain embodiments, B is selected from the group consisting of:

a bond,

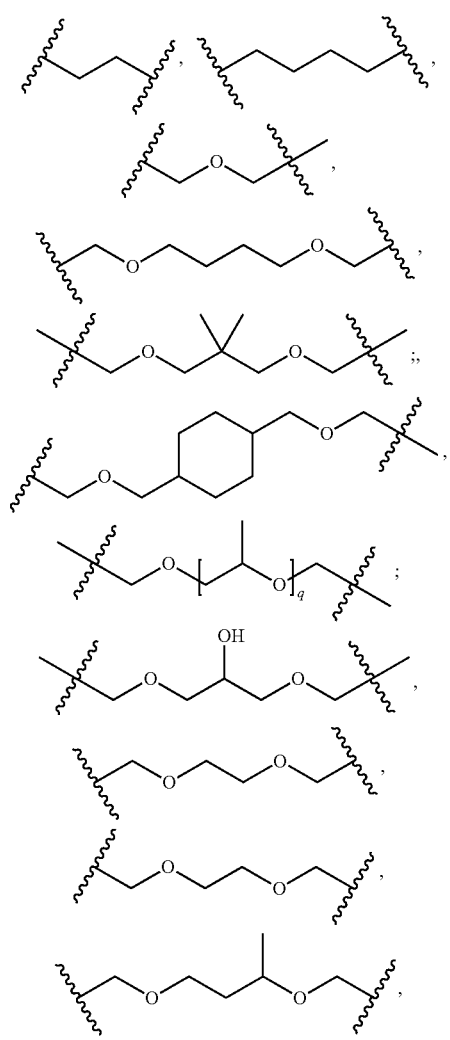

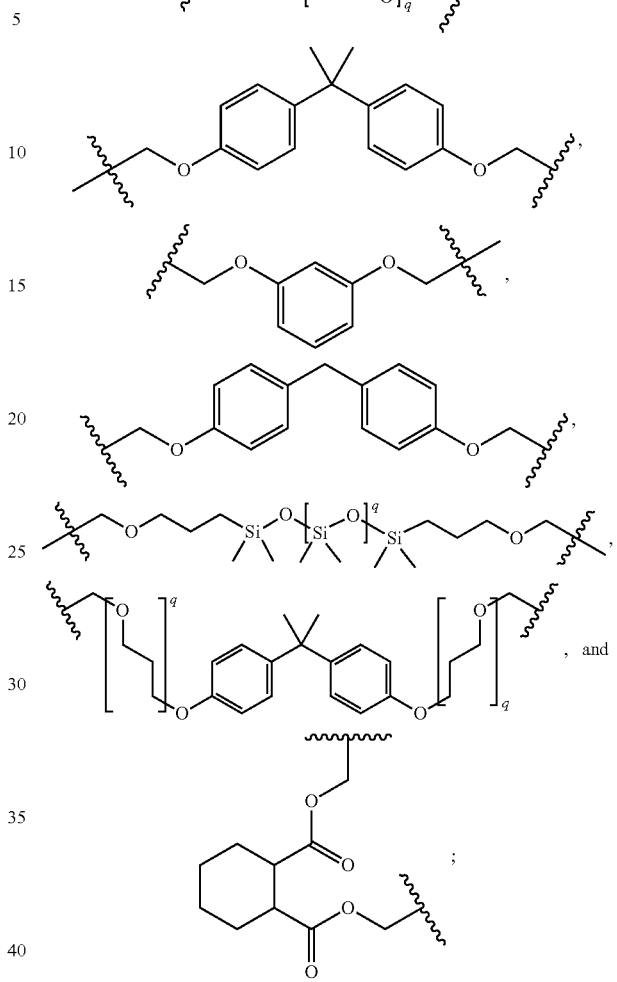

wherein each q is, independently, an integer between 0 and 10, inclusive.

In certain embodiments, each $R^1$ and $R^2$ is independently substituted or unsubstituted, branched or unbranched, cyclic or acyclic $C_{1-20}$ aliphatic. In certain embodiments, each $R^1$ and $R^2$ is independently substituted or unsubstituted, branched or unbranched, cyclic or acyclic $C_{1-20}$ heteroaliphatic. In certain embodiments, each $R^1$ and $R^2$ is independently a substituted or unsubstituted aryl. In certain embodiments, each $R^1$ and $R^2$ is independently a substituted or unsubstituted heteroaryl. In certain embodiments, each $R^1$ and $R^2$ is independently substituted or unsubstituted, branched or unbranched, cyclic or acyclic $C_{1-20}$ alkylene. In certain embodiments, $R^1$ and $R^2$ are the same. In certain embodiments, $R^1$ and $R^2$ are different. In certain embodiments, each $R^1$ and $R^2$ are all hydrogen or all $C_1$-$C_6$ alkyl. In certain embodiments, each $R^1$ and $R^2$ are all hydrogen. In certain embodiments, each $R^1$ and $R^2$ are all $C_1$-$C_6$ alkyl. In certain embodiments, each $R^1$ and $R^2$ are all hydroxyalkyl. In certain embodiments, each $R^1$ and $R^2$ are all aminoalkyl. In certain embodiments, each $R^1$ and $R^2$ are hydrogen or methyl. In certain embodiments, each $R^1$ and $R^2$ is independently selected from the group consisting of:

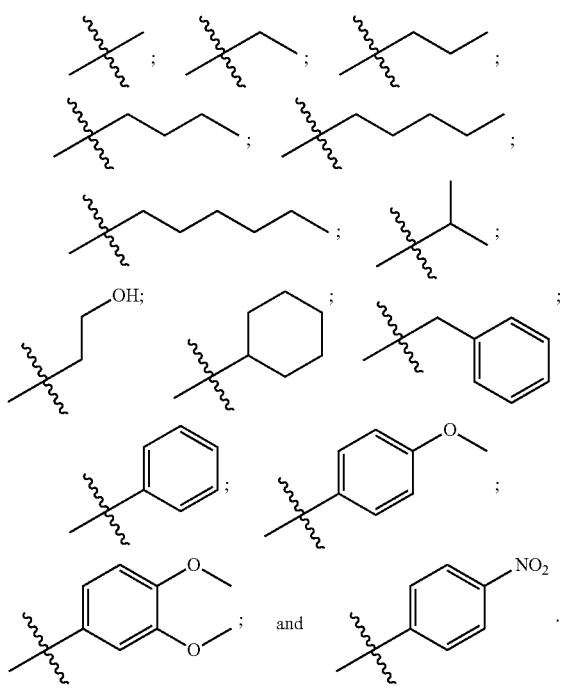

In certain embodiments, each $R^3$, $R^4$, and $R^5$ is hydrogen or an independently substituted or unsubstituted, branched or unbranched, cyclic or acyclic $C_{1-20}$ aliphatic. In certain embodiments, each $R^3$, $R^4$, and $R^5$ is hydrogen or an independently branched $C_1$-$C_{20}$ aliphatic. In certain embodiments, each $R^3$, $R^4$, and $R^5$ is hydrogen or an independently unbranched $C_1$-$C_{20}$ aliphatic. In certain embodiments, each $R^3$, $R^4$, and $R^5$ is hydrogen or an independently fluorinated $C_1$-$C_{20}$ aliphatic. In certain embodiments, each $R^3$, $R^4$, and $R^5$ is hydrogen or an independently substituted or unsubstituted, branched or unbranched, cyclic or acyclic $C_{1-20}$ heteroaliphatic. In certain embodiments, each $R^3$, $R^4$, and $R^5$ is hydrogen or an independently substituted or unsubstituted aryl. In certain embodiments, each $R^3$, $R^4$, and $R^5$ is hydrogen or an independently substituted or unsubstituted heteroaryl. In certain embodiments, each $R^3$, $R^4$, and $R^5$ is hydrogen or an independently substituted or unsubstituted, branched or unbranched, cyclic or acyclic $C_{1-20}$ alkyl. In certain embodiments, each $R^3$, $R^4$, and $R^5$ is hydrogen or an independently substituted or unsubstituted, cyclic or acyclic, branched or unbranched $C_1$-$C_{15}$ alkyl. In certain embodiments, each $R^3$, $R^4$, and $R^5$ is hydrogen or an independently substituted or unsubstituted, cyclic or acyclic, branched or unbranched $C_1$-$C_{10}$ alkyl. In certain embodiments, each $R^3$, $R^4$, and $R^5$ is hydrogen or an independently substituted or unsubstituted, cyclic or acyclic, branched or unbranched $C_1$-$C_5$ alkyl.

In certain embodiments, all $R^3$ and $R^4$ are not hydrogen. In certain embodiments, all $R^3$ and $R^4$ are hydrogen. In certain embodiments, all $R^3$, $R^4$, and $R^5$ are not hydrogen. In certain embodiments, all $R^3$, $R^4$, and $R^5$ are hydrogen. In certain embodiments, $R^5$ is hydrogen.

In certain embodiments, each $R^3$, $R^4$, and $R^5$ is independently selected from the group consisting of:

-continued

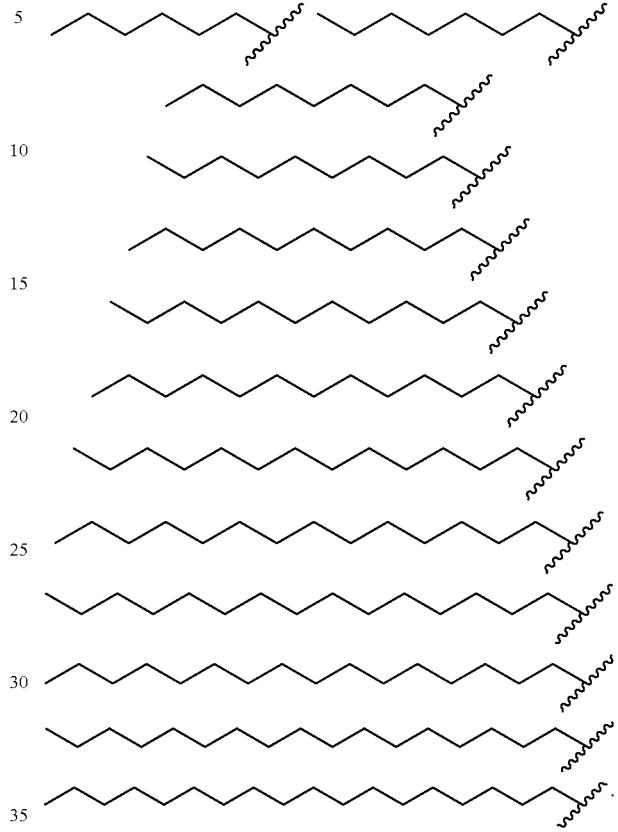

In certain embodiments, each $R^3$, $R^4$, and $R^5$ is independently hydrogen or a substituted or unsubstituted, cyclic or acyclic, branched or unbranched $C_1$-$C_{20}$ alkenyl. In certain embodiments, each $R^3$, $R^4$, and $R^5$ is independently selected from the group consisting of:

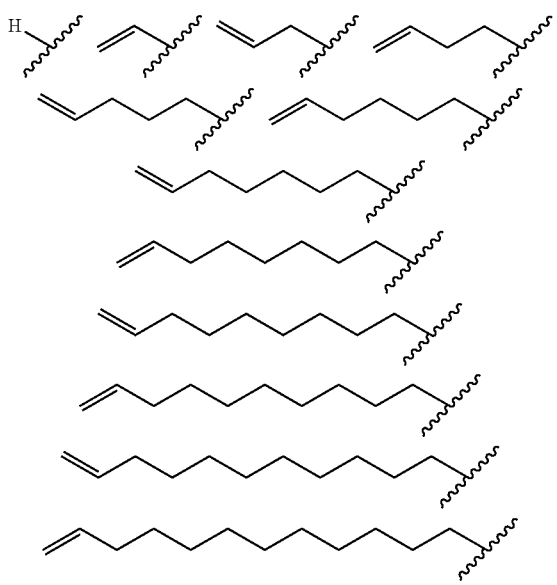

-continued
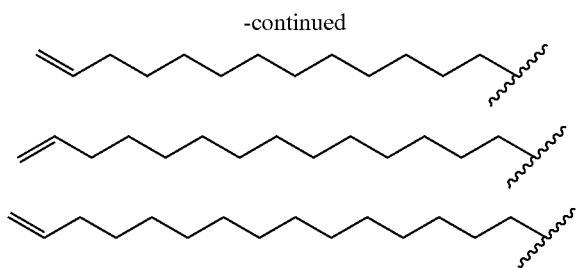
-continued
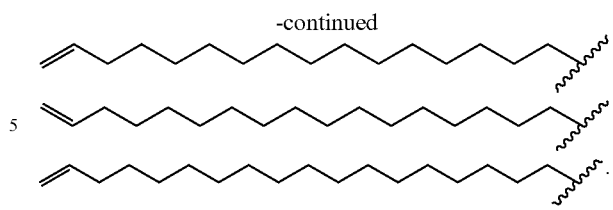
In certain embodiments, each $R^3$, $R^4$, and $R^5$ is independently selected from the group consisting of:
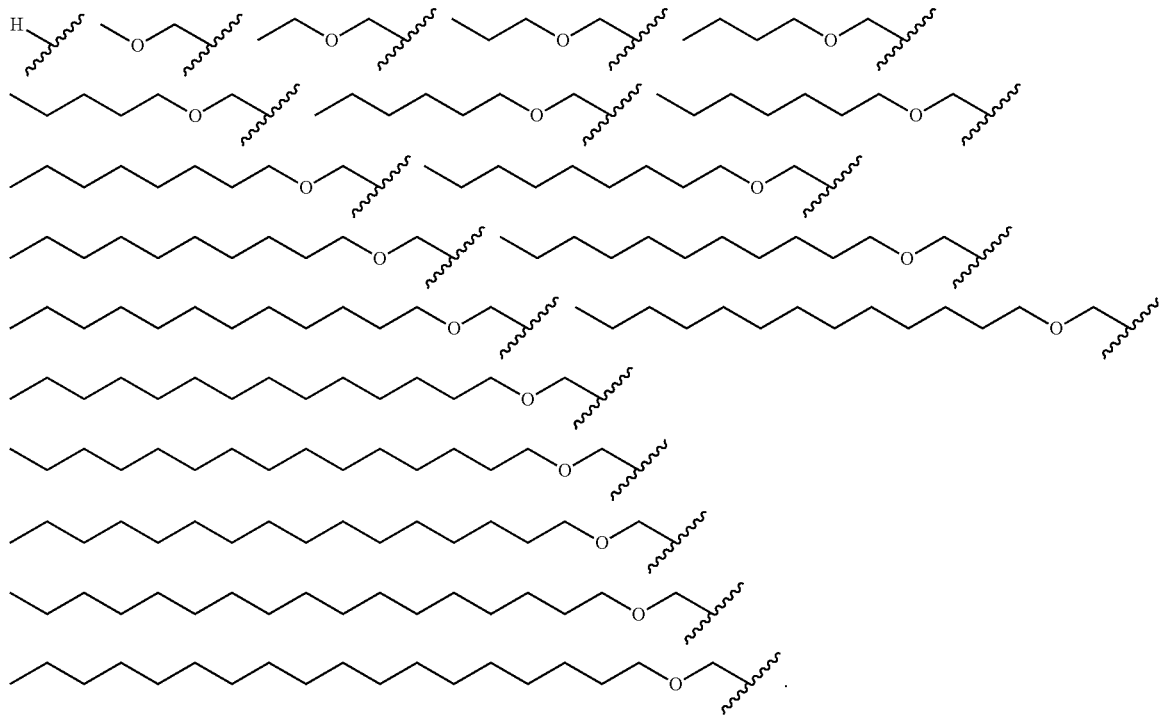
In certain embodiments, each $R^3$, $R^4$, and $R^5$ is independently selected from the group consisting of:
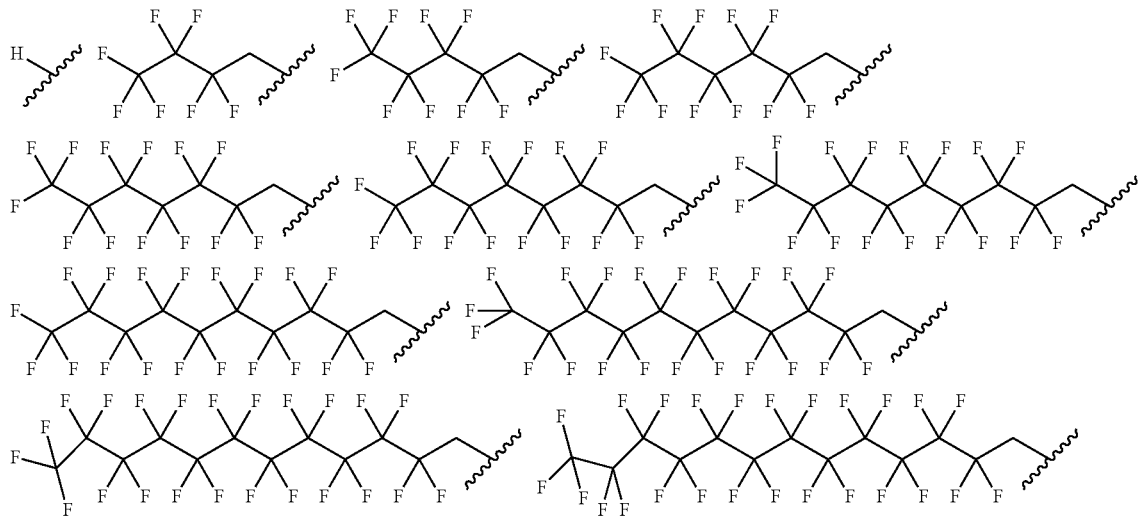

-continued

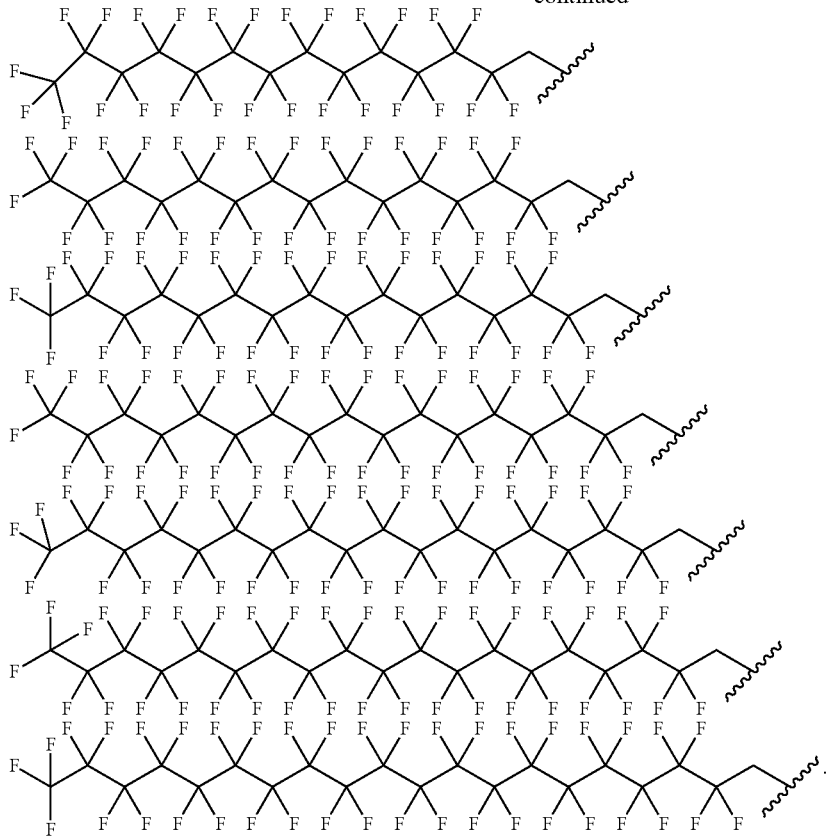

In certain embodiments, each

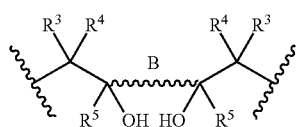

is selected from the group consisting of:

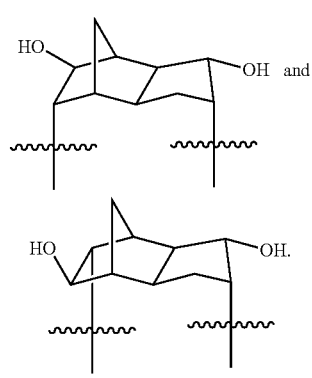

In certain embodiments, the molecular weight ranges between 1,000 and 100,000 Daltons. In certain embodiments, the molecular weight ranges between 3,000 and 70,000 Daltons. In certain embodiments, the molecular weight ranges between 5,000 and 40,000 Daltons. In certain embodiments, the molecular weight ranges between 5,000 and 30,000 Daltons. In certain embodiments, the molecular weight ranges between 5,000 and 20,000 Daltons. In certain embodiments, the molecular weight ranges between 10,000 and 20,000 Daltons.

In certain embodiments, the polymer has at least one secondary amine functional group in every repeating unit. In certain embodiments, the polymer has at least one tertiary amine functional group in every repeating unit. In certain embodiments, the polymer has at least one quaternary amine functional group in every repeating unit.

In certain embodiments, the polymer is linear. In certain embodiments, the polymer is branched. In certain embodiments, the polymer is dendritic. In certain embodiments, the polymer is not water soluble. In certain embodiments, the polymer is biodegradable.

In certain embodiments, the polymer is water-soluble. In certain embodiments, the polymer is hydrolytically stable. In certain embodiments, the polymer is not biodegradable. In certain embodiments, less than 25% of the polymer is degraded after one year in vivo. In certain embodiments, less than 10% of the polymer is degraded after one year in vivo. In certain embodiments, less than 5% of the polymer is degraded after one year in vivo. In certain embodiments, less than 1% of the polymer is degraded after one year in vivo. In certain embodiments, less than 25% of the polymer is degraded after five years in vivo. In certain embodiments, less than 10% of the polymer is degraded after five years in vivo. In certain embodiments, less than 5% of the polymer is degraded after five years in vivo. In certain embodiments, less than 1% of the polymer is degraded after five years in vivo.

In some aspects, the poly(beta-amino alcohols) of the present invention is prepared from a diepoxide selected from the group consisting of:
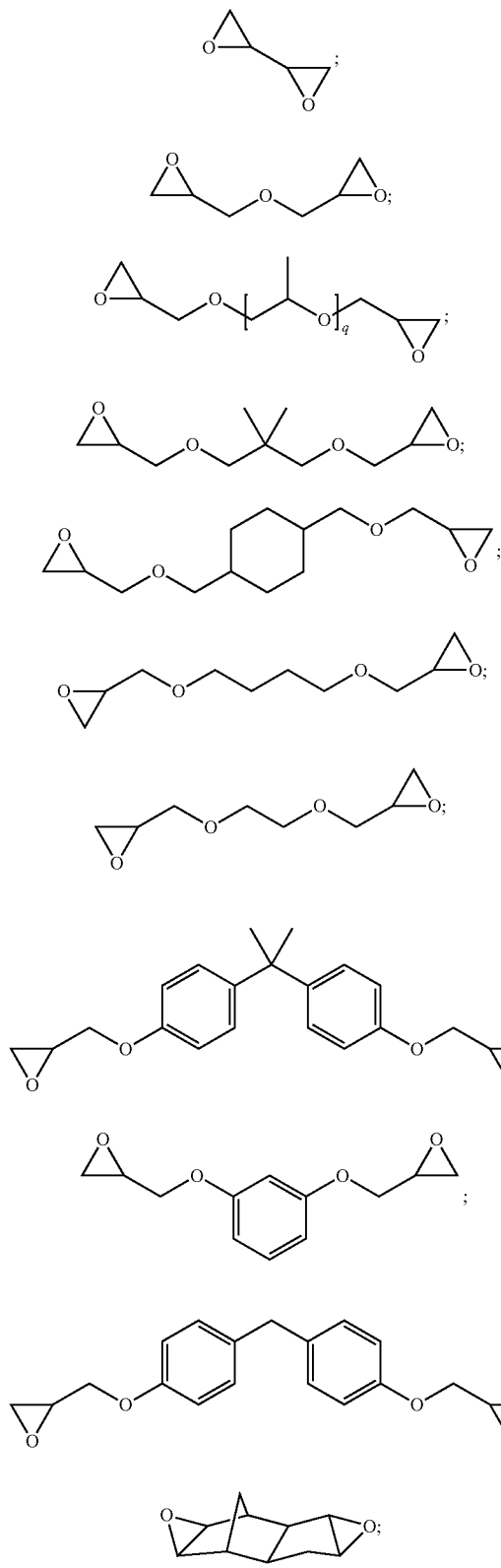
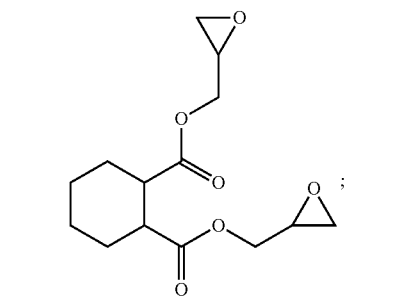
wherein each q is, independently, an integer between 0 and 10, inclusive.
In some aspects, the poly(beta-amino alcohols) of the present invention is prepared from a diepoxide selected from the group consisting of:

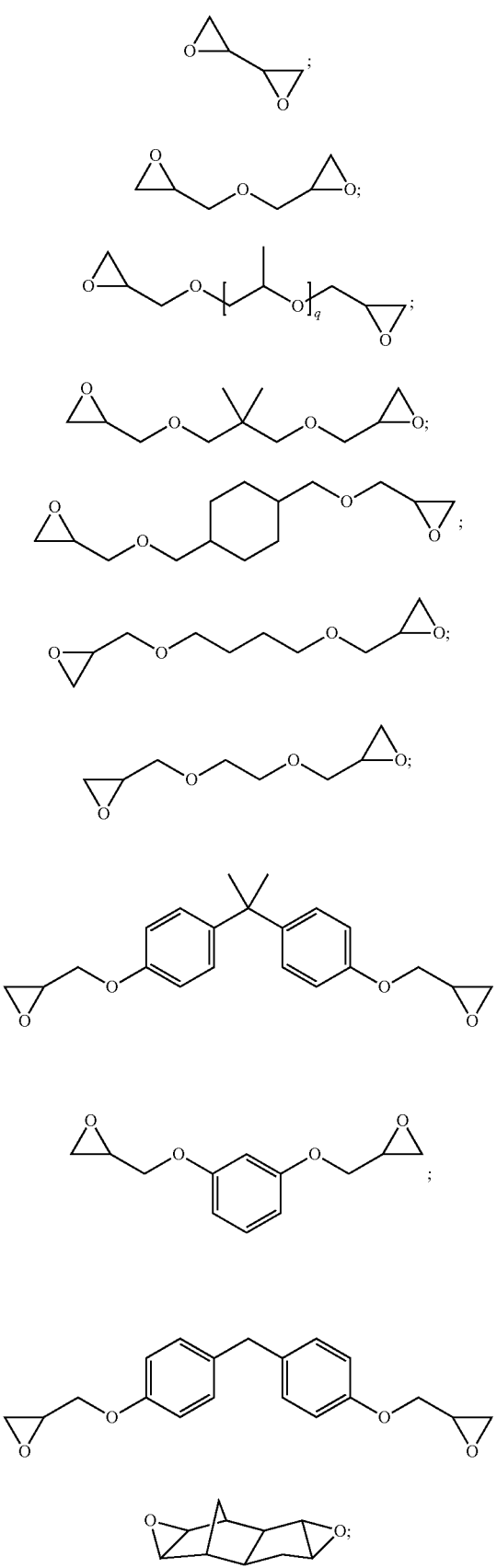
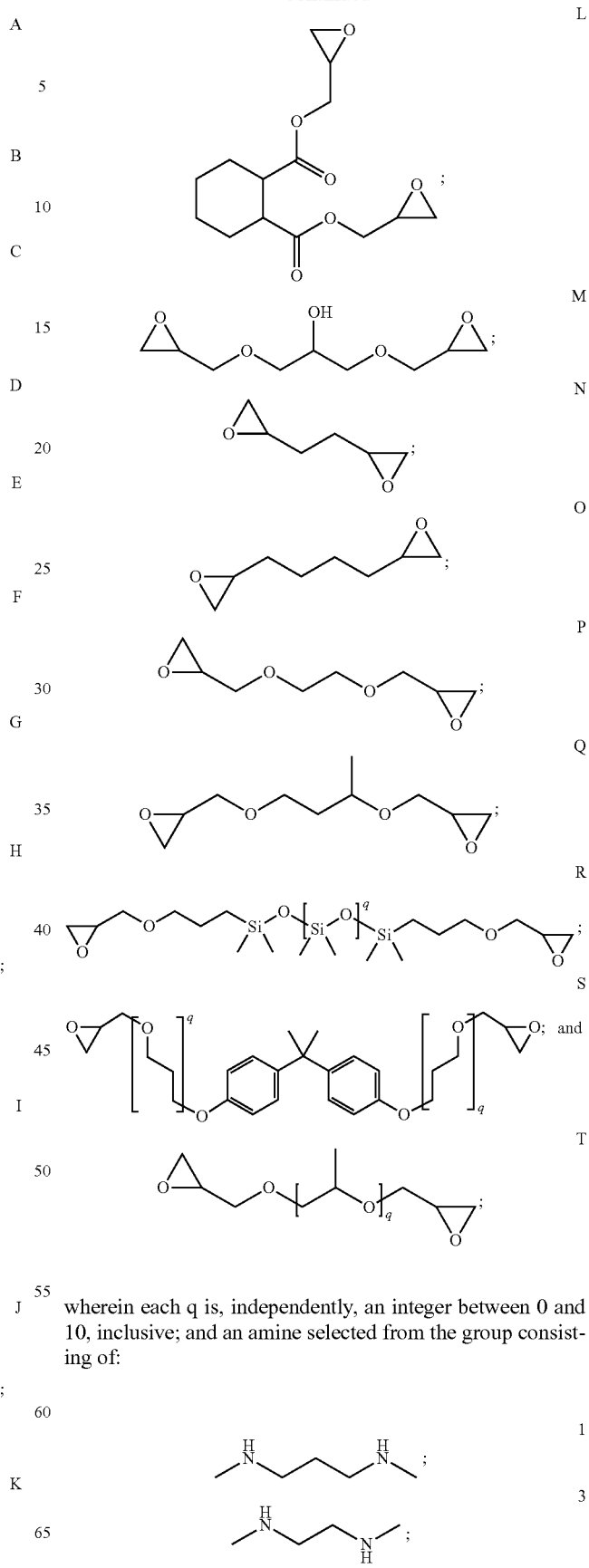
wherein each q is, independently, an integer between 0 and 10, inclusive; and an amine selected from the group consisting of:

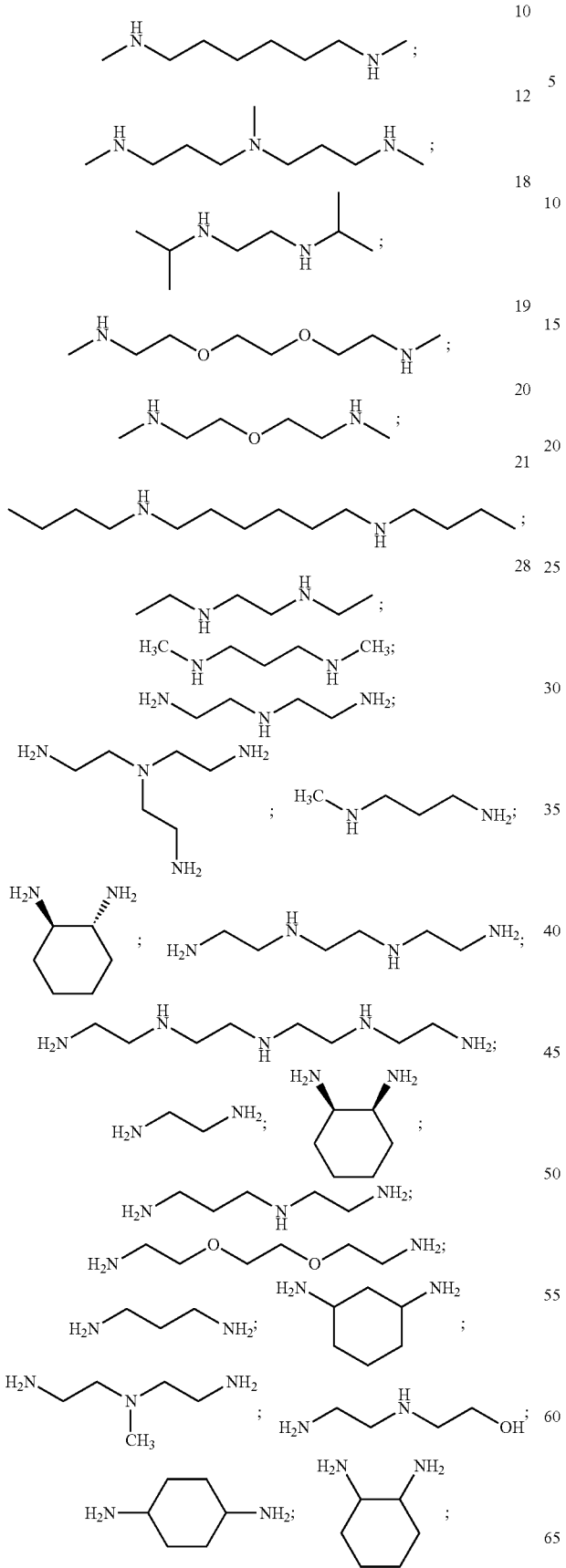
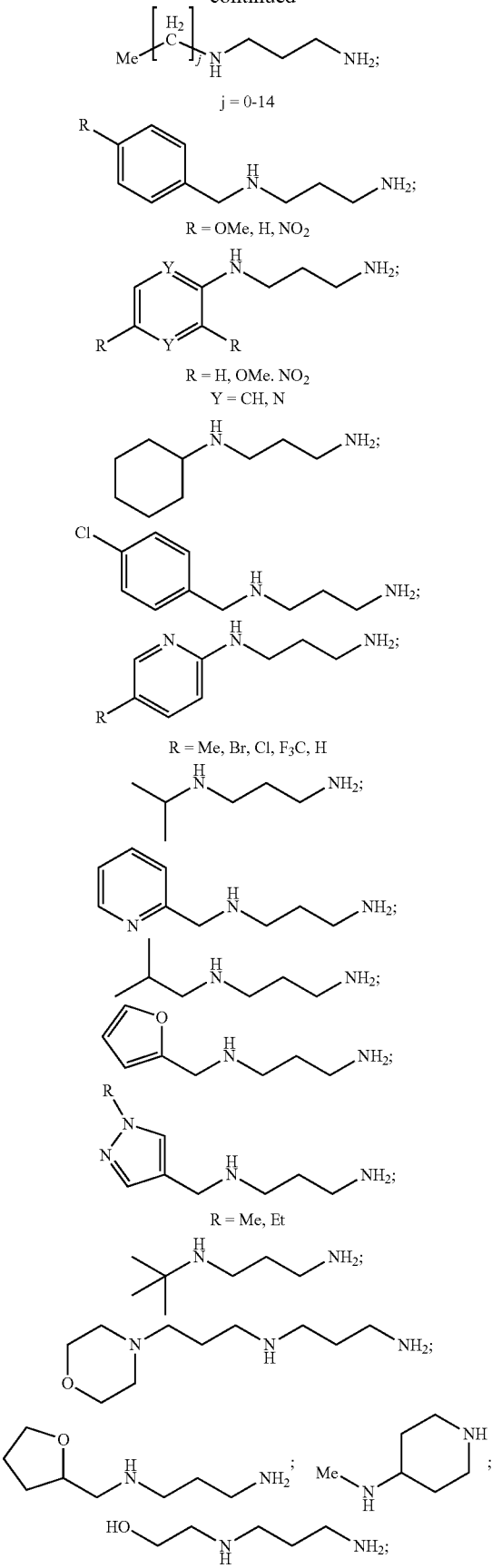

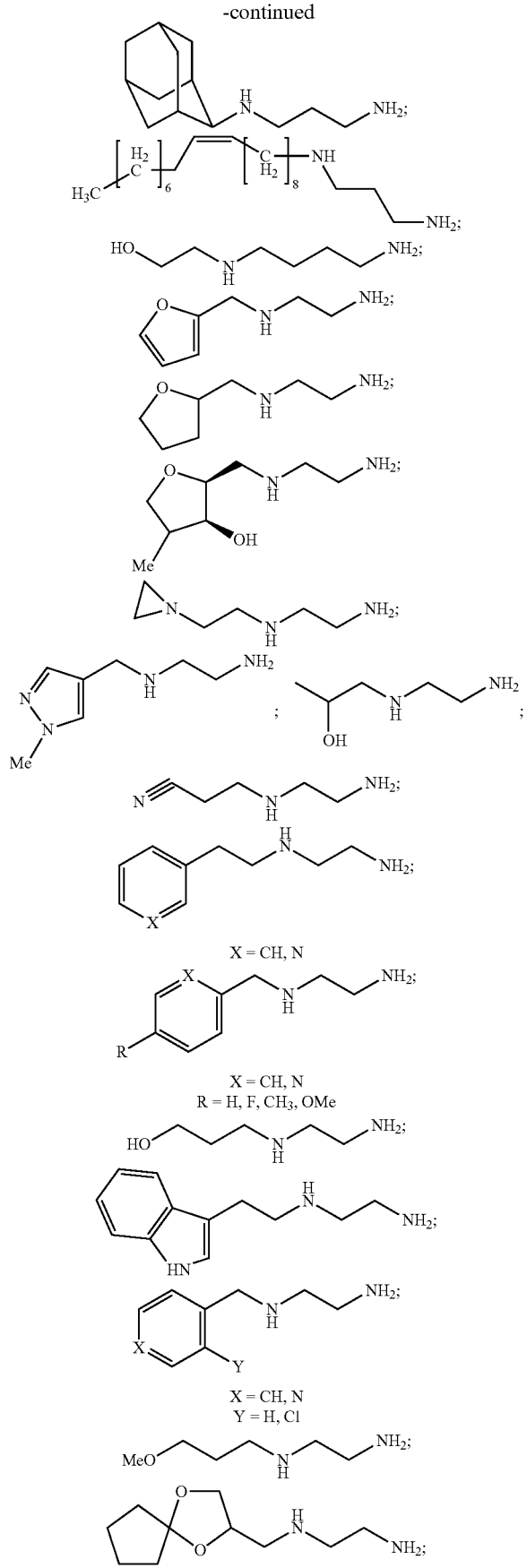
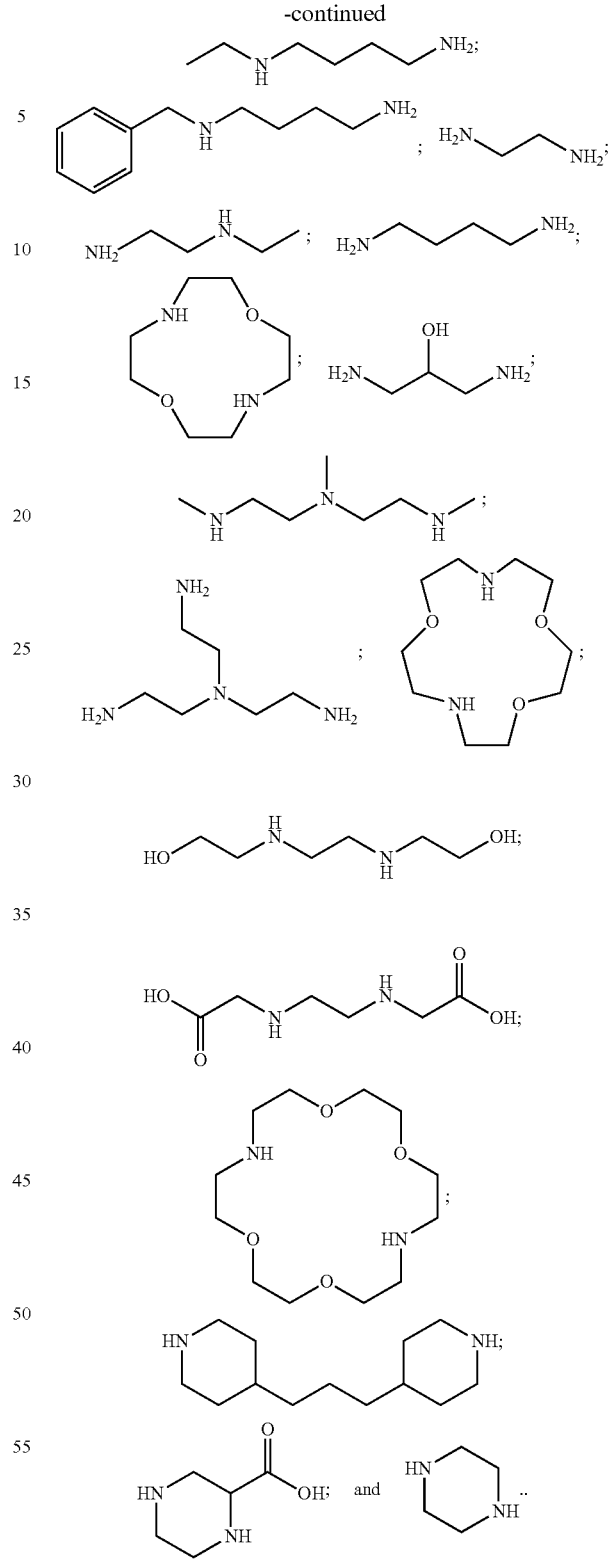
In certain embodiments, the poly(beta-amino alcohol) is selected from the group consisting of: F18, C01, F28, E19, B20, D19, A03, A01, F12, A28, B19, A19, B01, A20, F19, F10, F20, B12, A10, and A12. In certain embodiments, the polymer is selected from the group consisting of: A10, A12, B12, and B20.

In some aspects, the poly(beta-amino alcohols) of the present invention is of the formula:

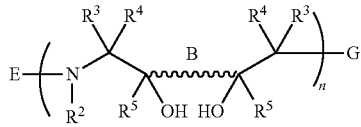

wherein:

B is a bond; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; substituted or unsubstituted aryl; or a substituted or unsubstituted heteroaryl;

$R^2$ is hydrogen; a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; substituted or unsubstituted aryl; or a substituted or unsubstituted heteroaryl;

each $R^3$ and $R^4$ is hydrogen, a substituted or unsubstituted, branched or unbranched, cyclic or acyclic $C_{1-20}$ aliphatic; a substituted or unsubstituted, branched or unbranched, cyclic or acyclic $C_{1-20}$ heteroaliphatic; a substituted or unsubstituted aryl; or a substituted or unsubstituted heteroaryl;

each

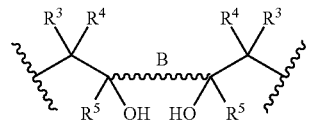

may optionally form a cyclic structure;

each E and G is, independently, hydrogen, $C_1$-$C_6$ alkyl,

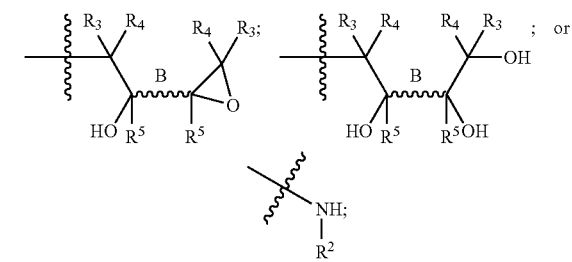

and n is an integer from 2 to 10,000, inclusive; or a salt thereof.

In certain embodiments, B is substituted or unsubstituted, branched or unbranched, cyclic or acyclic $C_{1-20}$ aliphatic. In certain embodiments, B is substituted or unsubstituted, branched or unbranched, cyclic or acyclic $C_{1-20}$ heteroaliphatic. In certain embodiments, B is a substituted or unsubstituted aryl. In certain embodiments, B is a substituted or unsubstituted heteroaryl. In certain embodiments, B is substituted or unsubstituted, branched or unbranched, cyclic or acyclic $C_{1-20}$ alkylene. In certain embodiments, B is selected from the group consisting of:

a bond,

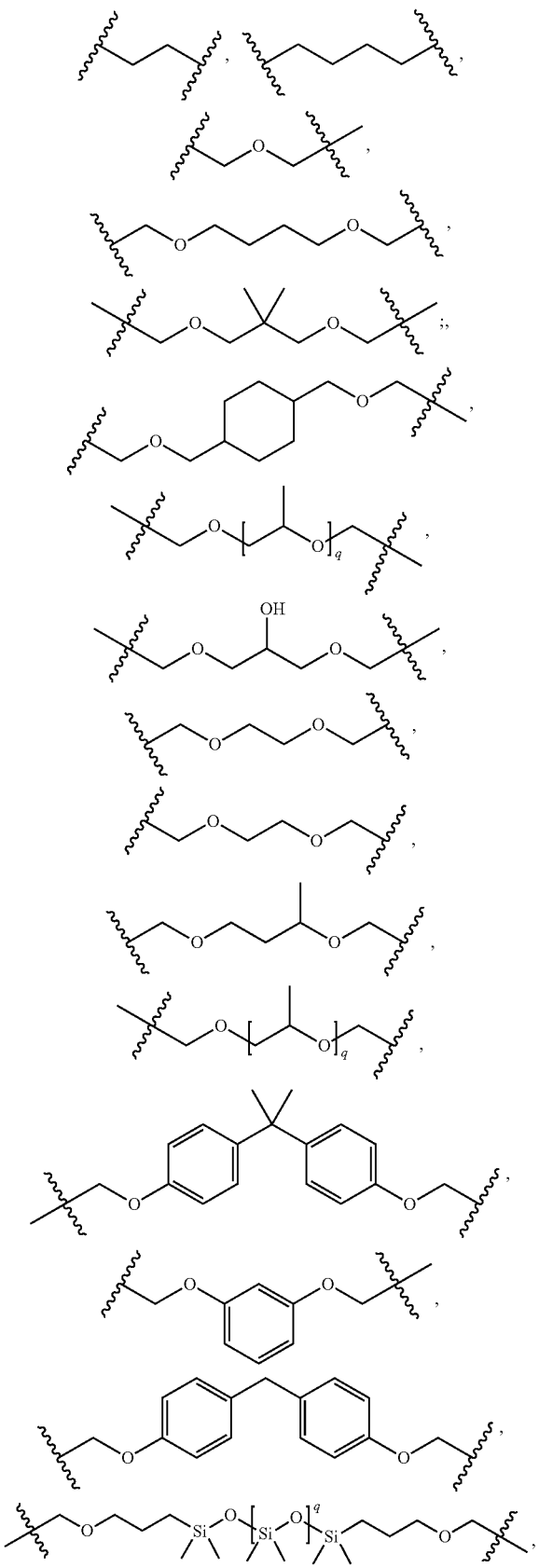

-continued

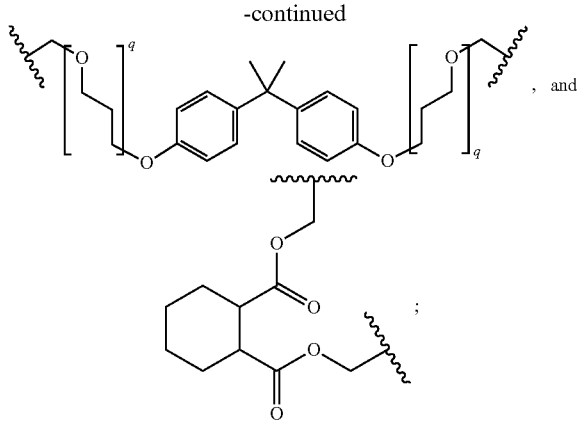

wherein each q is, independently, an integer between 0 and 10, inclusive.

In certain embodiments, $R^2$ is substituted or unsubstituted, branched or unbranched, cyclic or acyclic $C_{1-20}$ aliphatic. In certain embodiments, $R^2$ is substituted or unsubstituted, branched or unbranched, cyclic or acyclic $C_{1-20}$ heteroaliphatic. In certain embodiments, $R^2$ is substituted or unsubstituted aryl. In certain embodiments, $R^2$ is substituted or unsubstituted heteroaryl. In certain embodiments, $R^2$ is substituted or unsubstituted, branched or unbranched, cyclic or acyclic $C_{1-20}$ alkylene. In certain embodiments, $R^2$ is $C_1$-$C_6$ alkyl. In certain embodiments, $R^2$ is hydroxyalkyl. In certain embodiments, $R^2$ is aminoalkyl. In certain embodiments, $R^2$ is methyl. In certain embodiments, $R^2$ is hydrogen. In certain embodiments, $R^2$ is selected from the group consisting of:

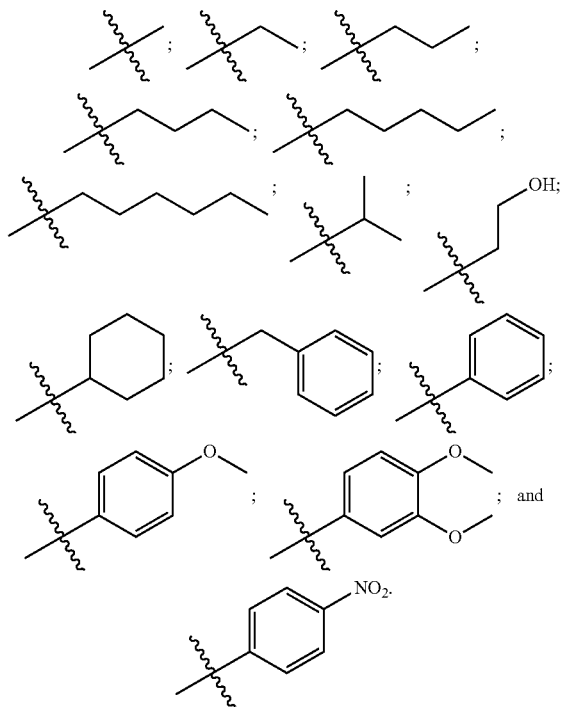

In certain embodiments, each $R^3$, $R^4$, and $R^5$ is hydrogen or an independently substituted or unsubstituted, branched or unbranched, cyclic or acyclic $C_{1-20}$ aliphatic. In certain embodiments, each $R^3$, $R^4$, and $R^5$ is hydrogen or an independently branched $C_1$-$C_{20}$ aliphatic. In certain embodiments, each $R^3$, $R^4$, and $R^5$ is hydrogen or an independently unbranched $C_1$-$C_{20}$ aliphatic. In certain embodiments, each $R^3$, $R^4$, and $R^5$ is hydrogen or an independently fluorinated $C_1$-$C_{20}$ aliphatic. In certain embodiments, each $R^3$, $R^4$, and $R^5$ is hydrogen or an independently substituted or unsubstituted, branched or unbranched, cyclic or acyclic $C_{1-20}$ heteroaliphatic. In certain embodiments, each $R^3$, $R^4$, and $R^5$ is hydrogen or an independently substituted or unsubstituted aryl. In certain embodiments, each $R^3$, $R^4$, and $R^5$ is hydrogen or an independently substituted or unsubstituted heteroaryl. In certain embodiments, each $R^3$, $R^4$, and $R^5$ is hydrogen or an independently substituted or unsubstituted, branched or unbranched, cyclic or acyclic $C_{1-20}$ alkyl. In certain embodiments, each $R^3$, $R^4$, and $R^5$ is hydrogen or an independently substituted or unsubstituted, cyclic or acyclic, branched or unbranched $C_1$-$C_{15}$ alkyl. In certain embodiments, each $R^3$, $R^4$, and $R^5$ is hydrogen or an independently substituted or unsubstituted, cyclic or acyclic, branched or unbranched $C_1$-$C_{10}$ alkyl. In certain embodiments, each $R^3$, $R^4$, and $R^5$ is hydrogen or an independently substituted or unsubstituted, cyclic or acyclic, branched or unbranched $C_1$-$C_6$ alkyl.

In certain embodiments, all $R^3$ and $R^4$ are not hydrogen. In certain embodiments, all $R^3$ and $R^4$ are hydrogen. In certain embodiments, all $R^3$, $R^4$, and $R^5$ are not hydrogen. In certain embodiments, all $R^3$, $R^4$, and $R^5$ are hydrogen. In certain embodiments, $R^5$ is hydrogen. In certain embodiments, each $R^3$, $R^4$, and $R^5$ is independently selected from the group consisting of:

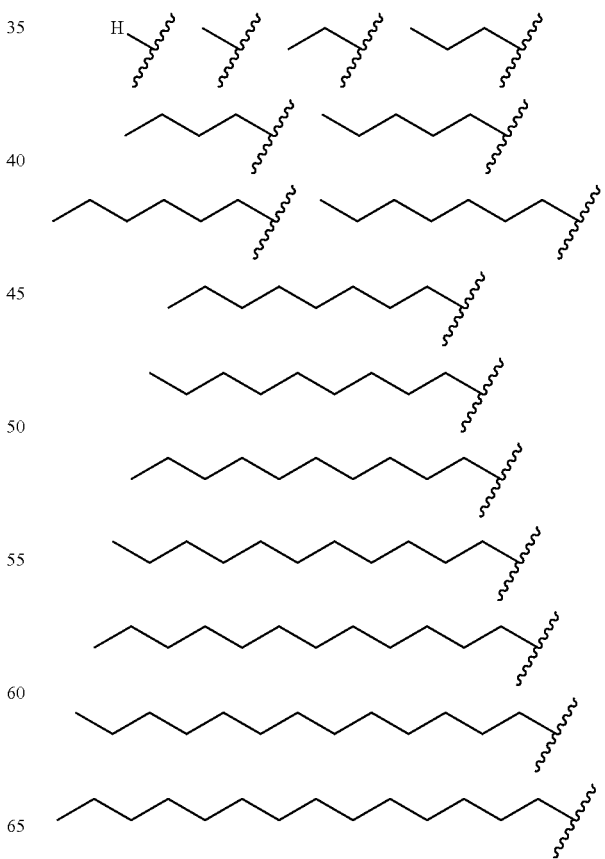

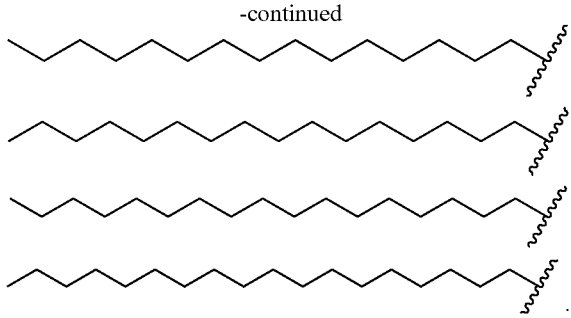

In certain embodiments, each $R^3$, $R^4$, and $R^5$ is independently hydrogen or a substituted or unsubstituted, cyclic or acyclic, branched or unbranched $C_1$-$C_{20}$ alkenyl. In certain embodiments, each $R^3$, $R^4$, and $R^5$ is independently selected from the group consisting of:

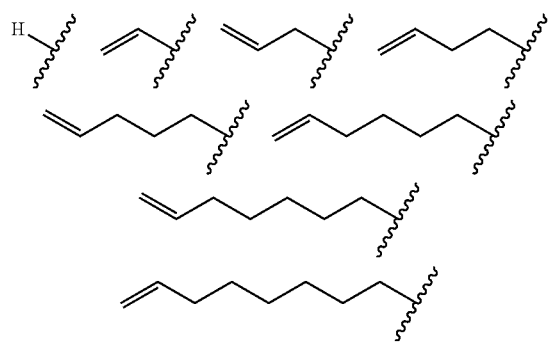

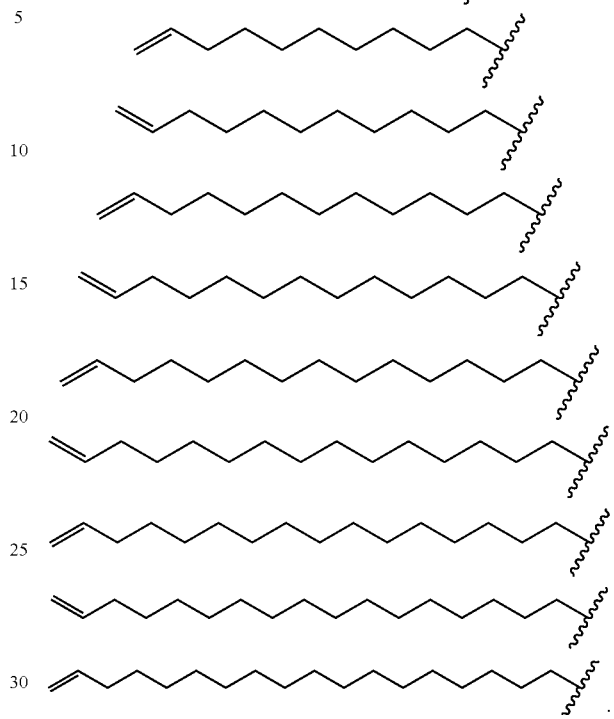

In certain embodiments, each $R^3$, $R^4$, and $R^5$ is independently selected from the group consisting of:

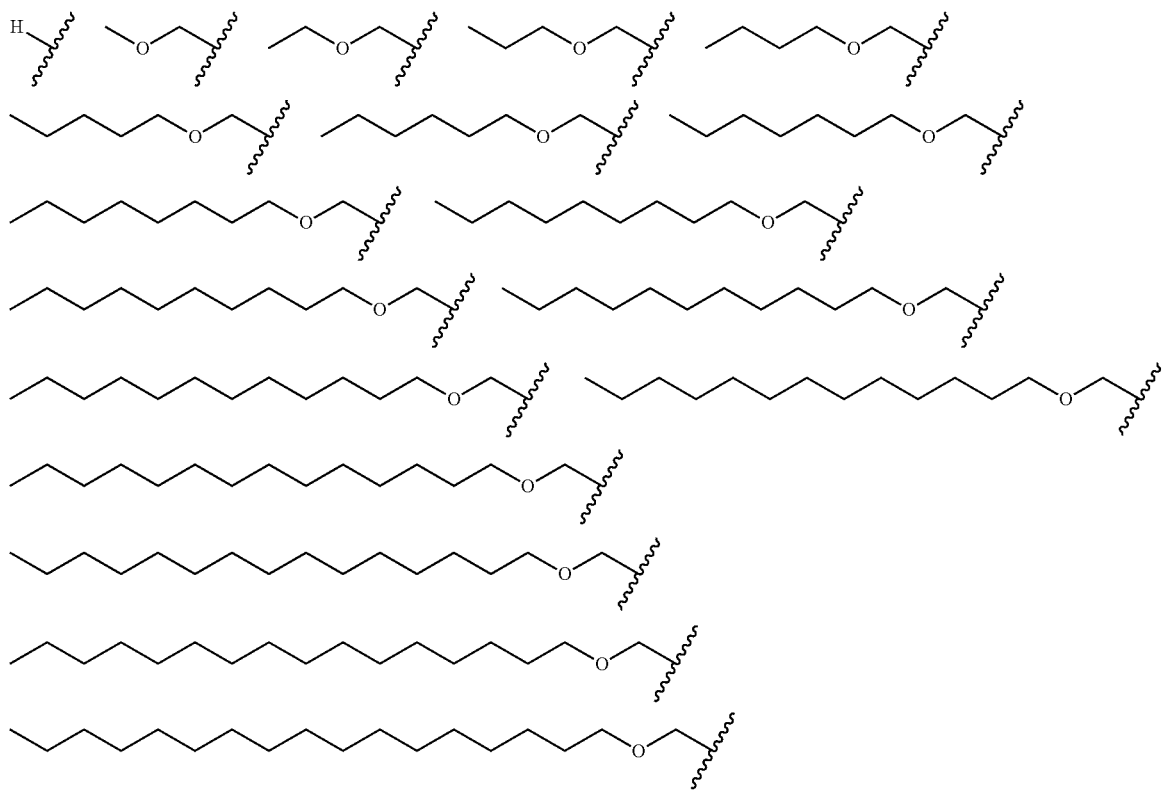

-continued
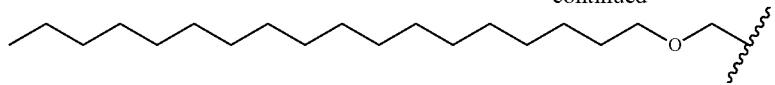
In certain embodiments, each $R^3$, $R^4$, and $R^5$ is independently selected from the group consisting of:
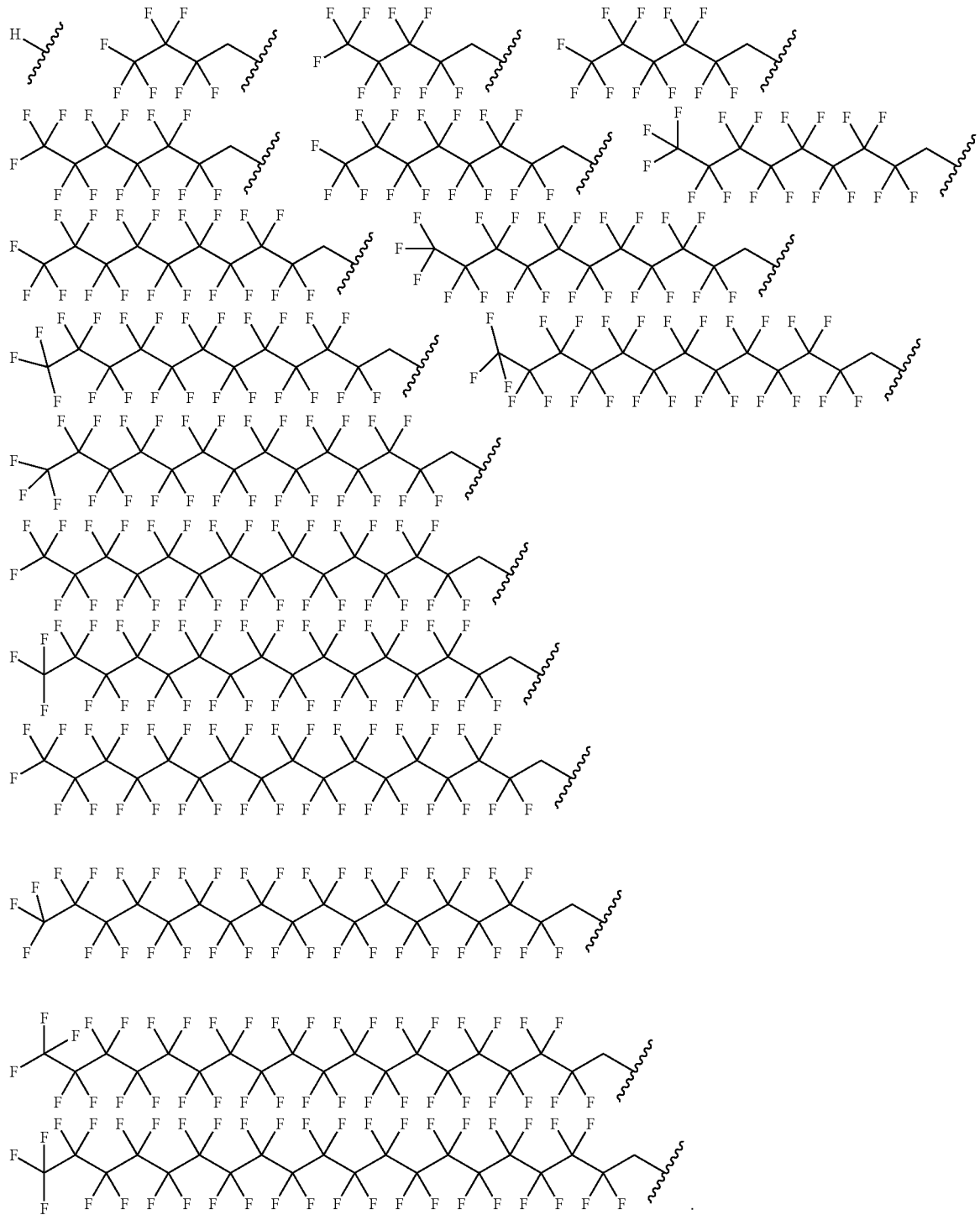

In certain embodiments all $R^3$ and $R^4$ are hydrogen. In certain embodiments, each

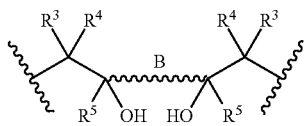

is selected from the group consisting of:

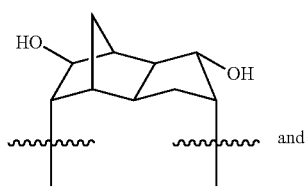

and

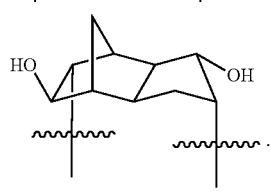

In certain embodiments, the molecular weight ranges between 1,000 and 100,000 Daltons. In certain embodiments, the molecular weight ranges between 3,000 and 70,000 Daltons. In certain embodiments, the molecular weight ranges between 5,000 and 40,000 Daltons. In certain embodiments, the molecular weight ranges between 5,000 and 30,000 Daltons. In certain embodiments, the molecular weight ranges between 5,000 and 20,000 Daltons. In certain embodiments, the molecular weight ranges between 10,000 and 20,000 Daltons.

In certain embodiments, the polymer has at least one secondary amine functional group in every repeating unit. In certain embodiments, the polymer has at least one tertiary amine functional group in every repeating unit. In certain embodiments, the polymer has at least one quaternary amine functional group in every repeating unit.

In certain embodiments, the polymer is linear. In certain embodiments, the polymer is water-soluble. In certain embodiments, the polymer is hydrolytically stable. In certain embodiments, the polymer is not biodegradable. In certain embodiments, less than 25% of the polymer is degraded after one year in vivo. In certain embodiments, less than 10% of the polymer is degraded after one year in vivo. In certain embodiments, less than 5% of the polymer is degraded after one year in vivo. In certain embodiments, less than 1% of the polymer is degraded after one year in vivo. In certain embodiments, less than 25% of the polymer is degraded after five years in vivo. In certain embodiments, less than 10% of the polymer is degraded after five years in vivo. In certain embodiments, less than 5% of the polymer is degraded after five years in vivo. In certain embodiments, less than 1% of the polymer is degraded after five years in vivo.

In some aspects, the poly(beta-amino alcohol) of the present invention is prepared from an diepoxide selected from the group consisting of:

A
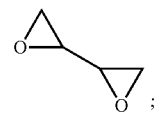

B
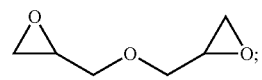

C
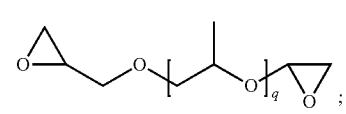

D
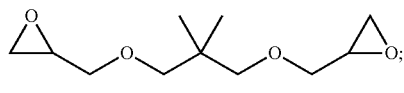

E
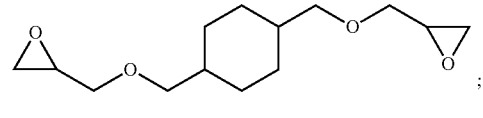

F
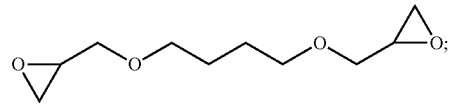

G
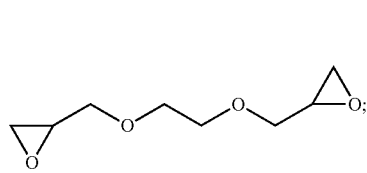

H
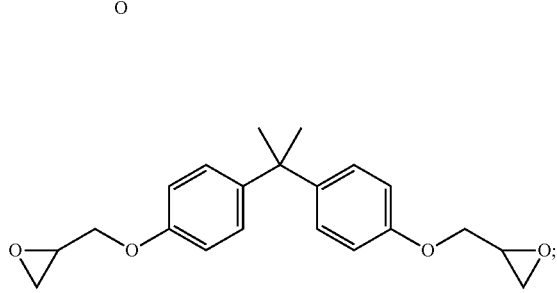

I
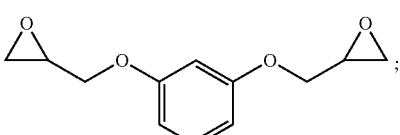

J
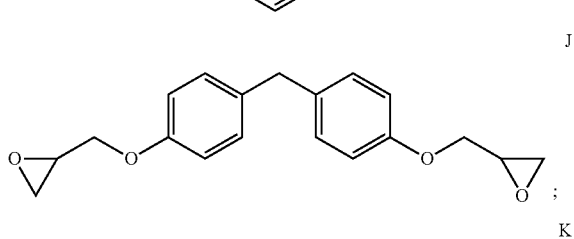

K

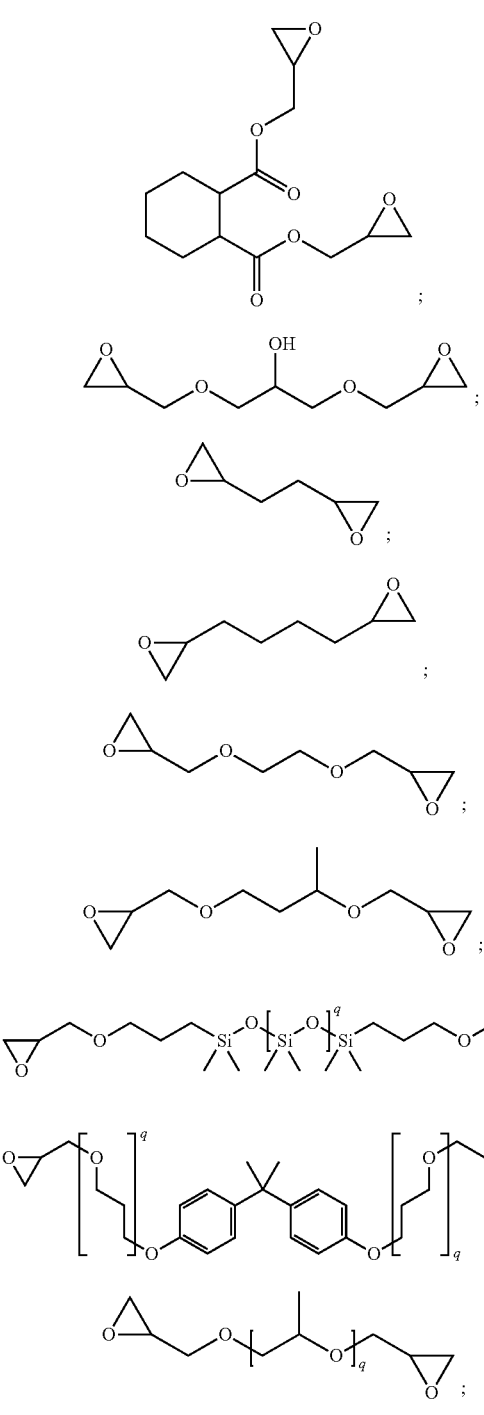
each q is, independently, an integer between 0 and 10, inclusive; and an amine selected from the group consisting of:
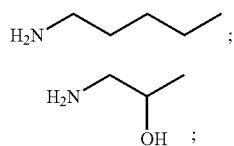
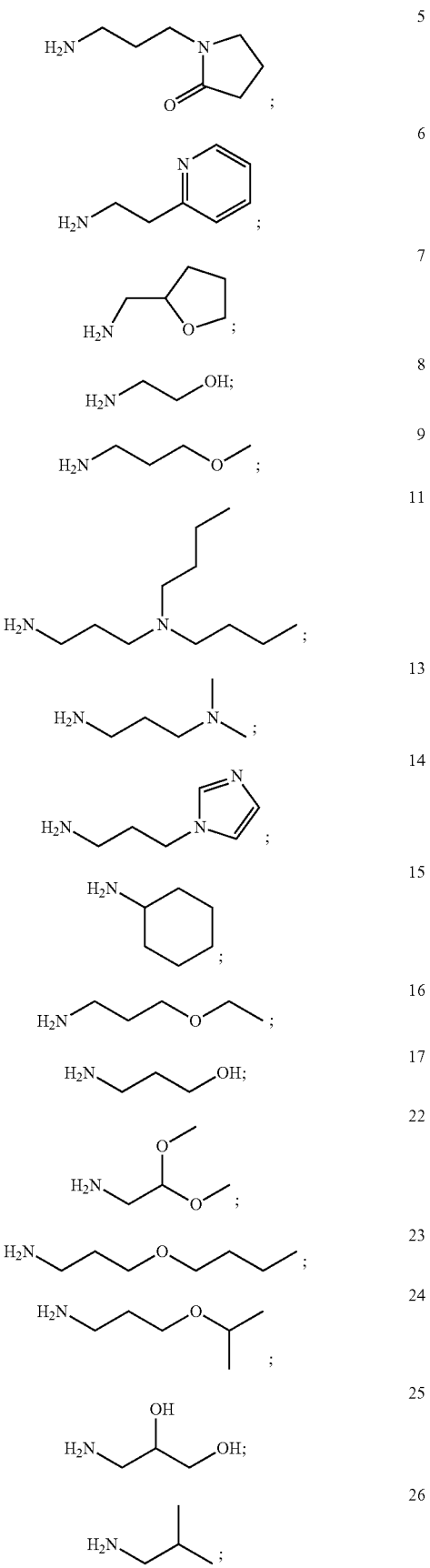

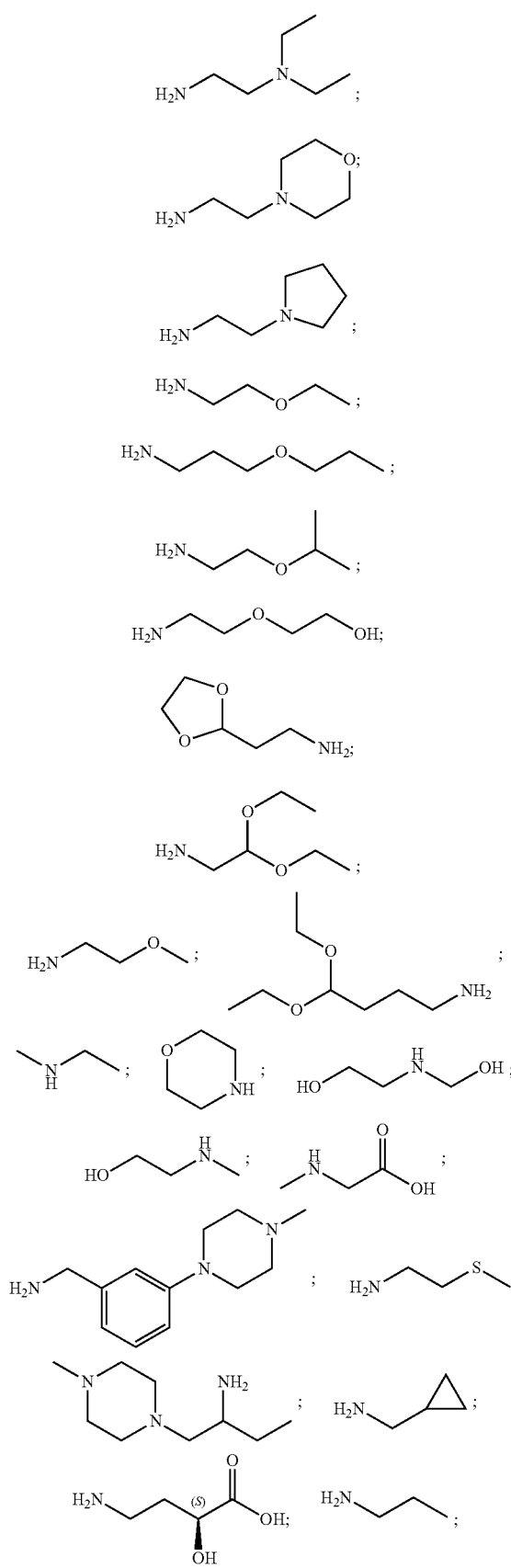
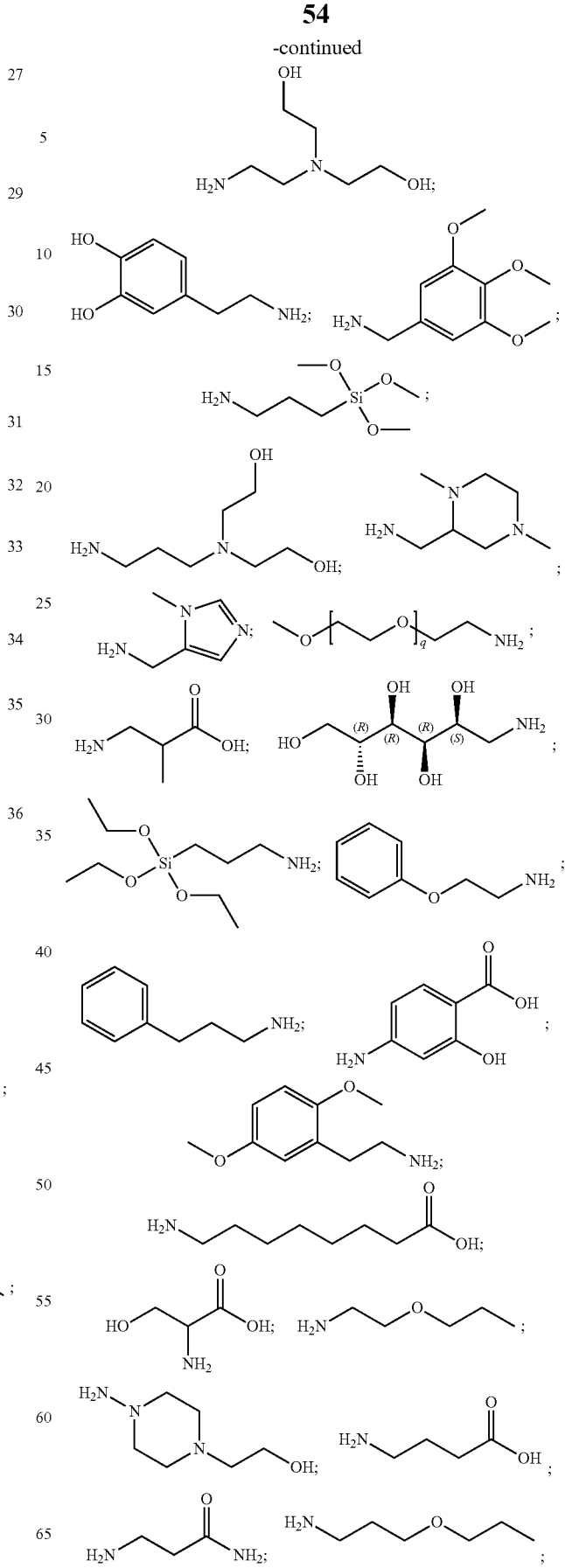

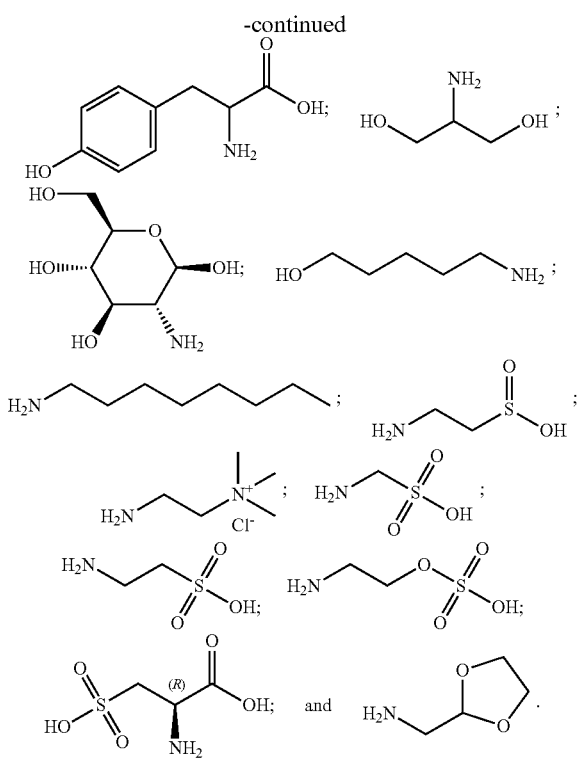

In certain embodiments, the poly(beta-amino alcohol) is selected from the group consisting of: A35, B35, A36, B36, D22, E22, E35, E36, E09, A34, F35, A29, F09, F32, D20, C22, A06, A32, F22, F06, B09, B33, E08, F26, D16, F05, C24, A33, B11, E25, A05, B34, B29, A24, B24, B26, F34, F31, F17, F36, A09, C25, B31, A11, B07, F16, A31, A23, F29, B04, A16, C13, F23, F33, B03, A17, B28, B14, A08, F27, A27, B27, A30, and B30. In certain embodiments, the poly(beta-amino alcohol) is B30.

Some aspects of the invention include a liposome comprising any one of the poly(beta-amino alcohols) of the invention and an agent to be delivered, wherein the agent is selected from the group consisting of a polynucleotide, RNA, a small molecule, a drug, a peptide, or a gas. In certain embodiments, the liposome ranges in size from 10 nanometers to 2000 nanometers.

Some aspects of the invention include any one of the poly(beta-amino alcohols) of the invention and an agent to be delivered. Some aspects of the invention include a device coated with a poly(beta-amino alcohols) of the invention. Some aspects of the invention include an implant coated with a poly(beta-amino alcohols) of the invention. Some aspects of the invention include a surface coated with a poly(beta-amino alcohols) of the invention. Some aspects of the invention include a micelle coated with a poly(beta-amino alcohols) of the invention. Some aspects of the invention include a complex comprising a poly(beta-amino alcohols) of the invention and a polynucleotide. Some aspects of the invention include a method of administering an agent, the method comprising step of administering to a subject in need thereof a therapeutically effective amount of a pharmaceutical composition comprising a poly(beta-amino alcohols) of the invention; and an agent to be delivered.

Some aspects of the invention include a method of encapsulating an agent in a matrix of a poly(beta-amino alcohols) of the invention to form microparticles, the method comprising steps of:

providing an agent;
providing a poly(beta-amino alcohols) of the invention; and
contacting the agent and the polymer under suitable conditions to form microparticles.

In certain embodiments, the microparticles inhibit an immune response. In certain embodiments, the microparticles inhibit monocyte and/or macrophage activation. In certain embodiments, the microparticles regulate a foreign body response. In certain embodiments, the microparticles regulate a cell-material interaction. In certain embodiments, the microparticles inhibit the biosynthesis of TNF-α. In certain embodiments, the microparticles deliver a nucleic acid. In certain embodiments, the nucleic acid is DNA. In certain embodiments, the nucleic acid is siRNA. In certain embodiments, the microparticles modify a cell-material interaction. In certain embodiments, the microparticles modify protein adhesion. In certain embodiments, the microparticles modify cell adhesion. In certain embodiments, the microparticles modify proliferation, differentiation, or proliferation and differentiation. In certain embodiments, the microparticles modify coagulation.

Some aspects of the invention include a method of coating a substrate with a polymer of any one of claims 1-3x, the method comprising steps of:

providing an substrate;
providing a poly(beta-amino alcohols) of the invention; and
contacting the substrate and the polymer under suitable conditions to form a coating.

In certain embodiments, the coating is antimicrobial. In certain embodiments, the coating is a layer-by-layer (LBL) coating. In certain embodiments, the coating is a thin film. In certain embodiments, the coating is a superstructure. In certain embodiments, the coating is a polyelectrolyte complex capsule. In certain embodiments, the polyelectrolyte complex capsule is semi-permeable. In certain embodiments, the coating is an antifoulant.

Synthesis of Poly(Beta-amino Alcohols)

Poly(beta-amino alcohols) may be prepared by any method known in the art. The polymers may be made, for example, by a step-growth polymerization of a diepoxide and a bis-secondary amine or a primary amine. Also, two different diepoxide compounds and/or two different amine components may be used in the reaction mixture to prepare the poly(beta-amino alcohol). The epoxide-amine reaction is generally very robust and efficient even at room temperature. Similar step growth polymerizations were used to make epoxy-based thermoplastics (J. E. White, H. C. Silvis, M. S. Winkler, T. W. Glass, D. E. Kirkpatrick, *Adv. Mater.* 2000, 12, 1791; J. E. White, J. Earls, J. W. Sherman, L. C. Lopez, M. L. Dettloff, *Polymer* 2007, 48, 3990; both incorporated herein by reference) and copoly(carbosiloxanes) (M. A. Grunlan, N. S. Lee, W. P. Weber, *Polymer* 2004, 45, 2517; incorporated herein by reference.)

Some aspects of the invention include a method of preparing a poly(beta-amino alcohol); the method comprising the step of reacting an amine of the formula:

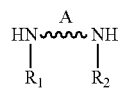

with a diepoxide of the formula:

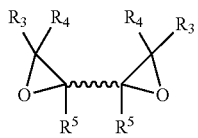

to form a polymer of formula:

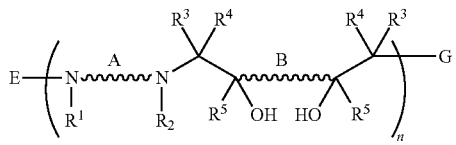

wherein $R^1$, $R^2$, $R^3$, $R^4$, $R^5$, A, B, n, E, and G are as defined herein.

In certain embodiments, the poly(beta-amino alcohol) is made by step-growth polymerization. In certain embodiments, the step of reacting is performed in the absence of solvent. In certain embodiments, the step of reacting is performed in the presence of an aprotic solvent. In certain embodiments, the solvent is tetrahydrofuran, diethyl ether, ethyl acetate, DMSO, DMF, methanol, ethanol, or water. In certain embodiments, the reacting step is performed between about 25° C. and about 50° C. In certain embodiments, the method of preparing a poly(beta-amino alcohol) further comprises the step of purifying the product.

Some aspects of the invention include a method of preparing a poly(beta-amino alcohol); the method comprising the step of reacting one or more equivalents of an amine of the formula:

with a diepoxide of the formula:

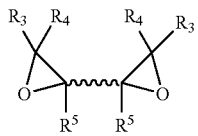

to form a polymer of the formula:

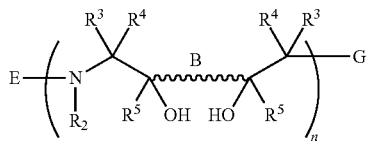

wherein $R^2$, $R^3$, $R^4$, $R^5$, B, n, E, and G are as defined herein.

In certain embodiments, the poly(beta-amino alcohol) is made by step-growth polymerization. In certain embodiments, the step of reacting is performed in the presence of an aprotic solvent. In certain embodiments, the solvent is tetrahydrofuran, diethyl ether, ethyl acetate, DMSO, DMF, methanol, ethanol or water. In certain embodiments, the reacting step is performed between 25° C. and 50° C. In certain embodiments, the method of preparing a poly(beta-amino alcohol) further comprises the step of purifying the product.

The polymers were made by a step-growth polymerization of a diepoxide and a bis-secondary amine or a primary amine. The epoxide-amine reaction is generally very robust and efficient even at room temperature. Similar step growth polymerizations were used to make epoxy-based thermoplastics (J. E. White, H. C. Silvis, M. S. Winkler, t. W. Glass, D. E. Kirkpatrick, *Adv. Mater.* 2000, 12, 1791; J. E. While, J. Earls, J. W. Sherman, L. C. Lopez, M. L. Dettloff, *Polymer* 2007, 48, 3990) and copoly(carbosiloxanes) (M. A. Grunlan, N. S. Lee, W. P. Weber, *Polymer* 2004, 45, 2517). The general structures of the monomers and polymers are shown below in the General Scheme. These polymers have several advantages as potential coatings to regulate the foreign body responses as well as cell-material interactions in general. First, they are hydrolytically stable and hydrophilic due to the abundant hydroxyl groups. Hydrophilicity has been recognized as an important characteristic of biomaterials with low protein adsorption or cell adhesion (E. Ostuni, R. G. Chapman, R. E. Holmlin, S. Takayama, G. M. Whitesides, *Langmuir* 2001, 17. 5605;. N. A. Peppas, J. Z. Hilt, A. Khademhosseini, R. Langer, *Adv. Mater.* 2006, 18, 1345). The non-biofouling properties of oligo(ethylene glycol)-terminated self-assembled monolayers (SAMs) (P. Harder, M. Grunze, R. Dahint, G. M. Whitesides, P. E. Laibinis, *J. Phys. Chem. B* 1998, 102, 426), zwitterionic SAMs (R. E. Holmlin, X. Chen, R. G. Chapman, S. Takayama, G. M. Whitesides, *Langmuir* 2001, 17, 2841) and polymers (S. Jiang, Z. Cao, *Adv. Mater.* 2010, 22, 920) have been mainly attributed to their surface hydration. Second, their synthesis is relatively simple and no solvent, high temperature, catalyst or additional chemicals are required. Because of their water-solubility and cationic nature, the polymers can be easily immobilized onto a wide range of negatively charged surfaces under biologically-friendly conditions through electrostatic interactions. The mild coating conditions are particularly useful for coating medical devices that are sensitive to heat, UV light, or organic solvents. Lastly, the availability of a large number of monomers allows one to screen extremely diverse surface chemistries for different biological applications.

Depending on the specific structures of the monomers and reaction conditions, the typical weight averaged molecular weights (MW) of the polymers ranged from 7,000 Dalton to 25,000 Dalton with polydispersity (PDI) of 1.5 to 2.5. The $^1$H NMR spectra of selected polymers exhibited clear peak broadening, typical of polymers. Two common chemical shift (ppm) ranges were around δ 2.2-δ 2.8 (characteristic range of H connected to α C next to N) and δ 3.2-δ 3.8 (characteristic range of H connected to α C next to —OH). The polymers were generally soluble in water or slightly acidic solutions with pH around 4 to 6. The polymers that were insoluble or formed hydrogels in water were eliminated for further study. FIG. 5(*b*) shows the chemical structures of the 6 epoxides and 36 amines that were chosen to make the polymers. 176 of these polymers were used for subsequent in vitro screening.

The polymers were made by a step-growth polymerization of a diepoxide and a bis-secondary amine or a primary amine. The epoxide-amine reaction is generally very robust and efficient even at room temperature. Similar step growth polymerizations were used to make epoxy-based thermoplastics (J. E. White, H. C. Silvis, M. S. Winkler, T. W. Glass, D. E. Kirkpatrick, *Adv. Mater.* 2000, 12, 1791; J. E. White, J. Earls, J. W. Sherman, L. C. Lopez, M. L. Dettloff, *Polymer* 2007, 48, 3990) and copoly(carbosiloxanes) (M. A. Grunlan, N. S. Lee, W. P. Weber, *Polymer* 2004, 45, 2517). The general structures of the monomers and polymers are shown below in the General Scheme. These polymers have several advantages as potential coatings to regulate the foreign body responses as well as cell-material interactions in general. First, they are hydrolytically stable and hydrophilic due to the abundant hydroxyl groups. Hydrophilicity has been recognized as an important characteristic of biomaterials with low protein adsorption or cell adhesion (E. Ostuni, R. G. Chapman, R. E. Holmlin, S. Takayama, G. M. Whitesides, *Langmuir* 2001, 17. 5605; N. A. Peppas, J. Z. Hilt, A. Khademhosseini, R. Langer, *Adv. Mater.* 2006, 18, 1345). The non-biofouling properties of oligo(ethylene glycol)-terminated self-assembled monolayers (SAMs) (P. Harder, M. Grunze, R. Dahint, G. M. Whitesides, P. E. Laibinis, *J. Phys. Chem. B* 1998, 102, 426), zwitterionic SAMs (R. E. Holmlin, X. Chen, R. G. Chapman, S. Takayama, G. M. Whitesides, *Langmuir* 2001, 17, 2841) and polymers (S. Jiang, Z. Cao, *Adv. Mater.* 2010, 22, 920) have been mainly attributed to their surface hydration. Second, their synthesis is relatively simple and no solvent, high temperature, catalyst or additional chemicals are required. Because of their water-solubility and cationic nature, the polymers can be easily immobilized onto a wide range of negatively charged surfaces under biologically-friendly conditions through electrostatic interactions. The mild coating conditions are particularly useful for coating medical devices that are sensitive to heat, UV light, or organic solvents. Lastly, the availability of a large number of monomers allows one to screen extremely diverse surface chemistries for different biological applications.

A large number of chemically diverse polymers can be obtained through the variation of substituents $R^1$, $R^2$, $R^3$, $R^4$, $R^5$, A, B, E, and G as shown below. Depending on the specific structures of the monomers and reaction conditions, the typical weight averaged molecular weights (MW) of the polymers ranged from 7,000 Dalton to 25,000 Dalton with polydispersity (PDI) of 1.5 to 2.5. The $^1$H NMR spectra of selected polymers exhibited clear peak broadening, typical of polymers. Two common chemical shift (ppm) ranges were around δ 2.2-δ 2.8 (characteristic range of H connected to α C next to N) and δ 3.2-δ 3.8 (characteristic range of H connected to α C next to —OH). The polymers were generally soluble in water or slightly acidic solutions with pH around 4 to 6. The polymers that were insoluble or formed hydrogels in water were eliminated for further study. The chemical structures of exemplary epoxides (e.g., epoxides A to T) and amines (e.g., amines 1 to 36) chosen to make polymers of the present invention are shown below. 176 of these polymers were used for subsequent in vitro screening (see the Examples, below).

General scheme of step-growth polymerization

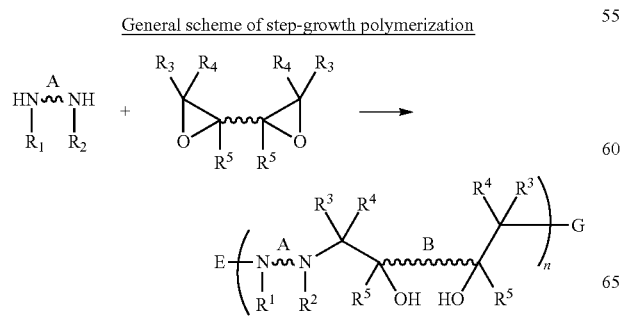

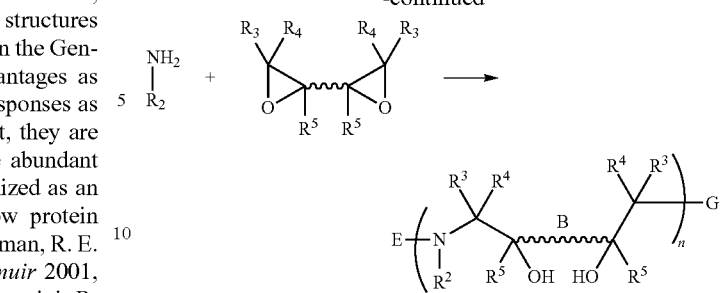

Exemplary Epoxide Monomers Used to Make PBAAS

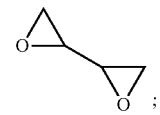
A

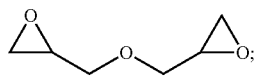
B

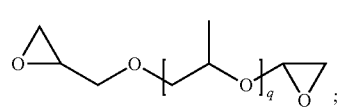
C

D

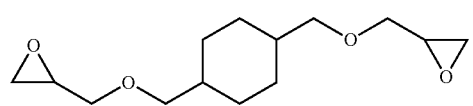
E

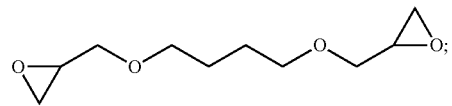
F

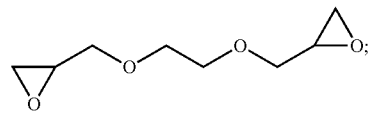
G

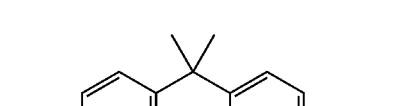
H

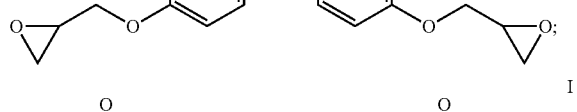
I

-continued
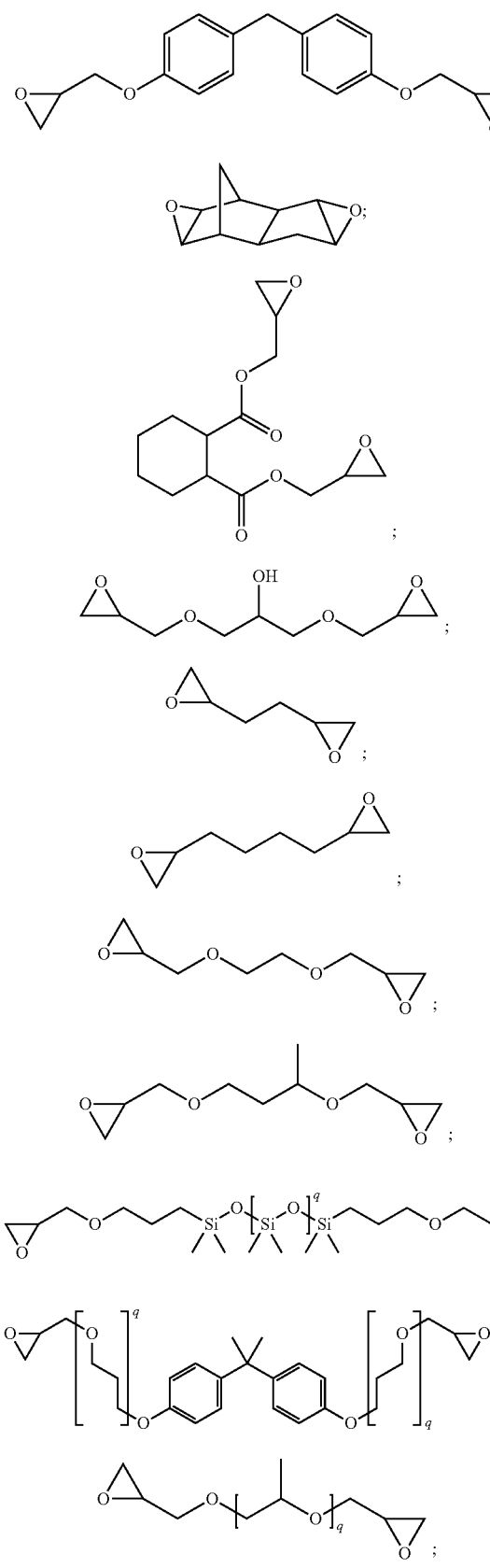
wherein each q is, independently, an integer between 0 and 10, inclusive.
Exemplary Amine Monomers Used to Make PBAAS
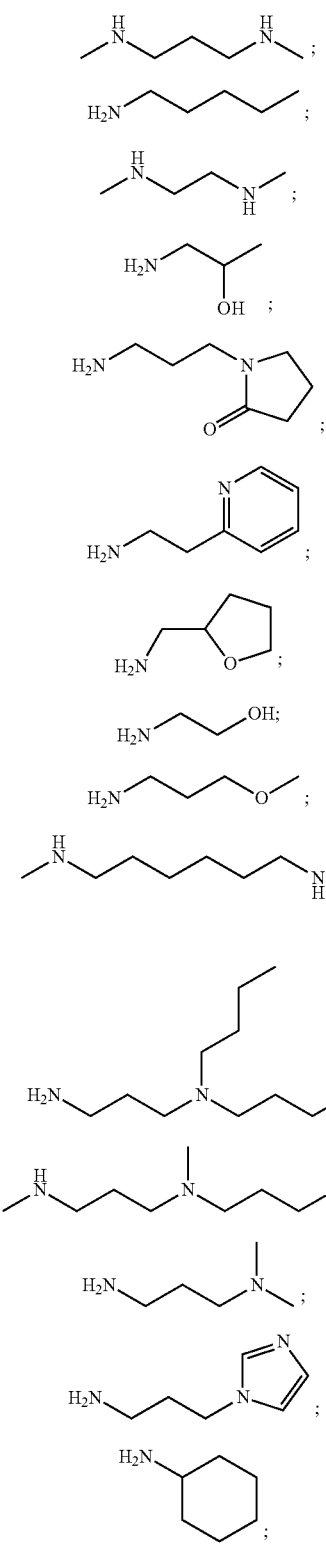

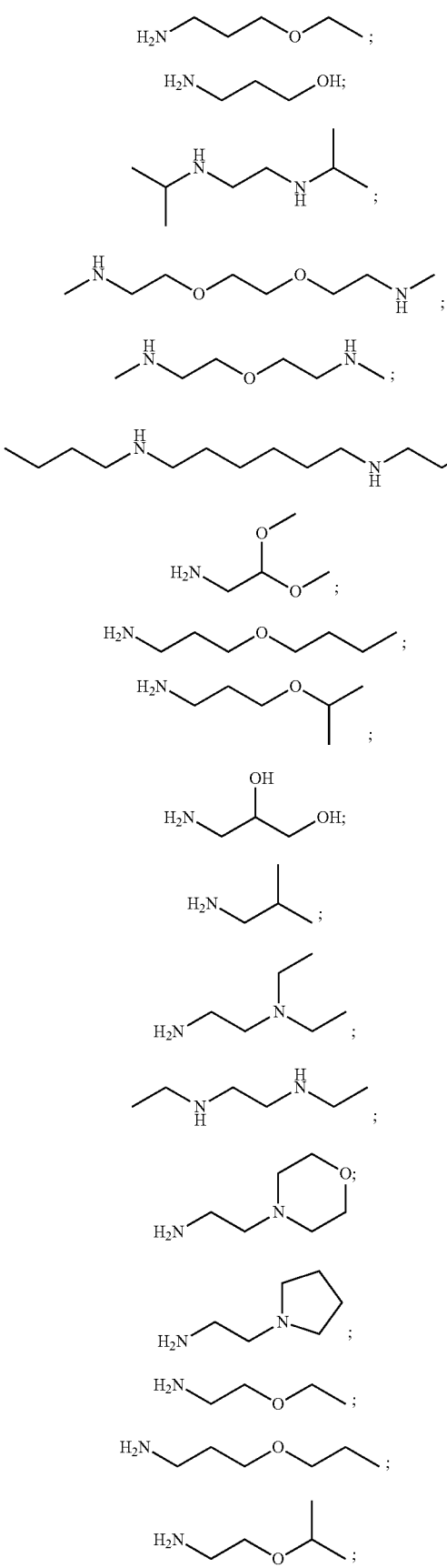

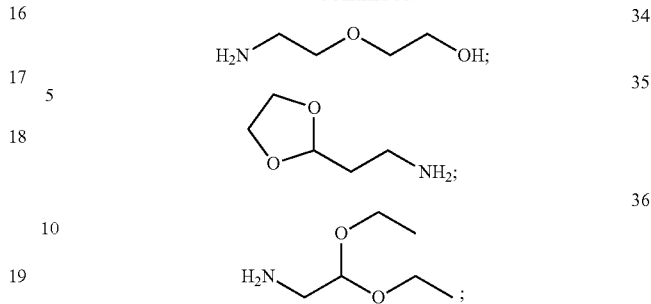

Preferably the poly(beta-amino alcohols) are prepared from commercially available starting materials, such as diepoxides and amines. In another embodiment, the poly(beta-amino alcohols) are prepared from easily and/or inexpensively prepared starting materials. As would be appreciated by one of skill in the art, the inventive poly(beta-amino alcohols) can be prepared by total synthesis starting from commercially available starting materials. A particular poly(beta-amino alcohols) may be the desired final product of the synthesis, or a mixture of poly(beta-amino alcohols) may be the desired final product.

Any amine containing between one, two, three, four, and five amine functionalities is useful in preparing inventive poly(beta-amino alcohols). Primary amines useful in this invention include, but are not limited to, methylamine, ethylamine, isopropylamine, aniline, substituted anilines, ethanolamine, decylamine, undecylamine, dodecylamine, tetradecylamine, hexadecylamine, and octadecylamine. The amine may be a bis(primary amine) including, but not limited to, ethylenediamine, 1,3diaminopropane, 1,4diamino butane, 1,5diaminopentane, 1,6diaminohexane, and 2,2' (ethylenedioxy)bis(ethylamine). The amine may be a bis(secondary amine). Secondary amines useful in this invention include, but are not limited to, dipropylamine and methylpentylamine. The amine may include both primary and secondary amines including, but not limited to, (2-aminoethyl)ethanolamine, diethylenetriamine, and triethylenetetramine. Preferably, the amine is commercially available. In certain embodiments, the amine is stereochemically pure (e.g., enantiomerically pure).

Diepoxides that are useful in the present invention include racemic compounds or stereoisomers thereof, all of varying chain lengths and feature unique functional groups having varying degrees of saturation. In certain embodiments, the diepoxide is stereochemically pure (e.g., enantiomerically pure). In certain embodiments, the diepoxide contains one or more chiral centers. In certain embodiments, the epoxides are of the formula A through O as shown above.

The chiral epoxides useful in the invention can be obtained from a variety of sources which are familiar to those skilled in the art of organic synthesis. In some embodiments, the chiral epoxides useful in the invention can be obtained commercially. In some embodiments, the chiral epoxides useful in the invention can be synthesized according to methods known to those of skill in the art, such as, but not limited to the Sharpless epoxidation of primary and secondary allylic alcohols into 2,3-epoxyalcohols (Katsuki et al., *J. Am. Chem. Soc.* 1980, 102, 5974; Hill et al., *Org. Syn.*, Coll. Vol. 7, p. 461 (1990); Vol. 63, p. 66 (1985); Katsuki et al., *Org. React.* 1996, 48, 1-300; incorporated herein by reference.) In some embodiments, the chiral epoxides useful in the invention are obtained from the resolution of racemic epoxides. In some embodiments, the chiral epoxides useful in the invention are obtained by the separation of enantiomers or diastereoisomers using chiral chromatography.

In certain embodiments, the reaction is performed neat without the use of a solvent. In other embodiments, a solvent is used for the reaction. Both or one of the starting amine or epoxide-terminated compound is dissolved in an organic solvent (e.g., THF, $CH_2Cl_2$, MeOH, EtOH, $CHCl_3$, hexanes, toluene, benzene, $CCl_4$, glyme, diethyl ether, etc.). The resulting solutions are combined, and the reaction mixture is heated to yield the desired poly(beta-amino alcohol). In certain embodiments, the reaction mixture is heated to a temperature ranging from approx. 25° C. to approx. 100° C., preferably at approximately 90° C. The reaction may also be catalyzed. For example, the reaction may be catalyzed by the addition of an acid, base, or metal. The reagents may be allowed to react for hours, days, or weeks. Preferably, the reaction is allowed to proceed from overnight (e.g., 8-12 hours) to 7 days.

The synthesized poly(beta-amino alcohol) may be purified by any technique known in the art including, but not limited to, precipitation, crystallization, chromatography, distillation, etc. In certain embodiments, the poly(beta-amino alcohol) is purified through repeated precipitations in organic solvent (e.g., diethyl ether, hexane, etc.). In certain embodiments, the poly(beta-amino alcohol) polymer is isolated as a salt. The poly(beta-amino alcohol) is reacted with an acid (e.g., an organic acid or inorganic acid) to form the corresponding salt. In certain embodiments, the tertiary amine is alkylated to form a quaternary ammonium salt of the poly(beta-amino alcohol). The tertiary amines may be alkylated with any alkylating agent, for example, alkyl halides such as methyl iodide may be used to from the quaternary amino groups. The anion associated with the quaternary amine may be any organic or inorganic anion. Preferably, the anion is a pharmaceutically acceptable anion.

In certain embodiments, the reaction mixture results in a mixture of isomers. Such mixtures of products or compounds may be used as is, or a single isomer, or compound, may be purified from the reaction mixture. When an amine is not exhaustively alkylated, the resulting primary, secondary, or tertiary amines may be further reacted with another poly(beta-amino alcohol), diepoxide, epoxide, or other electrophile. The resulting poly(beta-amino alcohol) may then be optionally purified.

In certain embodiments, a desired poly(beta-amino alcohol) is prepared by traditional total synthesis. In certain embodiments, a commercially available amine is the starting material. One or more amino groups of the amine are optionally protected. The unprotected amino groups are reacted with an epoxide-terminated compound. The product is optionally purified. Protecting groups are removed, and the free amino groups are optionally reacted with another poly(beta-amino alcohol), diepoxide, epoxide, or other electrophile. Such a sequence may be repeated depending on the desired complexity of the inventive product being prepared. The final product may then be optionally purified.

In one embodiment, a library of different poly(beta-amino alcohols) is prepared in parallel. A different amine and/or diepoxide is added to each vial in a set of vials or to each well of a multi-well plate used to prepare the library. The array of reaction mixtures is incubated at a temperature and length of time sufficient to allow formation of the poly(beta-amino alcohol) to occur. In one embodiment, the vials are incubated at approximately 90° C. overnight. In certain embodiments, the vials are incubated from 1 to 7 days at approximately 90° C. In certain embodiments, the vials are incubated from 3 to 4 days at approximately 90° C. In certain embodiments, the vials are incubated from 1 to 2 days at approximately 90° C. The poly(beta-amino alcohol) may then be isolated and purified using techniques known in the art. The poly(beta-amino alcohol) may then be screened using high-throughput techniques to identify poly(beta-amino alcohols) with a desired characteristic (e.g., solubility in water, solubility at different pH, ability to bind polynucleotides, ability to bind heparin, ability to bind small molecules, ability to bind protein, ability to form microparticles, ability to increase tranfection efficiency, etc.). In certain embodiments the poly(beta-amino alcohols) may be screened for properties or characteristics useful as coatings, additives, materials, and excipients in biotechnology and biomedical applications such as the coating of medical devices or implants with films or multilayer films, as non-biofouling agents, micropatterning agents, and cellular encapsulation agents. In certain embodiments the poly(beta-amino alcohols) may be screened for properties or characteristics useful in gene therapy (e.g., ability to bind polynucleotides, increase in transfection efficiency) or the administration and/or delivery of therapeutic agents (e.g., polynucleotide, small molecule, antigen, drug, protein, peptide, etc.) to a subject, patient, tissue, organ, or cell, etc.

Poly(Beta-amino Alcohols) as Coatings

The inventive poly(beta-amino alcohols) have several advantages as potential coatings to regulate the foreign body responses as well as cell-material interactions in general. First, they are hydrolytically stable and exceptionally hydrophilic due to the abundant hydroxyl groups. The hydrophilicity has been recognized as an important factor in developing biomaterials with low protein adsorption or cell adhesion (E. Ostuni, R. G. Chapman, R. E. Holmlin, S. Takayama, G. M. Whitesides, *Langmuir* 2001, 17. 5605; N. A. Peppas, J. Z. Hilt, A. Khademhosseini, R. Langer, *Adv. Mater.* 2006, 18, 1345; incorporated herein by reference.) The non-biofouling properties of oligo(ethylene glycol)-terminated self-assembled monolayers (SAMs) (P. Harder, M. Grunze, R. Dahint, G. M. Whitesides, P. E. Laibinis, *J. Phys. Chem. B* 1998, 102, 426; incorporated herein by reference,) zwitterionic SAMs (R. E. Holmlin, X. Chen, R. G. Chapman, S. Takayama, G. M. Whitesides, *Langmuir* 2001, 17, 2841; incorporated herein by reference) and polymers (S. Jiang, Z. Cao, *Adv. Mater.* 2010, 22, 920; incorporated herein by reference) were mainly attributed to the surface hydration. Second, their water-solubility and cationic nature make it relatively simple to coat a wide range of surfaces under biologically-friendly conditions using electrostatic interactions. The mild coating conditions are useful for coatings on medical devices that are sensitive to heat, UV light, or organic solvents. Lastly, the simplicity of their synthesis without requirements of solvent, high temperature, catalyst or additional chemicals, and the availability of a large number of monomers allow one to screen extremely diverse surface chemistries for different biological applications.

Among the different techniques used to modify surfaces, the deposition of polyelectrolyte multilayers (PEM) has emerged as a very easy handling and versatile tool. Based on the alternate adsorption of polycations and polyanions, this technique allows to buildup films with tunable properties: by adjusting several parameters such as the chemical nature of the polyelectrolytes, pH and ionic strength, immersion and rinsing times, post-treatment of the film, it is possible to obtain an almost infinite variety of architectures. The introduction of electrostatic layer-by-layer (LBL) self-assembly also called electrostatic self-assembly (ESA) has shown broad biotechnology and biomedical applications in thin film coating, micropatterning, nanobioreactors, artificial cells, integrated optics, microelectronic devices, sensors, optical memory devices, encapsulation and drug delivery systems. Indeed, this kind of film is easy to manufacture.

Of special importance for biomedical applications is the control of the chemical composition of the surface which can affect biocompatibility or biological activity. Films made from poly(beta-amino alcohols) allow, for example, biomimetic architectures to be created. Applications include also the fabrication of non-adhesive barriers for vascular grafts, the fabrication of films with pro- or anti-coagulant properties or the preparation of hollow capsules for drug release. Bioactivity, such as antimicrobial activity or antifibrosis activity, of the films can be achieved by their functionalization by with amines and diepoxides. For biomaterial applications, biocompatibility is a major requirement: the material or the film covering a material surface must be non-cytotoxic to any living cell and not iatrogenic or allergenic. Another requirement is that the material possesses chemical and physical properties that promote specific cell interactions, either cell adhesion or non-adhesion depending on the final application.

The poly(beta-amino alcohols) of the present invention are biostable. For various applications, the preservation of the structural integrity of the film is crucial. For a long term use of these films (e.g. days, weeks, or months) in aggressive conditions (pH, ionic strength, solvents), it is important that the stability (in particular biostability) of the films is maintained. This property is particularly of interest for films designed to be in contact with a tissue or fluid within the body (soft tissue, blood, lymph, etc.) which contains different types of proteins (for example enzymes), cells and phagocytic cells (for example, white blood cells).

It therefore is an object of this invention to provide a method for producing biostable polyelectrolyte multilayers films made from poly(beta-amino alcohols). It is a further object of the invention to provide a method of producing certain biocompatible materials made from poly(beta-amino alcohols), such materials representing, for example, a surface coated with poly(beta-amino alcohols). Furthermore, it is an object of the invention to provide multilayers films made from poly(beta-amino alcohols) wherein various cells types can adhere and proliferate.

Treatment of Medical Devices and Implants with Poly(Beta-amino Alcohols)

An aspect of the invention includes the treatment of medical devices and implants with poly(beta-amino alcohols) such treatment may inhibit infection or microorganism growth or colonization. Infections associated with medical implants represent a major healthcare problem. A significant percentage of these infections are related to bacterial colonization of implanted medical implants such as Foley catheters (urinary tract infections), surgical drains, meshes, sutures, artificial joints, vascular grafts (wound infections); endotracheal and tracheostomy tubes (respiratory tract infection); and vascular infusion catheters (bloodstream infections). Although any infectious agent can infect medical implant, Staphylococci (*S. aureus, S. epidermidis, S. pyogenes*), Enterococci (*E. coli*), Gram negative aerobic Bacilli, and *Pseudomonas aeruginosa* are common causes. Once a medical implant becomes colonized by bacteria, it must frequently be replaced resulting in increased morbidity for the patient and increased cost to the healthcare system. Often the infected device serves as a source for a disseminated infection which can lead to significant morbidity or even death. Thus, there is a need in the art for medical implants which have a reduced likelihood of an associated infection. Treatment of medical devices and implants with poly(beta-amino alcohols) may reduce the likelihood of infections in medical implants, and further, provides other, related advantages.

A further aspect of the invention includes the treatment of medical devices and implants with poly(beta-amino alcohols) to inhibit fibrosis. "Fibrosis," "scarring," or "fibrotic response" refers to the formation of fibrous tissue in response to injury or medical intervention. Polymers which inhibit fibrosis or scarring are referred to herein as "fibrosis-inhibiting polymers," "anti-scarring polymers," and the like, where these polymers inhibit fibrosis through one or more mechanisms including, but not limited to, inhibiting angiogenesis, inhibiting migration or proliferation of connective tissue cells (such as fibroblasts, smooth muscle cells, vascular smooth muscle cells), reducing ECM production, and/or inhibiting tissue remodeling.

The clinical function of numerous medical implants and devices is dependent upon the device being able to effectively maintain an anatomical, or surgically created, space or passageway. Unfortunately, many devices implanted in the body are subject to a "foreign body" response from the surrounding host tissues. In particular, injury to tubular anatomical structures (such as blood vessels, the gastrointestinal tract, the male and female reproductive tract, the urinary tract, sinuses, spinal nerve root canals, lacrimal ducts, Eustachian tubes, the auditory canal, and the respiratory tract) from surgery and/or injury created by the implantation of medical devices can lead to a well known clinical problem called "stenosis" (or narrowing). Stenosis occurs in response to trauma to the epithelial lining or the entire body tube during the procedure, including virtually any manipulation which attempts to relieve obstruction of the passageway, and is a major factor limiting the effectiveness of invasive treatments for a variety of diseases to be described later.

Stenosis (or "restenosis" if the problem recurs after an initially successful attempt to open a blocked passageway) is a form of response to injury leading to wall thickening, narrowing of the lumen, and loss of function in the tissue supplied by the particular passageway. Physical injury during an interventional procedure results in damage to epithelial lining of the tube and the smooth muscle cells (SMCs) that make up the wall. The damaged cells, particularly SMCs, release cytokines, which recruit inflammatory cells such as macrophages, lymphocytes and neutrophils (i.e., which are some of the known white blood cells) into the area. The white blood cells in turn release a variety of additional cytokines, growth factors, and tissue degrading enzymes that influence the behavior of the constituent cells of the wall (primarily epithelial cells and SMCs). Stimulation of the SMCs induces them to migrate into the inner aspect of the body passageway (often called the "intima"), proliferate and secrete an extracellar matrix—effectively filling all or parts of the lumen with reactive, fibrous scar tissue. Collectively, this creates a thickening of the intimal layer (known in some tissues as "neointimal hyperplasia") that narrows the lumen of the passageway and can be significant enough to obstruct its lumen.

The present invention discloses poly(beta-amino alcohols) which inhibit one or more aspects of the production of excessive fibrous (scar) tissue. Furthermore, compositions and methods are described for coating medical devices and implants with poly(beta-amino alcohol) polymers to allow normal healing to occur.

Also provided by the present invention are methods for treating patients undergoing surgical, endoscopic or minimally invasive therapies where a medical device or implant, coated with poly(beta-amino alcohols), is placed as part of the procedure. As utilized herein, it should be understood that "inhibits fibrosis or stenosis" refers to a statistically significant decrease in the amount of scar tissue in or around the device or an improvement in the luminal area of the device/ implant, which may or may not result in a permanent prohibition of any complications or failures of the device/implant.

Implants and medical devices treated with poly(beta-amino alcohols) may reduce the foreign body response to implantation and limit the growth of reactive tissue on the surface of, or around in the tissue surrounding the implants and medical devices, such that performance is enhanced. In many instances, the devices are used to maintain body lumens or passageways such as blood vessels, the gastrointestinal tract, the male and female reproductive tract, the urinary tract, bony foramena (e.g., sinuses, spinal nerve root canals, lacrimal ducts, Eustachian tubes, the auditory canal), and the respiratory tract, where obstruction of the device by scar tissue in the post-procedural period leads to the adverse clinical sequela or failure of the intervention. Medical devices and implants coated with the inventive poly(beta-amino alcohols) which prevent scar tissue overgrowth and preserve patency can offer significant clinical advantages over uncoated devices.

Implants and other surgical or medical devices may be covered, coated, contacted, combined, loaded, filled, associated with, or otherwise adapted to release the poly(beta-amino alcohols) of the present invention in a variety of manners, including for example: (a) by directly affixing to the implant or device a poly(beta-amino alcohol) or composition (e.g., by either spraying the implant or device with a poly(beta-amino alcohol) film, or by dipping the implant or device into a poly(beta-amino alcohol) solution, or by other covalent or noncovalent means); (b) by coating the implant or device with a substance, such as a hydrogel, which will in turn absorb the poly(beta-amino alcohol) composition (or therapeutic factor above); (c) by interweaving poly(beta-amino alcohol) coated thread (or the poly(beta-amino alcohol) itself formed into a thread) into the implant or device; (d) by inserting the implant or device into a sleeve or mesh which is comprised of or coated with a poly(beta-amino alcohol); (e) constructing the implant or device itself with a poly(beta-amino alcohol); or (f) by otherwise adapting the implant or device to release the poly(beta-amino alcohol). Within preferred embodiments of the invention, the composition should firmly adhere to the implant or device during storage and at the time of insertion. The poly(beta-amino alcohol) or composition should also preferably not degrade during storage, prior to insertion, or when warmed to body temperature after insertion inside the body (if this is required). In addition, it should preferably coat or cover the desired areas of the implant or device smoothly and evenly, with a uniform distribution of poly(beta-amino alcohol). Within some preferred embodiments of the invention, the poly(beta-amino alcohol) or composition should provide a uniform, predictable, prolonged release of the poly(beta-amino alcohol) into the tissue surrounding the implant or device once it has been deployed. Within other preferred embodiments of the invention, the poly(beta-amino alcohol) or composition should resist a prolonged release of the poly(beta-amino alcohol) into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated).

Within certain embodiments of the invention, the poly(beta-amino alcohol) can be deposited directly onto all or a portion of the device (see, e.g., U.S. Pat. Nos. 6,096,070 and 6,299,604; both incorporated herein by reference) or admixed with a delivery system or carrier (e.g., a polymer, liposome, or additional agent as discussed above) which is applied to all or a portion of the device.

To further modulate or prevent the release of the poly(beta-amino alcohol) from the medical implant, portions of or the entire medical implant may be further coated with additional agents or polymers to increase the flexibility (e.g., plasticizer-glycerol, triethyl citrate), lubricity (e.g., hyaluronic acid), biocompatibility, bioactivity, or hemocompatability (e.g., heparin) of the coating.

Polynucleotide Complexes

The ability of cationic compounds to interact with negatively charged polynucleotides through electrostatic interactions is well known. Cationic lipids such as Lipofectamine have been prepared and studied for their ability to complex and transfect polynucleotides. The interaction of the lipid with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive ζ-potential, more preferably the ζ-potential is between 0 and +30.

The poly(beta-amino alcohols) of the present invention possess tertiary amines. Although these amines are hindered, they are available to interact with a polynucleotide (e.g., DNA, RNA, synthetic analogs of DNA and/or RNA, DNA/RNA hydrids, etc.). Polynucleotides or derivatives thereof are contacted with the inventive poly(beta-amino alcohols) under conditions suitable to form polynucleotide/poly(beta-amino alcohol). The polymer is preferably at least partially protonated so as to form a complex with the negatively charged polynucleotide. In certain embodiments, the polynucleotide/poly(beta-amino alcohol) complexes form particles that are useful in the delivery of polynucleotides to cells. In certain embodiments, multiple poly(beta-amino alcohols) may be associated with a polynucleotide molecule. The complex may include 1-100 poly(beta-amino alcohols), 1-1000 poly(beta-amino alcohols), 10-1000 poly(beta-amino alcohols), or 100-10,000 poly(beta-amino alcohols).

In certain embodiments, the complex may form a particle. In certain embodiments, the diameter of the particles ranges from 10-500 micrometers. In certain embodiments, the diameter of the particles ranges from 10-1200 micrometers. In certain embodiments, the diameter of the particles ranges from 50-150 micrometers. In certain embodiments, the diameter of the particles ranges from 10-500 nm, more preferably the diameter of the particles ranges from 10-1200 nm, and most preferably from 50-150 nm. The particles may be associated with a targeting agent as described below. In certain embodiments, the diameter of the particles ranges from 10-500 pm, more preferably the diameter of the particles ranges from 10-1200 pm, and most preferably from 50-150 pm. The particles may be associated with a targeting agent as described below. The film architecture is precisely designed and can be controlled to 1 nm precision with a range from 1 to 150000 nm and with a definite knowledge of its molecular composition.

The polynucleotide to be complexed, encapsulated by the inventive poly(beta-amino alcohols), or included in a composition with the inventive poly(beta-amino alcohols) may be any nucleic acid including, but not limited to, RNA and DNA. In certain embodiments, the polynucleotide is DNA. In certain embodiments, the polynucleotide is RNA.

In certain embodiments, the polynucleotide is an RNA that carries out RNA interference (RNAi). The phenomenon of RNAi is discussed in greater detail, for example, in the following references, each of which is incorporated herein by reference: Elbashir et al., 2001, *Genes Dev.,* 15:188; Fire et al., 1998, *Nature,* 391:806; Tabara et al., 1999, *Cell,* 99:123; Hammond et al., *Nature,* 2000, 404:293; Zamore et al., 2000, *Cell,* 101:25; Chakraborty, 2007, *Curr. Drug Targets,* 8:469; and Morris and Rossi, 2006, *Gene Ther.,* 13:553. In certain embodiments, the polynucleotide is a dsRNA (double-stranded RNA). In certain embodiments, the polynucleotide is an siRNA (short interfering RNA). In certain embodiments, the polynucleotide is an shRNA (short hairpin RNA).

In certain embodiments, the polynucleotide is an miRNA (micro RNA). micro RNAs (miRNAs) are genomically encoded non-coding RNAs of about 21-23 nucleotides in length that help regulate gene expression, particularly during development (see, e.g., Bartel, 2004, *Cell,* 116:281; Novina and Sharp, 2004, *Nature,* 430:161; and U.S. Patent Publication 2005/0059005; also reviewed in Wang and Li, 2007, *Front. Biosci.,* 12:3975; and Zhao, 2007, *Trends Biochem. Sci.,* 32:189; each of which are incorporated herein by reference).

In certain embodiments, the polynucleotide is an antisense RNA.

In some embodiments, a dsRNA, siRNA, shRNA, miRNA and/or antisense RNA can be designed and/or predicted using one or more of a large number of available algorithms. To give but a few examples, the following resources can be utilized to design and/or predict dsRNA, siRNA, shRNA, and/or miRNA: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.,* 22:326; Naito et al., 2006, *Nucleic Acids Res.,* 34:W448; Li et al., 2007, *RNA,* 13:1765; Yiu et al., 2005, *Bioinformatics,* 21:144; and Jia et al., 2006, *BMC Bioinformatics,* 7: 271; each of which is incorporated herein by reference).

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al., *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al., *Nature* 391: 806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10 (2): 123-126, discussion 127, 2000*; Methods in Enzymology* volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al., *J. Mol. Med.* 75(4):267-282, 1997; incorporated herein by reference).

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection.

The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health and can be found on the internet (www.niaid.nih.gov/daids/vaccine/pdf/compendium.pdf, incorporated herein by reference; see also Allison *Dev. Biol. Stand.* 92:3-11, 1998; Unkeless et al., *Annu. Rev. Immunol.* 6:251-281, 1998; and Phillips et al., *Vaccine* 10:151-158, 1992; each of which is incorporated herein by reference).

The antigenic protein or peptides encoded by the polynucleotide may be derived from such bacterial organisms as *Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Particles

The poly(beta-amino alcohols) of the present invention may also be used to form drug delivery devices. The inventive poly(beta-amino alcohols) may be used to encapsulate agents including polynucleotides, small molecules, proteins, peptides, metals, organometallic compounds, etc. The inventive poly(beta-amino alcohols) have several properties that make them particularly suitable in the preparation of drug delivery devices. These include: 1) the ability of the lipid to complex and "protect" labile agents; 2) the ability to buffer the pH in the endosome; 3) the ability to act as a "proton sponge" and cause endosomolysis; and 4) the ability to neutralize the charge on negatively charged agents. In certain embodiments, the poly(beta-amino alcohols) are used to form particles containing the agent to be delivered. These particles may include other materials such as proteins, carbohydrates, synthetic polymers (e.g., PEG, PLGA), and natural polymers.

In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers.

In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm.

The inventive particles may be prepared using any method known in this art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

Micelles and Liposomes

The poly(beta-amino alcohols) of the invention may also be used to prepare micelles or liposomes. Many techniques for preparing micelles and liposomes are known in the art, and any method may be used with the inventive poly(beta-amino alcohols) to make micelles and liposomes. In addition, any agent including polynucleotides, small molecules, proteins, peptides, metals, organometallic compounds, etc. may be included in a micelle or liposome. Micelles and liposomes are particularly useful in delivering hydrophobic agents such as hydrophobic small molecules.

In certain embodiments, liposomes (lipid or poly(beta-amino alcohol) vesicles) are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). See Walde, P. "Preparation of Vesicles (Liposomes)" In *Encyclopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein. The preparation of liposomes involves preparing the poly(beta-amino alcohols) for hydration, hydrating the poly (beta-amino alcohols) with agitation, and sizing the vesicles to achieve a homogenous distribution of liposomes. Poly (beta-amino alcohols) are first dissolved in an organic solvent to assure a homogeneous mixture of poly(beta-amino alcohols). The solvent is then removed to form a polymer-derived film. This polymer-derived film is thoroughly dried to remove residual organic solvent by placing the vial or flask on a vaccuum pump overnight. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm.

In certain embodiments, the polynucleotide is an RNA molecule (e.g., an RNAi molecule). In other embodiments, the polynucleotide is a DNA molecule. In certain embodiments, the amount of poly(beta-amino alcohol) in the liposome ranges from 30-80 mol %, preferably 40-70 mol %, more preferably 60-70 mol %. These liposomes may be prepared using any method known in the art. In certain embodiments (e.g., liposomes containing RNAi molecules), the liposomes are prepared by lipid extrusion.

Certain poly(beta-amino alcohols) can spontaneously self assemble around certain molecules, such as DNA and RNA, to form liposomes. In some embodiments, the application is the delivery of polynucleotides. Use of these poly(beta-amino alcohols) allows for simple assembly of liposomes without the need for additional steps or devices such as an extruder.

The following scientific papers described other methods for preparing liposomes and micelles: Narang et al., "Cationic Lipids with Increased DNA Binding Affinity for Nonviral Gene Transfer in Dividing and Nondividing Cells" *Bioconjugate Chem.* 16:156-68, 2005; Hofland et al., "Formation of stable cationic lipid/DNA complexes for gene transfer" *Proc. Natl. Acad. Sci. USA* 93:7305-7309, July 1996; Byk et al., "Synthesis, Activity, and Structure—Activity Relationship Studies of Novel Cationic Lipids for DNA Transfer" *J. Med. Chem.* 41(2):224-235, 1998; Wu et al., "Cationic Lipid Polymerization as a Novel Approach for Constructing New DNA Delivery Agents" *Bioconjugate Chem.* 12:251-57, 2001; Lukyanov et al., "Micelles from lipid derivatives of water-soluble polymers as delivery systems for poorly soluble drugs" *Advanced Drug Delivery Reviews* 56:1273-1289, 2004; Tranchant et al., "Physicochemical optimisation of plasmid delivery by cationic lipids" *J. Gene Med.* 6:S24-S35, 2004; van Balen et al., "Liposome/Water Lipophilicity: Methods, Information Content, and Pharmaceutical Applications" *Medicinal Research Rev.* 24(3):299-324, 2004; each of which is incorporated herein by reference.

Agents to be Delivered

The agents to be delivered by the systems of the present invention may be therapeutic, diagnostic, or prophylactic agents. Any chemical compound to be administered to an individual may be delivered using the inventive complexes, picoparticles, nanoparticles, microparticles, micelles, or liposomes. The agent may be a small molecule, organometallic compound, nucleic acid, protein, peptide, polynucleotide, metal, an isotopically labeled chemical compound, drug, vaccine, immunological agent, etc.

In certain embodiments, the agents are organic compounds with pharmaceutical activity. In another embodiment of the invention, the agent is a clinically used drug. In certain embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments of the present invention, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

These antigens may be in the form of whole killed organisms, peptides, proteins, glycoproteins, carbohydrates, or combinations thereof.

Targeting Agents

The inventive complexes, liposomes, micelles, microparticles, picoparticles and nanoparticles may be modified to include targeting agents since it is often desirable to target a particular cell, collection of cells, or tissue. A variety of targeting agents that direct pharmaceutical compositions to particular cells are known in the art (see, for example, Cotten et al., *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, nucleic acids, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Pharmaceutical Compositions

Once the complexes, micelles, liposomes, or particles have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Some aspects of the invention include a pharmaceutical composition comprising a poly(beta-amino alcohol) polymer of the formula:

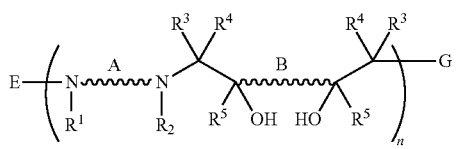

and a pharmaceutical agent.

Some aspects of the invention include a pharmaceutical composition comprising a poly(beta-amino alcohol) polymer of the formula:

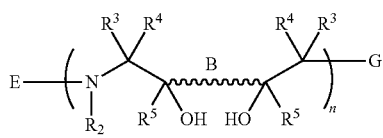

and a pharmaceutical agent.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

These and other aspects of the present invention will be further appreciated upon consideration of the following Examples, which are intended to illustrate certain particular embodiments of the invention but are not intended to limit its scope, as defined by the claims.

EXAMPLES

Using combinatorial polymerization, a new class of novel cationic polymers, poly(β-amino alcohols) (PBAAs), were synthesized which can be used as coatings for biomedical devices. Moreover, these polymers covered a wide range of chemical functionality and can be used to study the effect of surface chemistry on the foreign body responses. Through an initial in vitro screening, the polymer coatings that promoted or inhibited the activation of mouse monocyte/macrophage cells were identified by measuring the secretion of a pro-inflammatory cytokine, tumor necrosis factor α (TNF-α). The polymers that induced highest and lowest levels of TNF-α secretion were used to coat carboxylated polystyrene microparticles, which were subsequently injected into mice subcutaneously. Twenty four hours after injection, significantly different levels of inflammatory cell recruitment into the implantation sites were observed using live animal imaging. Histological analysis of fibrosis around the particles 30 days after injections showed correlation with both the in vitro and live imaging results.

Example 1

Polymer Synthesis and Characterization

A large number of chemically diverse cationic polymers were synthesized using combinatorial polymerization. The monomers used to make the poly(beta-amino alcohols) were purchased from Sigma-Aldrich (Milwaukee, Wis.), TCI America (Portland, Oreg.) and Acros Organics (Fisher Scientific, Pittsburgh, Pa.). All the epoxide and amine monomers used in these Examples are liquid at room temperature. The polymerizations took place in bulk at room temperature under vigorous stirring until solidification typically within twenty-four hours. Solvents such as dimethyl sulfoxide (DMSO) or dichloromethane could also be used but were not required for the reactions. To ensure all the polymers were terminated with amines, the molar ratio between amines and epoxides were controlled to be 1 to 1.2 in the polymerization. The polymers that were not soluble in water or form hydrogels with water were eliminated in the subsequent coatings. The molecular weights of representative PBAAs were determined using cationic columns in a Viscotek Gel Permeation Chromatography. A 2.7% acetic acid solution was used as the running solvent and the molecular weights were calculated relative to polyethyleneimine (PEI) standards. The polymers were also characterized using a 400 MHz NMR Bruker Avance 400. The solvent was deuterated DMSO or chloroform.

Example 2

Surface Coatings and Characterization

The PBAA solutions for coatings were made by dissolving the polymers in either DI water or slightly acidic solution at the concentration of 0.01 mol/L by repeating unit. The pHs of the solutions were measured using a bench-top pH meter (Mettler Toledo). The solutions were coated on 96-well glass-bottom plates (Matrix Technologies Corp.) for in vitro screening. Each well was soaked with 150 μL different PBAA solutions for 1 hour. The wells were then washed thoroughly with DI water 5 times. The coatings were characterized with a Kratos Axis Ultra X-ray photoelectron spectrometer (XPS) (Kratos Analytical) with a monochromatized Al KR X-ray source. The takeoff angle relative to the sample substrate for this measurement was located at 90°. This means that the effective sampling depth is about a few nanometers. We seek only a qualitative confirmation of the surface coating at this stage, no attempt was made to obtain an accurate estimate of the actually surface coverage and coating thickness. The XPS signal from the nitrogen in the PBAA was used to confirm the surface coatings. For in vivo tests, the PBAAs were coated on carboxylated polystyrene microspheres (20 μm diameter, PolySciences Inc.) The as-received microspheres were first washed with DI water 6 times and then incubated in 0.01 mol/L PBAA solutions for 2 hours for complete electrostatic bonding. The particles were washed again with DI water for 6 times and finally dispersed in PBS at a 10% (w/v) concentration for subsequent injections.

Example 3

In Vitro Screening

For in vitro screening, the PBAA coated glass-bottom plates were first sterilized using 70% ethanol for 10 minutes and washed thoroughly with PBS. RAW 264.7 cells (ATCC) were cultured in DMEM supplemented with 10% fetal calf serum and penicillin/streptomycin (all from Invitrogen). Cells were seeded at a density of 150,000 cells/cm$^2$ on polymer-coated glass surfaces in serum containing media, incubated at 37° C. for 18 h, and then analyzed for release of TNF-α and cell viability. To assess for TNF-α, cell culture supernatant was removed and analyzed by ELISA (kit from R&D Systems) according to the manufacturer's instructions. Briefly, 96-well ELISA plates (BD Falcon) were coated with capture antibody overnight at 4° C. Plates were then washed three times with 0.01% Tween in PBS, blocked with 1% BSA in PBS, and then incubated with samples. After thorough washing, the captured TNF-α was detected using a detection antibody, HRP-conjugated streptavidin, and Ultra-TMB substrate (Pierce). The reaction was stopped with 0.16M sulfuric acid, and absorbance at 490 nm was determined using a Spectramax plate reader (Molecular Devices). To assay for cell viability, cells were incubated with MTS ([3-(4,5-dimethylthiazol-2-yl)-5-(3-carboxymethoxyphenyl)-2-(4-sulfophenyl)-2H-tetrazolium) reagent (Promega) for 2 hours at 37° C., and absorbance at 490 nm was measured. Visualization of live and dead cells was performed by staining with calcein and ethidium homodimer-1, respectively (Invitrogen). Fluorescence was visualized on a Zeiss inverted microscope equipped with a 20× objective. Images were acquired using AxioVision software. All experiments were performed in triplicate and error bars indicate standard deviation from the mean. The cell morphology was further observed with a JEOL-6060SEM (JEOL Ltd., Japan) scanning electron microscope (SEM). The cells were first fixed using 4% formaldehyde solution for 30 minutes after being washed with PBS twice. The fixed samples were then rinsed with DI water and dehydrated using a sequence of progressively more concentrated ethanol solutions (30%, 50%, 70%, 90% and 100%). After a few hours of air-drying, the cells were sputter-coated with a 2-3 nm layer of gold for imaging by use of a Desk II cold sputter/etch unit (Denton Vacuum LLC).

Example 4

In Vivo Imaging

The PBAA coated microparticles were injected subcutaneously in an array format on the backs of immunocompetent hairless mice (SKH1, Charles River Laboratories, Wilmington, Mass.). Each injection contained 100 μL 10% (w/v) particle suspension in PBS. The mice were anesthetized with isoflurane inhalation and their backs were scrubbed with alcohol patches before the injections. In vivo fluorescence and bioluminescence imaging was performed by using an IVIS imaging system (IVIS Spectrum, Caliper Life Sciences, Hopkinton, Mass.) and the images were analyzed with Living Image acquisition and analysis software (Caliper Life Sciences, Hopkinton, Mass.). The Prosense®750 (VisEn Medica, Woburn, Ma1) was injected through the tail vein (i.v.) at a dose of 100 μL per mouse 24 hours before imaging. Luminol (Aldrich) was injected into intraperitoneal (i.p.) space 20 minutes before imaging at a dose of 5 mg per mouse. The mice were anesthetized with isoflurane for the i.p. injection and imaging.

Histological Analysis Mice were euthanized using $CO_2$ gas. Skin samples containing the injected microparticles were fixed in AccuStain (Aldrich), embedded in paraffin, sectioned and stained with Masson Trichrome based on standard procedures. The histology slides were then observed using a Zeiss inverted microscope. Images at both 5× and 20× were taken to view the global fibrosis around the entire implantation site as well as local fibrosis around individual particles.

Example 5

In Vitro Screening

A significant concern with respect to these cationic polymer coatings is their cytotoxicity. Furthermore, it was unknown whether the differences in TNF-α observed could be attributed to differences in cell viability. Using an MTS assay to measure cell viability, we found that although the different PBAA coatings exhibited significantly different levels of macrophage activation, cell viability on all surfaces were essentially the same and comparable to cells seeded on control surfaces, as shown in FIG. 2(*a*). Fluorescent live/dead staining assay further confirmed that the cells all remained alive whether they were activated on the uncoated surface or not activated on the PBAA-coated surface. (FIGS. 2(*b*) and (*c*)) The morphologies of the cells seeded on different surfaces were dramatically different, and the trends were similar to that observed by SEM.

To investigate the stability of the polymer coating, we performed X-ray photoelectron spectroscopy (XPS), as shown in FIG. 2(*e*). From the signals of N1s, characteristic peak for tertiary amine groups in PBAAs, we found that the coated surfaces, as prepared or presoaked with PBS for twenty-four hours, both have the same amount of PBAA coatings, while the uncoated glass surface has no detectable N1s signal, as expected. To confirm that the activation of macrophages was influenced solely by the surface coatings, further control experiments with 3 inhibitory PBAAs were performed. We incubated surfaces that had been coated with polymers with media for twenty-four hours, and then examined the amount of TNF-α secreted by cells seeded on the normal coatings, on the coatings that have been pre-soaked with media for twenty-four hours, and on the uncoated surfaces but incubated with media that had been preconditioned with the coated surfaces for twenty-four hours. The controls in all three cases were uncoated surfaces. From the results shown in FIG. 2(*d*), we see that cells seeded on PBAA-coated surfaces that had been pre-soaked with media still secreted low levels of TNF-α, similar to cells seeded on surfaces coated normally with PBAA. Furthermore, cells seeded on uncoated surfaces and incubated with media that had been pre-conditioned secreted high levels of TNF-α, similar to cells seeded on uncoated surfaces and incubated with normal media. These results suggest that the coatings rather than any possible polymers dissolved in the media were responsible for the inhibition of TNF-α secretion.

To first screen the effect of different PBAA coatings on monocyte/macrophage activation, we immobilized the polymers on 96-well plates with glass bottoms. The glass surfaces, which are generally hydrophilic and negatively charged under physiological conditions, have been commonly used to immobilize polycations and build multilayer polyelectrolyte coatings (J. D. Mendelsohn, S. Y. Yang, J. A. Hiller, A. I. Hochbaum, M. F. Rubner, *Biomacromolecules* 2003, 4, 96.) For the in vitro screen, we measured the response of a mouse monocyte/macrophage cell line to the coatings. It is generally thought that macrophages are one of the dominant cell types that regulate foreign body responses. (J. M. Anderson, *Cardiovasc. Pathol.* 1993, 2, S33) The behavior of macrophages on surfaces with different charge densities, (J. A. Hunt, B. F. Flanagan, P. J. McLaughlin, I. Strickland, D. F. Williams, *J. Biomed. Mater. Res.* 1996, 31, 139) topography (A. K. Refai, M. Textor, D. M. Brunette, J. D. Waterfield, *J. Biomed. Mater. Res.* 2004, 70A, 194; N. E. Paul, et al., *Biomaterials* 2008, 29, 4056) and modulus (E. F. Irwin, K. Saha, M. Rosenbluth, L. J. Gamble, D. G. Castner, K. E. Healy, *J. Biomater. Sci. Polymer Edn* 2008, 19, 1363) has been widely studied. It was found in particular that the surface chemistry (W. G. Brodbeck, Y. Nakayama, T. Matsuda, E. Colton, N. P. Ziats, J. M. Anderson, *Cytokine*, 2002, 18, 311; R. J. Schutte, A. Parisi-Amon, W. M. Reichert, *J. Biomed. Mater. Res.* 2009, 88A, 128; S. Kamath, D. Bhattacharyya, C. Padukudru, R. B. Timmons, L. Tang, *J. Biomed. Mater. Res.* 2008, 86A, 617) has direct influence on the macrophage-material interactions, although the chemical diversity of the surface chemistries that have been explored is very limited. Moreover, there is often a lack of in vivo studies to correlate the in vitro results.

The response of the monocyte/macrophage cells to different cationic polymer coatings were assessed by measuring the TNF-α concentration in the cell culture media 18 hours after cell seeding. TNF-α is one of the most important pro-inflammatory cytokines and plays a role in further recruitment and activation of inflammatory cells. The level of TNF-α secreted is an indicator of the macrophage activation. FIG. 2(*a*) shows the relative TNF-α concentration secreted by cells seeded on several of the coatings that were tested. The uncoated glass-bottom well is used as a control. PLL and PAH, two typical commercially available cationic polymers, were used as additional references. Cells seeded on the best PBAAs showed a 10-fold lower level of TNF-α compared to cells seeded on the control, uncoated glass surface, and 35-fold decrease compared to cells on the PLL coating. Scanning electron microscope (SEM) images revealed dramatic differences in cell morphology, as shown in FIGS. 2(*b*) and (*c*). Cells that secreted high levels of TNF-α were well-spread, whereas cells that secreted low levels of TNF-α remained rounded. Remarkably, the PBAAs that promoted the macrophage activation were all made from similar amine monomers (#22, #35, #36) that contain dimethoxy, diethoxy or dioxolane groups, while the PBAAs that inhibited cell activation contained at least two tertiary amines per repeating unit (e.g., A10, A12, B20 and B30). The most inhibitory PBAA was A12—which has three tertiary amine groups for every repeating unit. While the mechanism by which the chemical functional groups affect macrophage activation is not clear at this stage, it is possible that the composition and conformation of proteins adsorbed on the surface dictates the behavior of monocyte/macrophage cells.

Example 6

In Vivo Test

To examine the inflammatory response to these novel materials in vivo, four different PBAAs that induced the highest (A35 and B35) and lowest (A12 and B12) levels of TNF-α secretion were chosen to coat 20 μm carboxylated polystyrene beads. FIG. 3 (*a*) shows a SEM image of the beads with a schematic illustrating the coating. The size of the bead was selected to be large enough to limit phagocytosis but small enough to allow easy injection under the skin. The chemical structures of A12 and B35 are shown in FIG. 3 (*b*), and the configuration of the injections is shown by a schematic in FIG. 3 (*c*). To measure the early foreign body responses to the injected beads, we examined the inflammatory response to beads coated with different PBAAs in live animals using two different imaging probes, Prosense®750 and luminol. Prosense is fluorescence sensor that measures the activity of Cathepsin B (and to a lesser extent Cathepsins K, L, and S) (M. Nahrendorf, D. E. Sosnovik, P. Waterman, F. K. Swirski, A. N. Pande, E. Aikawa, J-L. Figueiredo, M. J. Pittet, R. Weissleder, *Circ. Res.* 2007, 100, 1218). The fluorescence signal correlates with the presence of neutrophils and monocyte/macrophages and can be used to assess the acute inflammatory response (K. M. Bratlie, T. T. Dang, S. Lyle, M. Nahrendorf, R. Weissleder, R. Langer, D. G. Anderson, *PLoS ONE* 2010, 5, e10032). FIG. 3 (*d*) shows the fluorescent images obtained using Prosense 24 hours after the particle injections. Quantification of the fluorescent images show that A12 and B12 have lower signals than the A35 and B35, consistent with the trends observed in vitro. Similar results were observed using luminol, a bioluminescent compound that reacts with reactive oxygen species (ROS) and emits blue luminescence (S. Gross, S. T. Gammon, B. L. Moss, D. Rauch, J. Harding, J. W. Heinecke, L. Ratner, D. Piwnica-Worms, *Nature Medicine* 2009, 15, 455). It is known that during inflammation in response to foreign bodies, neutrophils and macrophages release ROS, and therefore luminol has been used to measure the inflammatory response to implanted biomaterials (W. F. Liu et al.). The luminescent images obtained with luminol are shown in FIG. 3 (*e*) and confirm again the correlation of the early foreign body responses with the in vitro screening results.

Example 7

Histological Analyses

Figure 4A:
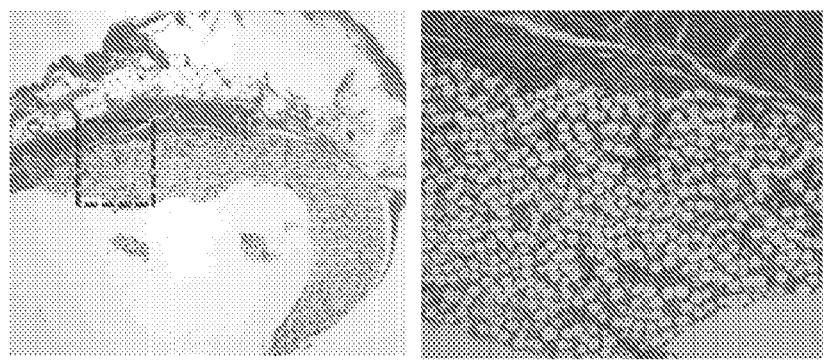
FIG. 4 depicts Masson's trichrome stained skin tissues containing subcutaneously injected particles 30 days after injection. (a) uncoated particles; (b) A12 coated particles and (c) B35 coated particles. The images on the right are magnifications of the enclosed regions of the images on the left. The white spheres in the images are the 20 μm particles. Note that many particles detached during the sample preparation in the cases of (a) and (b).
Figure 4B:
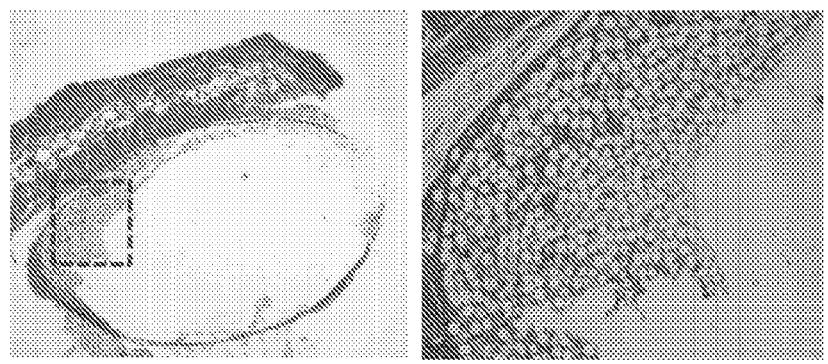
Figure 4C:
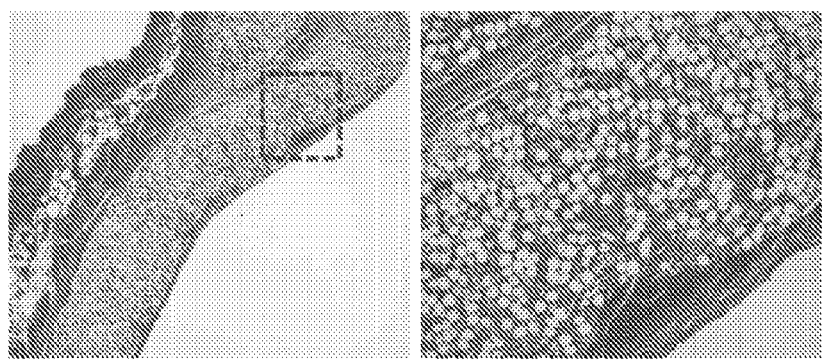

Histological analysis of skin tissue 30 days after injection of the most inflammatory coating B35 and the least inflammatory coating A12 as well as uncoated control is shown in FIG. 4. The Masson trichrome-stained collagen, which indicates fibrosis, appears blue in these micrographs. The low magnification images show that the fibrosis around the entire implantation site occurred in all three cases. This is the usual response of the body to the continuous presence of foreign materials. However, interestingly, fibrosis around individual particles was significantly different as shown by the high magnification images. From the density of deposited collagen or amount of blueness in the images, it is clear that relative to the control uncoated beads, there is less fibrosis around particles with the A12 coating, and more around particles with the B35 coating. This difference is a direct reflection of the effect of surface coatings on the foreign body response, and is consistent with the results from in vitro and live animal imaging experiments.

Other Embodiments

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function. Use of ordinal terms such as first, second, third, etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

This application refers to various issued patents, published patent applications, journal articles, books, manuals, and other publications, all of which are incorporated herein by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A polymer of formula:

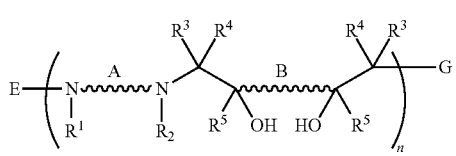

wherein:

B is a bond; substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;

$R^2$ is substituted or unsubstituted, branched or unbranched, acyclic $C_{1-20}$ heteroaliphatic with at least one nitrogen atom;

each of $R^3$, $R^4$, and $R^5$ is independently hydrogen; substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;

each

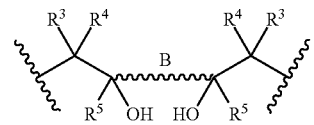

optionally forms a cyclic structure;

each of E and G is, independently, hydrogen, $C_1$-$C_6$ alkyl,

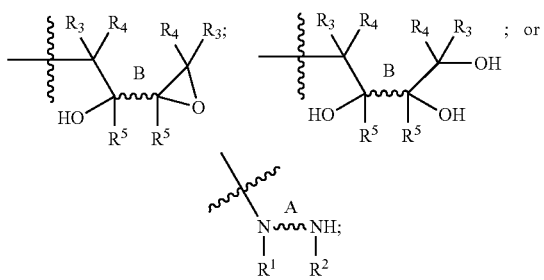

and n is an integer from 2 to 10,000, inclusive;

or a salt thereof.

2. The polymer of claim 1, wherein B is substituted or unsubstituted, branched or unbranched, cyclic or acyclic $C_{1-20}$ aliphatic.

3. The polymer of claim 1, wherein B is substituted or unsubstituted, branched or unbranched, cyclic or acyclic $C_{1-20}$ heteroaliphatic.

4. The polymer of claim 1, wherein B is selected from the group consisting of:

a bond,

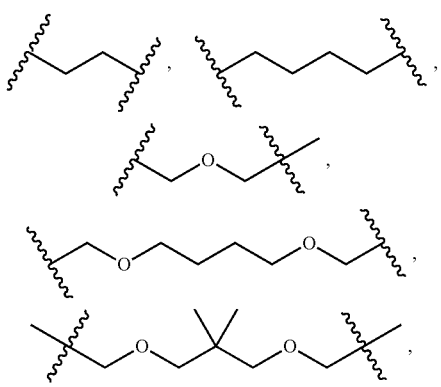

-continued

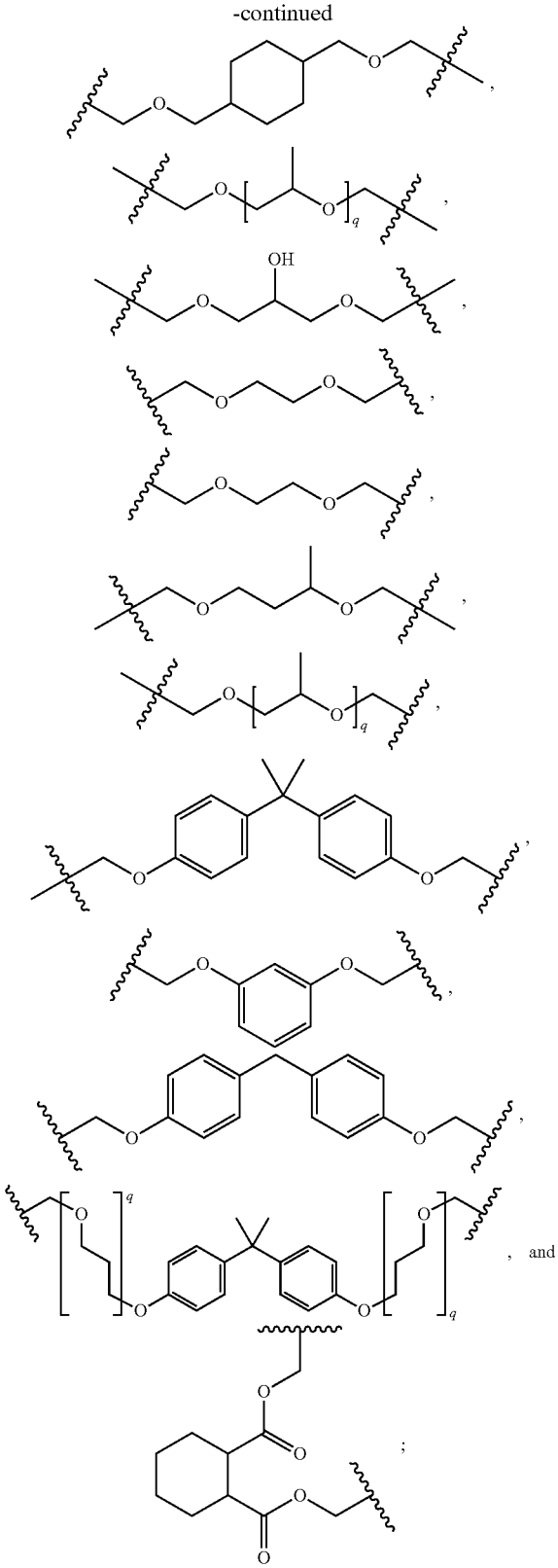

wherein each q is, independently, an integer between 0 and 10, inclusive.

5. The polymer of claim 1, wherein $R^2$ is substituted or unsubstituted, branched or unbranched, acyclic $C_{1-6}$ heteroaliphatic with at least one nitrogen atom.

6. The polymer of claim 1, wherein $R^2$ is substituted or unsubstituted, branched or unbranched, acyclic $C_{1-6}$ heteroaliphatic with one nitrogen atom.

7. The polymer of claim 1, wherein $R^2$ is selected from the group consisting of:

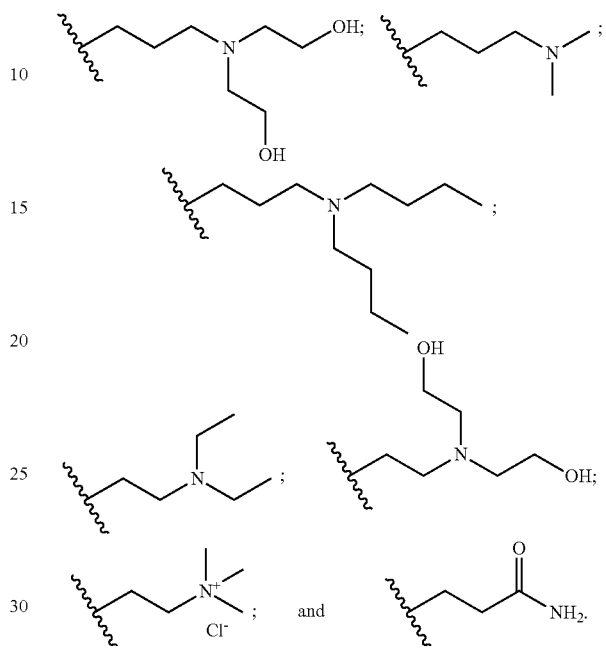

8. The polymer of claim 1, wherein all $R^3$ and $R^4$ are hydrogen.

9. The polymer of claim 1, wherein $R^5$ is hydrogen.

10. The polymer of claim 1 prepared from:

an epoxide selected from the group consisting of:

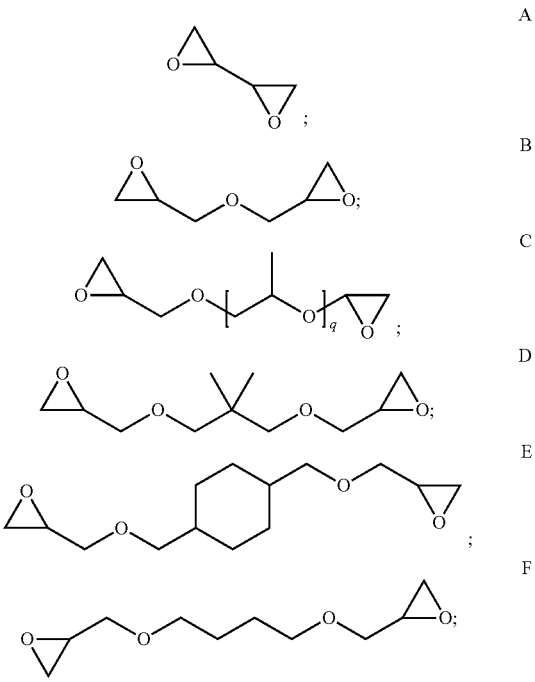

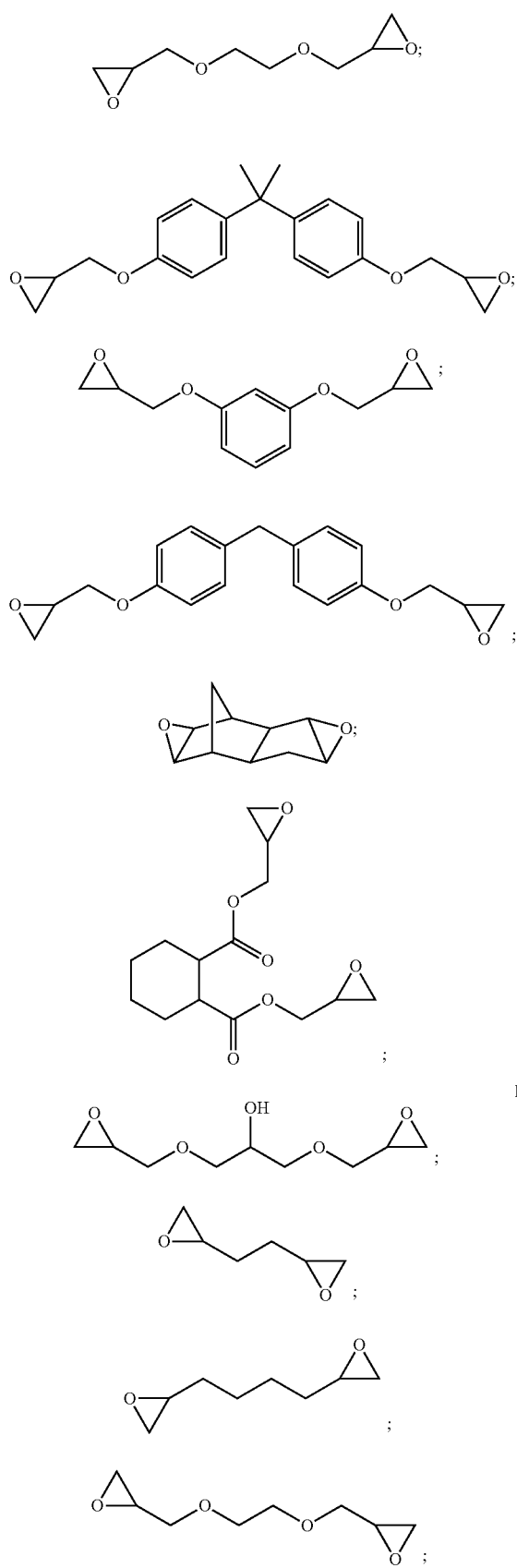
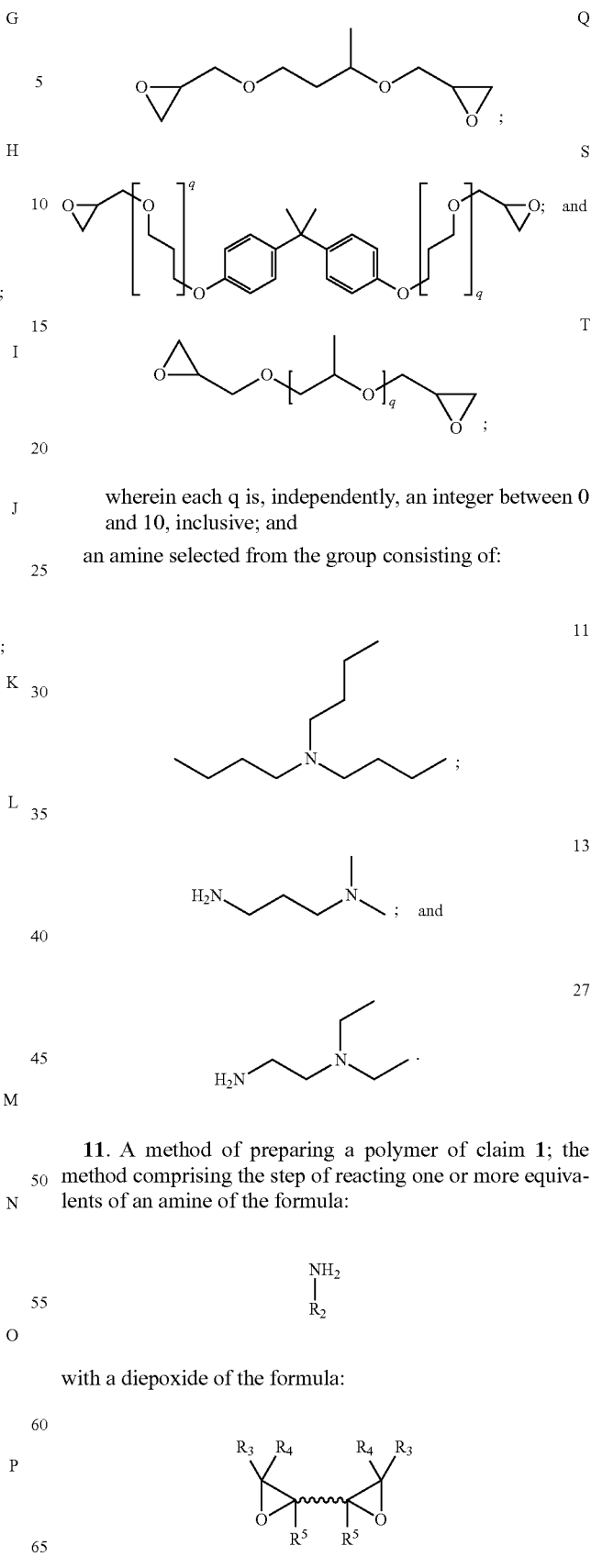
wherein each q is, independently, an integer between 0 and 10, inclusive; and
an amine selected from the group consisting of:
11. A method of preparing a polymer of claim 1; the method comprising the step of reacting one or more equivalents of an amine of the formula:
with a diepoxide of the formula:

to form a polymer of formula:

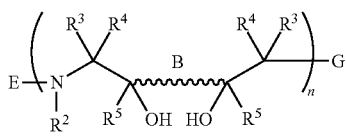

wherein $R^2$, $R^3$, $R^4$, $R^5$, B, n, E, and G are as defined in claim 1.

12. A polymer prepared from:
an epoxide selected from the group consisting of:

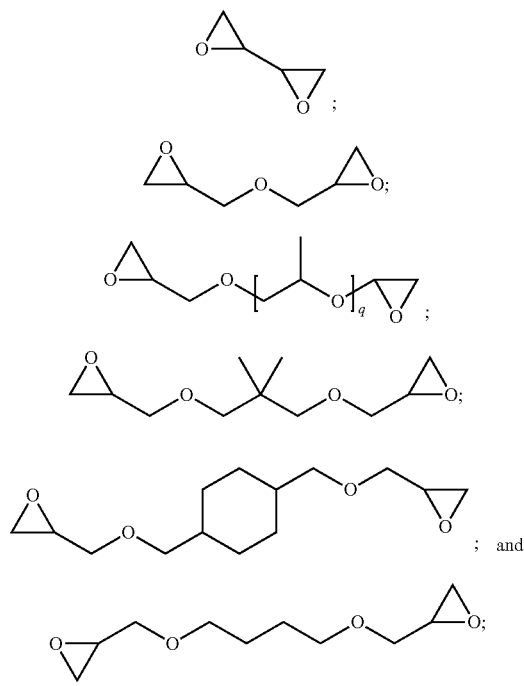

wherein q is an integer between 0 and 10, inclusive; and
an amine selected from the group consisting of:

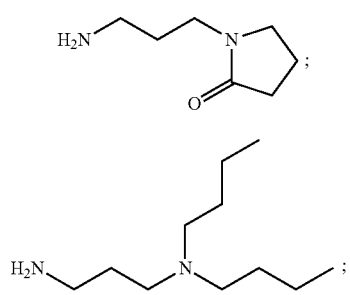

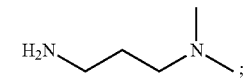

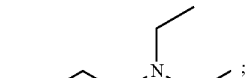

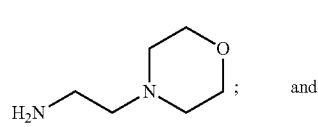

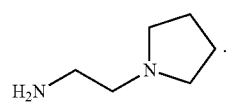

13. The polymer of claim 12, selected from the group consisting of: A29, F05, B11, A05, B29, A11, F29, C13, F27, A27, B27, A30, and B30.

14. The polymer of claim 13, wherein the polymer is B30.

15. A pharmaceutical composition comprising a polymer of claim 1; and a pharmaceutical agent.

16. A liposome comprising a polymer of claim 1; and an agent to be delivered, wherein the agent is selected from the group consisting of a polynucleotide, RNA, a small molecule, a drug, a peptide, or a gas.

17. A microparticle comprising a polymer of claim 1; and an agent to be delivered.

18. A micelle comprising a polymer of claim 1; and an agent to be delivered.

19. A complex comprising a polymer of claim 1; and a polynucleotide.

20. A method of encapsulating an agent in a matrix of a polymer of claim 1 to form microparticles, the method comprising the steps of:
providing an agent;
providing a polymer of claim 1; and
contacting the agent and the polymer under suitable conditions to form microparticles.

21. A method of administering an agent, the method comprising the step of administering to a subject in need thereof a therapeutically effective amount of a pharmaceutical composition comprising a polymer of claim 1 and an agent to be delivered.

22. A medical device coated with a polymer of claim 1.

23. An implant coated with a polymer of claim 1.

24. A surface coated with a polymer of claim 1.

25. A method of coating a substrate with a polymer of claim 1, the method comprising steps of:
providing an substrate;
providing a polymer of claim 1; and
contacting the substrate and the polymer under suitable conditions to form a coating.

* * * * *